US010010613B2

(12) United States Patent
Castillo et al.

(10) Patent No.: US 10,010,613 B2
(45) Date of Patent: Jul. 3, 2018

(54) ANIONIC-CORE COMPOSITION FOR DELIVERY OF THERAPEUTIC AGENTS, AND METHODS OF MAKING AND USING THE SAME

(75) Inventors: Gerardo M. Castillo, Bothell, WA (US); Elijah M. Bolotin, Bothell, WA (US); Akiko Nashimoto-Ashfield, Seattle, WA (US)

(73) Assignee: PharmaIN Corporation, Bothell, WA (US)

( * ) Notice: Subject to any disclaimer, the term of this patent is extended or adjusted under 35 U.S.C. 154(b) by 412 days.

(21) Appl. No.: 13/395,090

(22) PCT Filed: Sep. 8, 2010

(86) PCT No.: PCT/US2010/048145

§ 371 (c)(1),
(2), (4) Date: Mar. 8, 2012

(87) PCT Pub. No.: WO2011/031771

PCT Pub. Date: Mar. 17, 2011

(65) Prior Publication Data

US 2012/0190097 A1 Jul. 26, 2012

Related U.S. Application Data

(60) Provisional application No. 61/240,857, filed on Sep. 9, 2009, provisional application No. 61/241,004, filed on Sep. 9, 2009.

(51) Int. Cl.

| | |
|---|---|
| ***C08B 37/08*** | (2006.01) |
| ***C07K 14/00*** | (2006.01) |
| ***C07K 7/00*** | (2006.01) |
| ***C07K 14/65*** | (2006.01) |
| ***A61K 47/34*** | (2017.01) |
| ***A61K 9/14*** | (2006.01) |
| ***A61K 47/58*** | (2017.01) |
| ***A61K 47/61*** | (2017.01) |
| ***A61K 47/64*** | (2017.01) |

(52) U.S. Cl.

CPC .............. *A61K 47/34* (2013.01); *A61K 9/146* (2013.01); *A61K 47/58* (2017.08); *A61K 47/61* (2017.08); *A61K 47/645* (2017.08)

(58) Field of Classification Search

CPC ..... A61K 9/06; A61K 47/48784; A61K 47/32
USPC ................................. 435/188, 200; 530/408
See application file for complete search history.

(56) References Cited

U.S. PATENT DOCUMENTS

| | | | | |
|---|---|---|---|---|
| 5,811,124 | A * | 9/1998 | Fernandez et al. | 424/489 |
| 2006/0239924 | A1 | 10/2006 | Bolotin | |
| 2006/0264353 | A1 | 11/2006 | Maxey et al. | |
| 2007/0141145 | A1 | 6/2007 | Castillo et al. | |
| 2007/0185033 | A1 | 8/2007 | Gefter et al. | |
| 2009/0053169 | A1 | 2/2009 | Castillo et al. | |
| 2009/0075902 | A1 | 3/2009 | Robbins et al. | |
| 2009/0156459 | A1 | 6/2009 | Castillo et al. | |
| 2009/0176892 | A1 | 7/2009 | Castillo et al. | |

FOREIGN PATENT DOCUMENTS

| | | | |
|---|---|---|---|
| KR | 10-2008-0092923 | A | 10/2008 |
| WO | 2007076371 | A2 | 7/2007 |
| WO | WO 2007/076371 | A2 | 7/2007 |

OTHER PUBLICATIONS

Chen et al Biomacromoecules, 2008, 9, 2447-2457.*
European search report and opinion dated Dec. 5, 2013 for EP Application No. 10816024.3.
Harada, et al. Novel polyion complex micelles entrapping enzyme molecules in the core: preparation of narrowly-distributed micelles from lysozyme and poly(ethylene glycol)-poly(aspartic acid) block copolymer in aqueous medium. Macromolecules, American Chemical Society. 1998; 31(27):288-294.
Lindgren, et al. Cell-penetrating peptides. Trends in Pharmacological Sciences. 2000; 21(3):99-103.
Morishita, et al. Elucidation of the mechanism of incorporation of insulin in controlled release systems based on complexation polymers. Journal of Controlled Release. 2002; 81(1-2):25-32.
Moriyama, et al. Hyaluronic acid grafted with ploy(ethylene glycol) as a novel peptide formulation. Journal of Controlled Release. 1999; 59:77-86.
Sipahigil, et al. Release behavior and biocompatibility of drug-loaded pH sensitive particles. International Journal of Pharmaceutics. 2006; 311(1-2):130-138.
Takacs-Novak, et al. Acid-base properties and proton-speciation of vancomycin. International Journal of Pharmaceutics. 1993; 89(3):261-263.
Yamaguchi, et al. Polysaccharide-poly(ethylene glycol) star copolymer as a scaffold for the production of bioactive hydrogels. Biomacromolecules, American Chemical Society. 2005; 6(4):1921-1930.
International search report and written opinion dated Dec. 17, 2010 for PCT Application No. US2010/048145.
Harada A. et al.: "Novel Polyion Complex Micelles Entrapping Enzyme Molecules in the Core: Preparation of Narrowly-Distributed Micelles from Lysozyme and Poly(ethylene Gycol)-Poly(aspartic Acid) Block Copolymer in Aqueous Medium," Macromolecules, American Chemical Society, Washington, D.C.; U.S., vol. 31, Jan. 27, 1998 (Jan. 27, 1998), pp. 288-294, XP002935122, ISSN: 0024-9297, DOI: 10.1021/MA971277V.

(Continued)

*Primary Examiner* — Tekchand Saidha
*Assistant Examiner* — Mohammad Y Meah
(74) *Attorney, Agent, or Firm* — Christensen O'Connor Johnson Kindness PLLC

(57) ABSTRACT

The present invention is directed to compositions comprising a polymer backbone with protective chain and anionic groups, and a cationic therapeutic agent. The present invention is directed to compositions for treating infections, inflammatory diseases, excess growth, and damaged cells and organs.

16 Claims, 1 Drawing Sheet

(56) References Cited

OTHER PUBLICATIONS

Lindgren M.M. et al.: "Cell-penetrating peptides," Trends in Pharmacological Sciences, Elsevier, Haywarth, GB, vol. 21, No. 3, Mar. 1, 2000, (Mar. 1, 2000), pp. 99-103, XP004202572, ISSN: 0165-6147, DOI: 10.1016/S0165-6147(00)01447-4.
Morishita M. et al.: "Elucidation of the mechanism of incorporation of insulin in controlled release systems based on complexation polymers," Journal of Controlled Release, Elsevier, Amsterdam, NL, vol. 81, No. 1-2, May 17, 2002 (May 17, 2002), pp. 25-32, XP004351100, ISSN: 0168-3659, DOI: 10.1016/S0168-3659(02)00019-6.
Moriyama K. et al.: "Hyaluronic acid grafted with poly(ethylene glycol) as a novel peptide formulation," Journal of Controlled Release, Elsevier, Amsterdam, NL, vol. 59, No. 1, May 1, 1999 (May 1, 1999), pp. 77-86, XP004166217, ISSN: 0168-3659, DOI: 10.1016/S0168-3659(98)00183-7.
Sipahigil O. et al.: "Release behaviour and biocompatibility of drug-loaded pH sensitive particles," International Journal of Pharmaceutics, Elsevier BV, NL, vol. 311, No. 1-2, Mar. 27, 2006 (Mar. 27, 2006), pp. 130-138, XP027972669, ISSN: 0378-5173.
Takacs-Novak K. et al.: "Acid-base properties and proton-speciation of vancomycin," International Journal of Pharmaceutics, Elsevier BV, NL, vol. 89, No. 3, Feb. 5, 1993 (Feb. 5, 1993), pp. 261-263, XP025557773, ISSN: 0378-5173, DOI: 10.1016/0378-5173(93)90252-B.
Yamaguchi N. et al.: "Polysaccharide-poly(ethylene glycol) star copolymer as a scaffold for the production of bioactive hydrogels," Biomacromolecules, American Chemical Society, U.S., vol. 6, No. 4, May 28, 2005 (May 28, 2005), pp. 1921-1930, XP002539059, ISSN: 1525-7797, DOI: 10.1021/BM050003.
European Examination Report, dated Feb. 15, 2017, for corresponding European Application No. 10816024.3, filed Sep. 8, 2010.
Nie,T.,et al. "Production of heparin-functionalized hydrogels for the development of responsive and controlled growth factor delivery systems," Journal of Controlled Release, 122:287-295, May 2007.
Chinese Office Action dated Nov. 15, 2017, issued in corresponding Chinese Application No. 201510670544.3, filed Sep. 8, 2010, 15 pages.
Chinese Search Report dated Nov. 15, 2017, issued in corresponding Chinese Application No. 201510670544.3, filed Sep. 8, 2010, 6 pages.

* cited by examiner

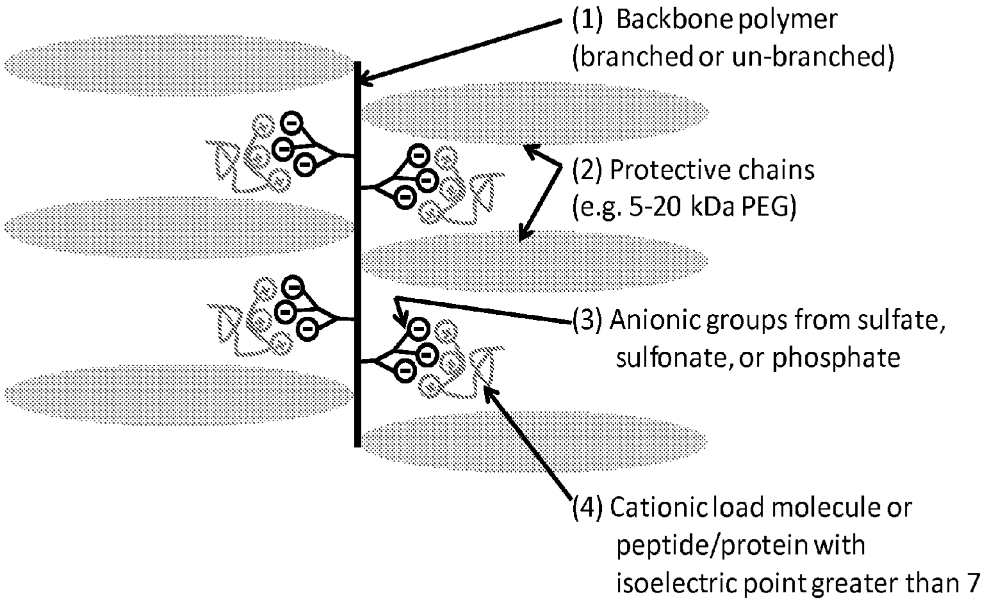
(1) Backbone polymer
(branched or un-branched)
(2) Protective chains
(e.g. 5-20 kDa PEG)
(3) Anionic groups from sulfate,
sulfonate, or phosphate
(4) Cationic load molecule or
peptide/protein with
isoelectric point greater than 7

SEQUENCE LISTING

```
<160> NUMBER OF SEQ ID NOS: 73

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Lys Lys Lys Lys Lys Lys Lys Gly Gly Thr Ala Leu Asp Trp Ser
1               5                   10                  15

Trp Leu Gln Thr Glu
            20


<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Arg Gln Ile Lys Ile Trp Phe Gln Asn Arg Arg Met Lys Trp Lys
1               5                   10                  15

Lys Thr Ala Leu Asp Trp Ser Trp Leu Gln Thr Glu
            20                  25


<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Arg Arg Arg Arg Arg Arg Gly Gly Thr Ala Leu Asp Trp Ser
1               5                   10                  15

Trp Leu Gln Thr Glu
            20


<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Gly Arg Lys Lys Arg Arg Gln Arg Arg Arg Gly Thr Thr Leu Asp
1               5                   10                  15

Trp Ser Trp Leu Gln Met Glu
            20


<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 5

Tyr Gly Arg Lys Lys Arg Arg Gln Arg Arg Arg Arg Pro Lys Arg Pro
1               5                   10                  15

Thr Thr Leu Asn Leu Phe
            20

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Arg Arg Arg Arg Arg Arg Arg Arg Pro Thr Thr Leu Asn Leu Phe
1               5                   10                  15

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Arg Gln Ile Lys Ile Trp Phe Gln Asn Arg Arg Met Lys Trp Lys
1               5                   10                  15

Lys Gln Leu Arg Arg Pro Ser Asp Arg Glu Leu Ser Glu
            20                  25

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Arg Arg Arg Arg Arg Arg Arg Gln Leu Arg Arg Pro Ser Asp Arg
1               5                   10                  15

Glu Leu Ser Glu
            20

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Arg Arg Arg Arg Arg Arg Val Gln Arg Lys Arg Gln Lys Leu
1               5                   10                  15

Met Pro

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

```
Arg Arg Arg Arg Arg Arg Arg Arg Asp Asp Arg His Asp Ser Gly Leu
1               5                   10                  15

Asp Ser Met Lys Asp Glu
            20
```

<210> SEQ ID NO 11
<211> LENGTH: 29
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Pyr

<400> SEQUENCE: 11

```
Xaa Glu Gly Ala Pro Pro Gln Gln Ser Ala Arg Arg Asp Arg Met Pro
1               5                   10                  15

Cys Arg Asn Phe Phe Trp Lys Thr Phe Ser Ser Cys Lys
            20                  25
```

<210> SEQ ID NO 12
<211> LENGTH: 23
<212> TYPE: PRT
<213> ORGANISM: Xenopus laevis

<400> SEQUENCE: 12

```
Gly Ile Gly Lys Phe Leu His Ser Ala Gly Lys Phe Gly Lys Ala Phe
1               5                   10                  15

Val Gly Glu Ile Met Lys Ser
            20
```

<210> SEQ ID NO 13
<211> LENGTH: 23
<212> TYPE: PRT
<213> ORGANISM: Xenopus laevis

<400> SEQUENCE: 13

```
Gly Ile Gly Lys Phe Leu His Ser Ala Lys Lys Phe Gly Lys Ala Phe
1               5                   10                  15

Val Gly Glu Ile Met Asn Ser
            20
```

<210> SEQ ID NO 14
<211> LENGTH: 37
<212> TYPE: PRT
<213> ORGANISM: Hyalophora cecropia

<400> SEQUENCE: 14

```
Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35
```

<210> SEQ ID NO 15
<211> LENGTH: 35
<212> TYPE: PRT
<213> ORGANISM: Hyalophora cecropia

<400> SEQUENCE: 15

Lys Trp Lys Val Phe Lys Lys Ile Glu Lys Met Gly Arg Asn Ile Arg
1 5 10 15

Asn Gly Ile Val Lys Ala Gly Pro Ala Ile Ala Val Leu Gly Glu Ala
20 25 30

Lys Ala Leu
35

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Ala Leu Tyr Lys Lys Leu Leu Lys Lys Leu Leu Lys Ser Ala Lys Lys
1 5 10 15

Leu Gly

<210> SEQ ID NO 17
<211> LENGTH: 12
<212> TYPE: PRT
<213> ORGANISM: Homo sapiens

<400> SEQUENCE: 17

Lys Phe His Glu Lys His His Ser His Arg Gly Tyr
1 5 10

<210> SEQ ID NO 18
<211> LENGTH: 24
<212> TYPE: PRT
<213> ORGANISM: Homo sapiens

<400> SEQUENCE: 18

Asp Ser His Ala Lys Arg His His Gly Tyr Lys Arg Lys Phe His Glu
1 5 10 15

Lys His His Ser His Arg Gly Tyr
20

<210> SEQ ID NO 19
<211> LENGTH: 32
<212> TYPE: PRT
<213> ORGANISM: Homo sapiens

<400> SEQUENCE: 19

Asp Ser His Ala Lys Arg His His Gly Tyr Lys Arg Lys Phe His Glu
1 5 10 15

Lys His His Ser His Arg Gly Tyr Arg Ser Asn Tyr Leu Tyr Asp Asn
20 25 30

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ala Lys Arg His His Gly Tyr Lys Arg Lys Phe His
1 5 10

<210> SEQ ID NO 21
<211> LENGTH: 30
<212> TYPE: PRT
<213> ORGANISM: Homo sapiens

<400> SEQUENCE: 21

```
Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30
```

<210> SEQ ID NO 22
<211> LENGTH: 18
<212> TYPE: PRT
<213> ORGANISM: Apis sp.

<400> SEQUENCE: 22

```
Gly Asn Asn Arg Pro Val Tyr Ile Pro Gln Pro Arg Pro Pro His Pro
1               5                   10                  15

Arg Ile
```

<210> SEQ ID NO 23
<211> LENGTH: 20
<212> TYPE: PRT
<213> ORGANISM: Pyrrhocoris apterus

<400> SEQUENCE: 23

```
Val Asp Lys Gly Ser Tyr Leu Pro Arg Pro Thr Pro Pro Arg Pro Ile
1               5                   10                  15

Tyr Asn Arg Asn
            20
```

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

```
Lys Leu Ala Lys Leu Ala Lys Lys Leu Ala Lys Leu Ala Lys
1               5                   10
```

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

```
Lys Leu Ala Lys Leu Ala Lys Lys Leu Ala Lys Leu Ala Lys Lys Leu
1               5                   10                  15

Ala Lys Leu Ala Lys
            20
```

<210> SEQ ID NO 26
<211> LENGTH: 37
<212> TYPE: PRT
<213> ORGANISM: Homo sapiens

<400> SEQUENCE: 26

```
Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35
```

<210> SEQ ID NO 27
<211> LENGTH: 35
<212> TYPE: PRT
<213> ORGANISM: Homo sapiens

<400> SEQUENCE: 27

```
Gly Asp Phe Phe Arg Lys Ser Lys Glu Lys Ile Gly Lys Glu Phe Lys
1               5                   10                  15

Arg Ile Val Gln Arg Ile Lys Asp Phe Leu Arg Asn Leu Val Pro Arg
            20                  25                  30

Thr Glu Ser
        35
```

<210> SEQ ID NO 28
<211> LENGTH: 31
<212> TYPE: PRT
<213> ORGANISM: Homo sapiens

<400> SEQUENCE: 28

```
Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg Thr Glu Ser
            20                  25                  30
```

<210> SEQ ID NO 29
<211> LENGTH: 18
<212> TYPE: PRT
<213> ORGANISM: Homo sapiens

<400> SEQUENCE: 29

```
Lys Leu Phe Lys Arg Ile Val Lys Arg Ile Leu Lys Phe Leu Arg Lys
1               5                   10                  15

Leu Val
```

<210> SEQ ID NO 30
<211> LENGTH: 26
<212> TYPE: PRT
<213> ORGANISM: Bos sp.

<400> SEQUENCE: 30

```
Gly Arg Phe Lys Arg Phe Arg Lys Lys Phe Lys Lys Leu Phe Lys Lys
1               5                   10                  15

Leu Ser Pro Val Ile Pro Leu Leu His Leu
            20                  25
```

<210> SEQ ID NO 31
<211> LENGTH: 39
<212> TYPE: PRT
<213> ORGANISM: Sus sp.

<400> SEQUENCE: 31

```
Arg Arg Arg Pro Arg Pro Pro Tyr Leu Pro Arg Pro Arg Pro Pro Pro
1               5                   10                  15
```

Phe Phe Pro Pro Arg Leu Pro Pro Arg Ile Pro Pro Gly Phe Pro Pro
20 25 30

Arg Phe Pro Pro Arg Phe Pro
35

<210> SEQ ID NO 32
<211> LENGTH: 26
<212> TYPE: PRT
<213> ORGANISM: Sus sp.

<400> SEQUENCE: 32

Arg Arg Arg Pro Arg Pro Pro Tyr Leu Pro Arg Pro Arg Pro Pro Pro
1 5 10 15

Phe Phe Pro Pro Arg Leu Pro Pro Arg Ile
20 25

<210> SEQ ID NO 33
<211> LENGTH: 19
<212> TYPE: PRT
<213> ORGANISM: Sus sp.

<400> SEQUENCE: 33

Arg Arg Arg Pro Arg Pro Pro Tyr Leu Pro Arg Pro Arg Pro Pro Pro
1 5 10 15

Phe Phe Pro

<210> SEQ ID NO 34
<211> LENGTH: 11
<212> TYPE: PRT
<213> ORGANISM: Sus sp.

<400> SEQUENCE: 34

Arg Arg Arg Pro Arg Pro Pro Tyr Leu Pro Arg
1 5 10

<210> SEQ ID NO 35
<211> LENGTH: 12
<212> TYPE: PRT
<213> ORGANISM: Sus sp.

<400> SEQUENCE: 35

Arg Leu Cys Arg Ile Val Val Ile Arg Val Cys Arg
1 5 10

<210> SEQ ID NO 36
<211> LENGTH: 18
<212> TYPE: PRT
<213> ORGANISM: Sus sp.

<400> SEQUENCE: 36

Arg Gly Gly Arg Leu Cys Tyr Cys Arg Arg Arg Phe Cys Val Cys Val
1 5 10 15

Gly Arg

<210> SEQ ID NO 37
<211> LENGTH: 17
<212> TYPE: PRT
<213> ORGANISM: Sus sp.

<400> SEQUENCE: 37

Arg Gly Gly Leu Cys Tyr Cys Arg Gly Arg Phe Cys Val Cys Val Gly
1 5 10 15

Arg

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Lys Lys Lys Lys Pro Leu Phe Gly Leu Phe Phe Gly Leu Phe
1 5 10

<210> SEQ ID NO 39
<211> LENGTH: 13
<212> TYPE: PRT
<213> ORGANISM: Bos sp.

<400> SEQUENCE: 39

Ile Leu Pro Trp Lys Trp Pro Trp Trp Pro Trp Arg Arg
1 5 10

<210> SEQ ID NO 40
<211> LENGTH: 13
<212> TYPE: PRT
<213> ORGANISM: Bos sp.

<400> SEQUENCE: 40

Ile Leu Pro Trp Lys Trp Pro Trp Trp Pro Trp Arg Arg
1 5 10

<210> SEQ ID NO 41
<211> LENGTH: 13
<212> TYPE: PRT
<213> ORGANISM: Bos sp.

<400> SEQUENCE: 41

Ile Leu Lys Lys Trp Pro Trp Trp Pro Trp Arg Arg Lys
1 5 10

<210> SEQ ID NO 42
<211> LENGTH: 13
<212> TYPE: PRT
<213> ORGANISM: Bos sp.

<400> SEQUENCE: 42

Ile Leu Lys Lys Trp Pro Trp Trp Pro Trp Arg Arg Lys
1 5 10

<210> SEQ ID NO 43
<211> LENGTH: 11
<212> TYPE: PRT
<213> ORGANISM: Homo sapiens

<400> SEQUENCE: 43

Gly Arg Arg Arg Arg Ser Val Gln Trp Cys Ala
1 5 10

<210> SEQ ID NO 44
<211> LENGTH: 18
<212> TYPE: PRT
<213> ORGANISM: Limulus polyphemus

<400> SEQUENCE: 44

Arg Arg Trp Cys Phe Arg Val Cys Tyr Arg Gly Phe Cys Tyr Arg Lys
1 5 10 15

Cys Arg

<210> SEQ ID NO 45
<211> LENGTH: 17
<212> TYPE: PRT
<213> ORGANISM: Tachypleus tridentatus

<400> SEQUENCE: 45

Lys Trp Cys Phe Arg Val Cys Tyr Arg Gly Ile Cys Tyr Arg Arg Cys
1 5 10 15

Arg

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Lys Arg Phe Lys
1

<210> SEQ ID NO 47
<211> LENGTH: 18
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(14)
<223> OTHER INFORMATION: Any amino acid and this region may encompass 0 to 10 residues
<220> FEATURE:
<221> NAME/KEY: MOD_RES
<222> LOCATION: (16)..(17)
<223> OTHER INFORMATION: Any amino acid

<400> SEQUENCE: 47

Lys Arg Phe Lys Xaa Xaa Xaa Xaa Xaa Xaa Xaa Xaa Xaa Xaa Trp Xaa
1 5 10 15

Xaa Trp

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Lys Arg Phe Lys Gln Asp Gly Gly Trp Ser His Trp Ser Pro Trp Ser
1 5 10 15

Ser

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Lys Arg Phe Lys Gln Asp Gly Gly Trp Ser His Trp Ser Pro
1 5 10

<210> SEQ ID NO 50
<211> LENGTH: 8
<212> TYPE: PRT
<213> ORGANISM: Unknown
<220> FEATURE:
<223> OTHER INFORMATION: Description of Unknown: bFGF inhibitor peptide

<400> SEQUENCE: 50

Lys Arg Thr Gly Gln Tyr Lys Leu
1 5

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Met Trp Tyr Arg Pro Asp Leu Asp Glu Arg Lys Gln Gln Lys Arg Glu
1 5 10 15

<210> SEQ ID NO 52
<211> LENGTH: 37
<212> TYPE: PRT
<213> ORGANISM: Leiurus quinquestriatus
<220> FEATURE:
<221> NAME/KEY: MOD_RES
<222> LOCATION: (1)..(1)
<223> OTHER INFORMATION: Pyr

<400> SEQUENCE: 52

Xaa Phe Thr Asn Val Ser Cys Thr Thr Ser Lys Glu Cys Trp Ser Val
1 5 10 15

Cys Gln Arg Leu His Asn Thr Ser Arg Gly Lys Cys Met Asn Lys Lys
20 25 30

Cys Arg Cys Tyr Ser
35

<210> SEQ ID NO 53
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Arg Gln Ile Lys Ile Trp Phe Gln Asn Arg Arg Met Lys Trp Lys Lys
1 5 10 15

Met Gly Gln Val Gly Arg Gln Leu Ala Ile Ile Gly Asp Asp Ile Asn
20 25 30

Arg Arg Tyr
35

<210> SEQ ID NO 54

<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: D-Lys
<220> FEATURE:
<221> NAME/KEY: MOD_RES
<222> LOCATION: (9)..(9)
<223> OTHER INFORMATION: D-Leu
<220> FEATURE:
<221> NAME/KEY: MOD_RES
<222> LOCATION: (10)..(10)
<223> OTHER INFORMATION: D-Ala
<220> FEATURE:
<221> NAME/KEY: MOD_RES
<222> LOCATION: (11)..(11)
<223> OTHER INFORMATION: D-Lys
<220> FEATURE:
<221> NAME/KEY: MOD_RES
<222> LOCATION: (12)..(12)
<223> OTHER INFORMATION: D-Leu
<220> FEATURE:
<221> NAME/KEY: MOD_RES
<222> LOCATION: (13)..(13)
<223> OTHER INFORMATION: D-Ala
<220> FEATURE:
<221> NAME/KEY: MOD_RES
<222> LOCATION: (14)..(15)
<223> OTHER INFORMATION: D-Lys
<220> FEATURE:
<221> NAME/KEY: MOD_RES
<222> LOCATION: (16)..(16)
<223> OTHER INFORMATION: D-Leu
<220> FEATURE:
<221> NAME/KEY: MOD_RES
<222> LOCATION: (17)..(17)
<223> OTHER INFORMATION: D-Ala
<220> FEATURE:
<221> NAME/KEY: MOD_RES
<222> LOCATION: (18)..(18)
<223> OTHER INFORMATION: D-Lys
<220> FEATURE:
<221> NAME/KEY: MOD_RES
<222> LOCATION: (19)..(19)
<223> OTHER INFORMATION: D-Leu
<220> FEATURE:
<221> NAME/KEY: MOD_RES
<222> LOCATION: (20)..(20)
<223> OTHER INFORMATION: D-Ala
<220> FEATURE:
<221> NAME/KEY: MOD_RES
<222> LOCATION: (21)..(21)
<223> OTHER INFORMATION: D-Lys

<400> SEQUENCE: 54

```
Cys Asn Gly Arg Cys Gly Gly Lys Leu Ala Lys Leu Ala Lys Lys Leu
1               5                   10                  15

Ala Lys Leu Ala Lys
            20
```

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Cys Asn Gly Arg Cys Gly Gly Lys Leu Ala Lys Leu Ala Lys Lys Leu
```

```
1               5                   10                  15

Ala Lys Leu Ala Lys
            20


<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Phe Cys Leu Gly Pro Cys Pro Tyr Ile Trp Ser Leu Asp Thr
1               5                   10


<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ser Leu Asp Ala Ser Ile Trp Ala Met Met Gln Asn Ala
1               5                   10


<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Arg Ile Trp Phe Ile Pro Arg Ser Ser Trp Tyr Glu Arg Ala
1               5                   10                  15


<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Ser Leu Asp Ala Thr Met Ile Trp Thr Met Met
1               5                   10


<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Ala Leu Asp Trp Ser Trp Leu Gln Thr Glu
1               5                   10


<210> SEQ ID NO 61
<211> LENGTH: 11
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 61

Thr Thr Leu Asp Trp Ser Trp Leu Gln Met Glu
1 5 10

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Arg Pro Thr Thr Leu Asn Leu Phe
1 5

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Gln Leu Arg Arg Pro Ser Asp Arg Glu Leu Ser Glu
1 5 10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Val Gln Arg Lys Arg Gln Lys Leu Met Pro
1 5 10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Asp Asp Arg His Asp Ser Gly Leu Asp Ser Met Lys Asp Glu
1 5 10

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 66

His His His His His His
1 5

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Lys Lys Lys Lys
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Lys Lys Lys Arg
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Lys Lys Arg Lys
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Lys Lys Arg Arg
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Lys Arg Arg Lys
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
peptide -continued

```
<400> SEQUENCE: 72

Lys Arg Arg Arg
1


<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Arg Arg Arg
1
```

ANIONIC-CORE COMPOSITION FOR DELIVERY OF THERAPEUTIC AGENTS, AND METHODS OF MAKING AND USING THE SAME

CROSS-REFERENCE

This application claims priority to U.S. Provisional Application 61/240,857 filed Sep. 9, 2009 and U.S. Provisional Application 61/241,004 filed Sep. 9, 2009.

GOVERNMENT LICENSE RIGHTS

This invention was made with government support under A1078539 and grant number DK084724, awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 26, 2012, is named 35221783.txt and is 21,022 bytes in size.

BACKGROUND OF THE INVENTION

The development of new drugs, formulations and other systems for administration of physiologically active peptides and proteins and other therapeutics and materials is driven by the need to provide these peptides or proteins or other materials to achieve the desirable physiological effects. With respect to peptides and proteins, many of them have been observed to be unstable in the gastro-intestinal tract and therefore may need to be stabilized or protected or delivered via systemic circulation. In addition, peptides and proteins that have low molecular masses tend to have short biological half-lives due to their efficient removal from systemic circulation via kidneys and reticuloendothelial system. Many peptides and proteins can also lose their activity in vivo due to proteolysis (peptide bond cleavage).

In part to circumvent these undesirable effects, a drug delivery system may be used. Drug delivery strategies have been developed for peptide and protein delivery in vivo, but most are not useful for sustained delivery. For example, the use of a continuous systemic infusion of drug via a pump is impractical for outpatients requiring high levels of mobility. Infusion has the associated disadvantages of quality of life and potential intravenous (i.v.) line infections. The use of an implantable pump, comprised of a capsule with a membrane allowing diffusion of a drug, is limited by the volume of the capsule. Peptides and proteins are often used in concentrated formulations in the capsules and aggregate, whereby losing specific activity. In many cases, the drug is released into the extracellular space and distributed in lymphatics. Other implantable biodegradable delivery systems are implanted or injected into the epidermis. The components of the system are usually slowly degraded as a result of biological activity of surrounding cells (i.e. as a result of the release of enzymes degrading chemical bonds that hold these implants together).

Proteins that have a net positive charge in their surface under physiological conditions and have basic (greater than pH 7.5) isoelectric point (pI) will benefit from the composition of the present invention. The use of basic proteins has much therapeutic potential, including uses in treating cancer and related neoplastic diseases, systemic infections, inflammations, and diseases of the nervous system such as Alzheimer's disease, Parkinson's disease, and prion diseases. There is a need for a biodegradable drug delivery carrier for the systemic delivery of basic (pI greater than pH 7.5) proteins and peptides that will provide longer circulation in the body, more stability in the blood, and can be more conveniently administered. In one embodiment of the present invention the anti-infective agent that benefits from the carrier of the present invention is lysostaphin with pI of 9.56. Most peptides and drugs that can potentially be useful in vivo in blocking specific intracellular mechanism requires basic moieties such as amino groups that allow membrane internalization. By attaching basic residues, these intracellular acting peptides and drugs can penetrate biological membranes. These basic residues are sometimes referred collectively as cell penetrating moiety or cell penetrating peptides (Cell-Penetrating Peptides by Ulo Langel, Pharmacology & Toxicology Series, 2002, CRC Press, New York).

SUMMARY OF THE INVENTION

In one aspect of the invention, a composition comprising a polymer backbone comprising monomeric units, a protective chain covalently linked to the polymer backbone, and anionic groups of carboxylate, sulfate, sulfonate, or phosphate covalently bonded to a monomeric unit of the polymer backbone, and a load molecule electrostatically linked to the anionic group directly without intermediary ions (such as metals) is provided. In one aspect, the sulfur and/or phosphorus atoms of anionic groups are more than one atom apart from each other to minimize chelating property. The load molecule may comprise: i) a cell penetrating peptide, ii) an anionic binding domain, or iii) an isoelectric point greater than 7.3. It is understood that electrostatic interaction of load molecule to the composition of the present invention is the main mode of interaction (Kd of 10 μM) and any trace hydrophobic interactions, when present, is weak (Kd>10 μM) and insignificant. For the purpose of this specification the term "anionic binding domain" is any portion of a molecule that has positively charged nitrogen atoms such that the molecules can bind carboxylate, sulfate, sulfonate, or phosphate moiety with dissociation constant of less than 10 μM. In a related aspect, a pharmaceutical composition comprising a polymer backbone comprising monomeric units, a protective chain covalently linked to the polymer backbone, and anionic groups of carboxylate, sulfate, sulfonate, or phosphate covalently bonded to a monomeric unit of the polymer backbone, and a load molecule electrostatically linked directly without intermediary ions (such as metals) to the anionic group is provided with a pharmaceutically acceptable excipient, wherein the sulfur and/or phosphorus atoms of anionic groups when present are more than one atom apart from each other, and wherein the load molecule comprises: i) a cell penetrating peptide, ii) an anionic binding domain, or iii) an isoelectric point greater than 7.3. It has been discovered that polymers containing chelating molecules can bind metal binding peptide/proteins in the absence of intermediary metals. Without wishing to be bound by theory, removal of the ability of chelating molecules to chelate metals by derivatization of the carboxyl groups with similarly negative but non-chelating moiety (such as sulfate, sulfonate, and phosphate) indicates that the ability to bind peptide and proteins is through ionic interactions.

These embodiments of the present invention, other embodiments, and their features and characteristics, will be apparent from the description, drawings and claims that follow.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Certain features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts an example of one of the anionic core compositions of the present invention. The invention depicted is a composition with polymeric backbone and a cationic load molecule or basic peptide/protein electrostatically bound directly to the anionic group of the carrier. This exemplary diagram depicts a polymeric backbone with: a) covalently linked and pendant protective chains, b) covalently linked and pendant anionic groups derived from carboxylate, sulfate, sulfonate, or phosphate groups, wherein anionic groups in turn electrostatically interacts directly (without intermediary ions) with cationic load molecule or basic peptide/protein (isoelectric point greater than 7 but preferably greater than 7.3 and more preferably greater than 7.5). This diagram is not to limit the compositions contemplated by the present invention.

DETAILED DESCRIPTION OF THE INVENTION

Definitions

For convenience, before further description of the present invention, certain terms employed in the specification, examples and appended claims which need further explanations are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used to refer to one or to more than one (i.e., to at least one) of the grammatical object of the article. By way of example, "an element" means one element or more than one element.

The term "basic protein" is a protein whose isoelectric point is basic (above 7) is called a "basic protein" while a protein whose isoelectric point is acidic (below 7) is called an "acidic protein". The solubility of proteins is lowest at the isoelectric point. Proteins have ionizable groups such as carboxyl groups and amino groups. Since the charge of these groups depends on pH, a protein molecule can have different charges according to pH. The number of negative charges is the same as the number of positive charges at a specific pH value and this pH is the isoelectric point, therefore, the electrostatic repulsion between similar proteins is smallest at this point and the solubility is also lowest. However, for example, at pH below isoelectric point either the amino groups will gain extra protons making the protein gain extra positive charges or the carboxyl groups will be protonated making the protein lose negative charges compared to the charge at isoelectric point. To determine whether the protonation of amino or the carboxyl groups is responsible for the changes in the property of the protein upon acidification depends on the starting isoelectric point pH. Acidification of basic protein, with isoelectric point above 8.0, towards neutral pH, the main group that will change will be the amino group. Further acidification below pH 7 will result in protonation of carboxyl group making them neutral and thus making the overall net charge of the protein more positive. All basic proteins will have more positive charges than negative charges at neutral pH making them able to bind to anionic carrier of the present invention at neutral pH. Because carboxyl groups can lose negative charge at pH between 5 and 7, the preferred anionic group of carrier of the present invention is the sulfate, sulfonate, and phosphate groups which require pH between 2 and 5 before they lose negative charges. Carboxyl groups will also be useful, however on occasions multiple carboxyl groups clustered together will tend to pick up positively charge metal ions making the overall net charge in the presence of metal closer to neutral or less anionic. The larger the number of anionic sites in the carrier the less likely it is that metals will interfere with their ability to bind positively charge load molecules.

The term "carrier" for the purpose of this invention refers to a composition of the present invention that comprises polymeric backbone with anionic moieties and a covalently-linked protective chain.

The term "backbone" for the purpose of this invention refers to the structure comprising a polymer (linear or branched).

The term "derivative" or "analog" as used herein includes compounds whose core structures are the same as, or closely resemble that of, a parent compound, but which have a chemical or physical modification, such as different or additional groups; the term includes co-polymers of parent compounds that can be linked to other atoms or molecules. The term also includes a peptide or protein with at least 50% sequence identity with the parent peptide or protein. The term also includes a peptide with additional groups attached to it, such as additional label or tag, compared to the parent peptide. The term also includes a polymer with additional group attached to it, such as alkoxy or methoxy group, compared to the parent polymer.

The "isoelectric point" (pI), sometimes abbreviated to IEP, is the pH at which a particular molecule or surface carries no net electrical charge. Amphoteric molecules called zwitterions contain both positive and negative charges depending on the functional groups present in the molecule. The net charge on the molecule is affected by pH of their surrounding environment and can become more positively or negatively charged due to the loss or gain of protons (H+). The pI is the pH value at which the molecule carries no electrical charge or the negative and positive charges are equal. Surfaces naturally charge to form a double layer. In the common case when the surface charge-determining ions are H+/OH—, the net surface charge is affected by the pH of the liquid in which the solid is submerged. Again, the pI is the pH value of the solution at which the surfaces carries no net charge. The pI value can affect the solubility of a molecule at a given pH. Such molecules have minimum solubility in water or salt solutions at the pH which corresponds to their pI and often precipitate out of solution. Biological amphoteric molecules such as proteins contain both acidic and basic functional groups. Amino acids which make up proteins may be positive, negative, neutral or polar in nature, and together give a protein its overall charge. At a pH below their pI, proteins carry a net positive charge; above their pI they carry a net negative charge. Proteins can thus be separated according to their isoelectric point (overall charge) on a polyacrylamide gel using a technique called isoelectric focusing, which uses a pH gradient to separate proteins. Isoelectric focusing is also the first step in 2-D gel polyacrylamide gel electrophoresis. For an amino acid with only one amine and one carboxyl group, the pI can be calculated from the pKa's of this molecule using a formula: $pI=\{\{pK_1+pK_2\}/2\}$. For amino acids with more than two ionizable groups, such as lysine, the same formula is used, but this time the two pKa's used are those of the two groups that lose and gain a charge from the neutral form of the amino acid. Lysine has a single carboxylic pKa and two amine pKa values (one of which is on the R-group), so fully protonated lysine has a +2 net charge. To get a neutral charge, one may deprotonate the lysine twice, and therefore use the R-group and amine pKa values (found at List of standard amino acids): $pI=\{\{9.06+10.54\}/2\}=9.80$. In a polypeptide, the alpha amino and carboxyl groups are not ionizable and thus not calculated except at the terminal. In this case only the R-groups (mainly lysine, arginine, aspartate, and glutamate) are the most relevant in pI calculation. The pH of an electrophoretic gel is determined by the buffer used for that gel. If the pH of the buffer is above the pI of the protein being run, the protein will migrate to the positive pole (negative charge is attracted to a positive pole). If the pH of the buffer is below the pI of the protein being run, the protein will migrate to the negative pole). If the protein is run with a buffer pH that is equal to the pI, it will not migrate at all. This is also true for individual amino acids. For the purpose of the present invention, the pI above 7 are called basic protein, but the most preferred pI for the load molecule of the present invention is above physiological pH of 7.3 since these load molecules have a net positive charge at physiological pH. It should be emphasized that for a large load molecule such as protein, basic pI is not the only requirement for loading into the carrier as the existence of patches of positively charged surface is sufficient to allow a strong electrostatic interaction with the carrier.

The term "load molecule" is the active agent, therapeutic agent or imaging agent intended to be delivered by the anionic-core composition or the carrier of the present invention to the subject. The load molecule is intended to be electrostatically bound directly to the anionic groups of the carrier but not covalently linked to the carrier. The load molecule can be peptide or protein containing positively charge amino groups at neutral pH. Active agent also includes a small positively charged organic molecule.

The term "naturally-occurring" or "native", as applied to an object, refers to the fact that an object may be found in nature. For example, a backbone that may be isolated from a source in nature and which has not been intentionally modified, for example, in the laboratory, is naturally-occurring. The term "non-naturally-occurring" or "non-native" or "synthetic" is as applied to an object that has been intentionally modified for example, in the laboratory, and not normally found in nature.

The term "polymer" is a molecule (or macromolecule) composed of repeating structural units connected by covalent chemical bonds. This term includes polyamino acids, (with repeating amino acids; note that for the purpose of the present specification, proteins does not have repeating amino acids as their amino acids varies along the chain) polyallylamine, polyacrylic acid, polyethyleneimine, polysaccharides and other polymeric backbone mentioned in the instant specification. For the purpose of clarity of the instant specification, the term "polymer backbone" or "backbone polymer" is a non-proteinaceous polymer. Proteinaceous means naturally occurring proteins or their derivatives which is not a homopolymer and has enzymatic or biological activity caused by its three dimensional conformation. Polyamino acid homopolymer such as polylysine is non-proteinaceous.

A "patient," "subject" or "host" to be treated with the composition of the present invention may mean either a human or non-human animal. The term "mammal" is known in the art, and exemplary mammals include humans, primates, bovines, porcines, canines, felines, and rodents (e.g., mice and rats).

The term "peptide/protein" means peptide or protein where peptide has 50 or less amino acids and protein has more than 50 amino acids and may be isolated from cells or synthetically prepared. Derivatives and fragments may also be isolated or synthetically prepared. Ideally, the peptide/protein load molecule of the present invention will have isoelectric point above pH 7. It is possible, however, that certain derivatives of a peptide/protein active agent may have patches of positively charge groups despite having an acidic isoelectric point allowing interaction of this type of peptide protein with the anionic groups of the carrier. This type of load molecule is intended to be covered by the present invention. An active agent derivative can be generated by truncation of the aminoacid sequence or addition of other amino acids or functional groups.

General Introduction

Embodiments of the present invention are directed at carrier-based basic protein delivery systems comprising a backbone, an anionic domain covalently linked to the backbone, and a basic protein ionically bonded or electrostatically bonded to the anionic domain of the carrier. Optionally, the backbone can contain multiple polyethylene glycol chains to shield or protect the basic protein. Protective polyethylene glycol chains can increase the overall hydrodynamic radius of the macromolecular agent which can result in prolonged circulation in the blood (by not allowing elimination/filtration through the kidney) and increase retention/accumulation at sites of high vascular permeability.

The carriers of the present invention permeate broken down or abnormal vascular barriers with increased permeability but because of the carrier size and direction of flow/pressure, carrier is not able to flow back in the circulation. This results in carrier accumulation at sites of abnormal vascular barriers. This was demonstrated in a model of bacterial inflammation of the muscle tissue in rats induced with *E. coli*. Alternatively, the carrier could be used for early detection of leakage into the extra vascular space and specific targeting to the sites with increased vascular permeability, such as inflammation. Thus, increased accumulation of the carrier at sites of inflammation will allow the carrier-associated-basic protein to accumulate at sites of infection.

The association of a basic protein or a derivate thereof to the backbone is accomplished using an ionic interaction. The use of modified protein or protein derivatized by adding basic amino acid residues can maintain or enhance ionic-interaction. An advantage of anionic groups in the carriers of the present invention is to afford reversible binding of basic proteins which are capable of forming ionic bonds to the anionic moiety of the carrier. The ionic bonding affords reversible dissociation of basic proteins/peptides and drugs from the backbone containing the anionic functional groups.

The carrier-anionic moiety-basic protein formulation can provide several benefits. For example such formulations afford better biocompatibility; decrease potential toxicity; decrease immunogenicity; increase blood residence time; enable site-specific accumulation at sites of inflammation. The carriers of the present invention have high drug loading capacity as well, with its specific reversible binding of an exemplary basic protein, lysostaphin (Ex. 44).

Based on results presented, basic proteins bind to the chelating moiety in the absence of metal. Interactions may also possibly be facilitated by interactions with protective chains and/or other components of the carrier. The design of the carriers of the present invention is made in such a way that the ionically associated basic protein is protected by the protective chains (for example polyethylene glycol chains) from for example peptidases and antibodies. In addition, the association of basic proteins (such as lysostaphin) and peptides (such as those presented in Table 1 and their analogs or derivatives) with the high molecular weight carrier can prolong in vivo half life by preventing excretion via renal ultrafiltration, uptake by antigen presenting cells, and uptake by reticuloendothelial system.

Elements of the Carrier of the Invention and Basic Proteins

The carriers of the present invention are comprised of: a backbone that may be polymers/copolymers capable of supporting multiple anionic groups derived from carboxyl, sulfate, sulfonate, or phosphate groups which can bind (by ionic interaction) positively charged nitrogen in an active agent or therapeutic molecule (or load molecule). In further embodiments of the present invention, the backbone further comprises a protective chain covalently linked to the backbone. In one aspect, the carrier is biocompatible. The individual components are described below.

a. Backbones

The backbones of the carriers of the present invention can be polymers and co-polymers of linear or branched structure or conjugates thereof. The backbone molecular weight ranges from 1,000 Da to 200,000 Da. In some embodiments the backbone molecular weight may range from 1,500 Da to 100,000 Da, or from 2,000 Da-50,000 Da, or from 2,000 Da-30,000 Da, or from 2,000 Da-25,000 Da. It is preferable that the polymeric backbone is derived from naturally occurring polymer. It is also preferable that the polymeric backbone is water soluble.

1) Polymeric or Co-Polymeric Backbones:

Polymers are composed of repeating structural units connected by covalent chemical bonds. A co-polymer is a polymer derived from two or more different polymers linked together.

In certain embodiments, the backbone polymers or backbone co-polymers of the subject compositions have molecular weights ranging from about 500 to 5,000, 10,000, 15,000, 20,000, 25,000, 30,000, 40,000, or 50,000, 60,000, 70,000, 80,000, 90,000, or 100,000 Daltons and even more specifically between 2,000 to 50,000 Daltons. The number-average molecular weights (Mn) may also vary widely, but generally fall in the range of about 1,000 to about 120,000 Daltons or even from about 2,000 to about 70,000 Daltons or even from about 3,000 to about 50,000 Daltons. In certain embodiments, the Mn varies between about 5,000 and 45,000 Daltons. Within a given sample of a subject polymeric backbone, a wide range of molecular weights may be present. For example, molecules within the sample may have molecular weights which differ by a factor of 2, 5, 10, 20, 50, 100, or more, or which differ from the average molecular weight by a factor of 2, 5, 10, 20, 50, 100, or more. The number of monomers in the backbone polymer may vary from 10 (a 10-mer) to 1,000 (a 1,000-mer). The backbone polymer may alternatively be about a 25, 50, 100, 150, 200, 250, 300, 350, 400, or 450-mer, and even more specifically between a 100-mer to 250-mer. The number of monomers in the polymeric backbone generally determines the number of functional groups that can be modified to carry anionic moieties or protective chains. The preferred size of the polymeric backbones is selected so that the overall hydrodynamic diameter of the carrier molecule (backbone, anionic groups, and protective chains) prior to loading with basic load molecule is below 100 nm.

In some embodiments, the polymeric backbone is a non-proteinaceous homo- or heteropolymer with repeating monomeric groups containing amino, carboxyl, hydroxyl, and thiol groups and may be of natural or synthetic origin, wherein the repeating monomeric groups can be covalently modified to further contain anionic groups or more anionic groups such as carboxylate, sulfate, sulfonate, or phosphate moieties and hydrophilic protective chains. The sulfate, sulfonate, or phosphate may be linked to the polymer directly or using spacer with multiple carboxyl groups, such as diethylenetriaminepentaacetic acid (DTPA), ethylenediaminetetraacetic acid (DTPA), nitrilotriacetic acid (NTA), ethyleneglycoltetraacetic acid (EGTA), or citric acid to name a few, that will allow convenient attachment and/or clustering of anionic charges as a single pendant to the polymer backbone (not part of the backbone that is important for the molecular integrity of the backbone). The backbone may be modified to carry one or more pendant anionic groups. In other embodiments the polymeric backbone may also be a non-proteinaceous homo- or heteropolymer with repeating hydrophobic groups with terminal amino, carboxyl, hydroxyl, and thiol groups or any modifiable functional groups that can be covalently modified to further contain a cluster (two or more) of anionic groups such as carboxylate, sulfate, sulfonate, or phosphate moieties and hydrophilic protective chains. The term "non-proteinaceous polyamino acid" as used herein includes a polyaminoacid that is not naturally made by a living organism unless recombinantly engineered or does not have enzymatic or biological activity resulting from its three dimensional conformation. In certain embodiments, the polymeric backbone is a polyamino acid which may have D- or L-chirality or both and is a straight chain homopolymer. In one specific embodiment, straight chain homopolymers include polylysine, polyornithine, polyarginine, polyglutamate, polyaspartate, polyserine, polytyrosine, or any other amide linked homopolymer made from amino acids. In another preferred embodiment, straight chain hydrophobic homopolymers comprise polyalanine, polyvaline, polyleucine, polyisoleucine, polyglycine, or polyphenylalanine. These hydrophobic polyamino acids can be modified at one terminal to contain cluster (2 or more) of anionic groups such as carboxylate, sulfate, sulfonate, or phosphate, or combination thereof and at the other terminal to contain hydrophilic protective chains. If the backbone is a polymer comprising polyamino acids, it is usually non-proteinaceous, meaning that it is not a naturally occurring protein with activity associated with its three dimensional conformation. The polymeric backbone may have a molecular weight of about 600-1,000,000 daltons, including the range of about 1,000-70,000 Daltons. Other polymeric backbones with repeating modifiable functional groups may also be used such as those with repeating sulfhydryl (thiol), amino, carboxyl, and hydroxyl groups. Carbohydrate polymers from biological source and other synthetic polymers where monomers are non-biological may also be used as the polymeric backbone. The polymeric backbone provides multiple sites from where the anionic groups and hydrophilic protective chains can be attached. The backbone includes those with carboxylate, sulfate, sulfonate or phosphate already present and such that after covalent attachment of hydrophilic protective chains such as polyethylene glycol or derivatives, no further modification may be needed. These include sulfated polysaccharides such as chondroitin sulfate, heparan sulfate, dermatan sulfate, heparin sulfate, dextran sulfate, fucoidan, and carrageenan as example. These backbones can be modified to contain hydrophilic protective chains to obtain the carrier component of the present invention from which the basic load molecule can be ionically attached to complete a composition of the present invention. As further embodiment of the composition where the backbone already contain sulfate, sulfonate, or phosphate groups, backbone may further be modified to contain additional sulfate, sulfonate or phosphate groups to increase the anionic charge density of the composition of the present invention to further enhance its ability to bind basic load molecule (those with isoelectric point above 7).

Polymeric backbones can include polysaccharides. Polysaccharides encompass disaccharides, oligosaccharides and larger polymers up to millions of Daltons. Polymeric backbones include polysaccharides, oligosaccharides and products chemically derived thereof, bearing modifiable carboxylic groups, alcohol groups or amino groups, which may be exemplified by: polyxylotol, galacturonic acid, glucuronic acid, mannuronic acid, hyaluronic acid, pectic acid, neuraminic acid, alginic acid, carrageenan; oxidized dextrans; aminated dextran, e.g. containing linked aminogroups. Polymeric backbones including polysaccharides may be linear or branched, may be carboxylated, carboxymethylated, sulfated or phosphorylated. Polymeric backbones including polysaccharides can be reacted with derivatives of carbonic, dicarbonic, sulfuric, aminosulfuric, phosphoric acids with resultant linking of carboxylic, aminocarboxylic, carboxymethyl, sulfuric, amino or phosphate groups. Polymeric backbones including polysaccharides can be obtained by chemical alteration of dextran, mannan, xylan, pullulan, cellulose, chytosan, agarose, fucoidan, galactan, arabinan, fructan, fucan, chitin, pustulan, levan or pectin. In addition these polysaccharides may be represented by heteropolymers or homopolymers of monosaccharides such as but not limited to glucose, galactose, mannose, galactose, deoxyglucose, ribose, deoxyribose, arabinose, fucose, xylose, xylulose, and ribulose.

Polymeric backbones also include polymers (linear or branched) such as polyethyleneimine, polyamidoamine, polyallylamine, polyacrylic acid; polyalcohols (e.g. polyvinylalcohol) to which carboxylic, amino or alcohol groups are chemically linked and/or available for attachment of more anionic groups. These polymeric backbones can be non-biological to which carboxylic, amino, or alcohol groups are available for attachment of more anionic groups. Polymeric backbone may contain anionic groups and further modification may be done to increase the number of anionic groups or to enhance the quality of anionic groups such as converting carboxyl groups to sulfate, sulfonate or phosphate groups.

In another embodiment, the polymer acting as the polymeric backbone may be poly(ethylene glycol) (PEG) with functional groups at the terminal end or near the terminal end making up the cluster (2 or more) of anionic groups to which the basic protein can bind. Schematically this embodiment may be represented by the following: PEG-anionic groups*basic protein, where the asterisk represents ionic interaction which is a very specific relationship among elements of the present invention. Alternatively, PEG may be functionalized along its backbone allowing anionic cluster to be pendant to the backbone from which basic protein can associate by direct electrostatic interaction. This structure may also allow pendant protective chains as well.

b) Anionic Moieties or Anionic Groups

Examples of anionic groups that can be chemically linked the backbone include: -phosphate; -sulfate; -sulfonate; and -carboxyl. The binding between the amino groups in protein and the carboxyl groups is not as strong as with anionic groups such as phosphate, sulfate, and sulfonate. This is because the carboxyl group has pKa of around 6, whereas the sulfate, sulfonate, and phosphate have pKa of less than 3. This makes the population of sulfate, sulfonate, and phosphate mainly negatively charged at pH above 3. The carboxyl group population will be mainly negatively charge at pH 6 and above which gives it some limitation from forming anion under mildly acidic condition. In addition, most of the polycarboxyl containing moieties are capable of chelation which can disturb the metal requiring physiological function of load molecule or blood proteins. The preferred anionic groups are phosphate, sulfate, and sulfonate. However this is not to exclude carboxyl groups from various embodiment of the present invention. The anionic groups in the present composition can be located in a cluster. The anionic cluster is defined for the purpose of this specification as two or more anionic groups attached to the backbone by a common covalent bond and that each anionic charge is not further from the other anionic charge by more than 12 atoms. Anionic groups are derived from carboxylate, sulfate, sulfonate, and/or phosphate. It is preferable that the sulfur or phosphorus atoms making up the anionic charges are separated from each other by more than three atoms to prevent them from being a strong chelator of metals. Once metal is chelated, the metal will add positive charge in the anionic site or cluster making it less able to bind cationic or positively charged load molecules with isoelectric point greater than 7. In one embodiment, metal is excluded, as it can potentially create a strong co-ordination interaction that would not allow calibrated release of the load molecule. The greater separation between the sulfur and/or phosphorus atom in anionic cluster may assist in reducing or weakening the chelating properties of the anionic cluster of the carrier. In this manner the release of the load molecules can be facilitated with physiological salt. Furthermore, chelation can also inactivate load molecules containing metals or calcium such as Factor VIII, in addition to neutralizing the anionic property of the carrier. This is especially true with phosphate in a form of bisphosphonate in which the phosphorus atom is separated by only one atom or the charges are separated by 3 atoms. Because of this, bisphosphonate is a strong chelator of metal which can inactivate biological molecules containing transition metals or alkaline earth metals such as calcium. Sulfur and phosphorus atoms forming anionic groups in the composition of the present invention are separated by more than one atom making them weak-chelator. This is accomplished by the use of polycarboxyl amine spacer, which then holds several strong anionic groups containing sulfur and/or phosphorus atoms. In an embodiment of the invention, the organizational relationship of cationic load molecule to the anionic group is by direct ionic interaction and is not mediated by any other divalent metal ions. Such organizational relationship distinguishes the present invention from other polymeric compositions that use metal bridges to attached load molecules. Further, the present invention does not rely on hydrophobic interactions to attach load molecules since load molecules that are positively charged or have an isoelectric point above 7.3 are water soluble and unlikely to be very hydrophobic. Such highly charged load molecules of the present invention repel hydrophobic groups as known in the art. Load molecules of the present invention are limited to those load molecules that does not interact with hydrophobic groups significantly (those with Kd for hydrophobic groups of greater than 50 μM). A cluster of carboxyl groups separated by 4 or more atoms will also be less of a strong chelator or even non-chelating and can be used as the anionic cluster of the present invention. For the purpose of the instant specification, anionic group or a cluster of anionic groups pendant to the backbone through a single chemical bond is no more than 1,500 Da in molecular mass excluding the backbone mass. This is to facilitate shielding by protective chains in which the preferred mass is between 2,000 Da and 20,000 Da.

c) Protective Chains

Examples of protective chains (interchangeably referred to as protective side chains or hydrophilic protective chains) include poly(ethylene glycol), which may be esterified by dicarboxylic acid to form a poly(ethylene glycol) monoester; methoxy poly(ethylene glycol) monoester (MPEG) or a co-polymer of poly(ethylene glycol) and poly(propylene glycol) monoester in a form of an ester with a dicarboxylic acid giving the terminal of this co-polymers a carboxyl group that can be used to covalently link it to a backbone (see above). Other forms include poly(ethylene glycol)-carboxyl; methoxy poly(ethylene glycol)-carboxyl; poly (ethylene glycol)-carboxymethyl; methoxy poly(ethylene glycol)-carboxymethyl; poly(ethylene glycol) monoamine; methoxy poly(ethylene glycol) monoamine; poly(ethylene glycol) hydrazide; methoxy poly(ethylene glycol) hydrazide; methoxy poly(ethylene glycol) imidazolide block-co-polymer of poly (ethylene glycol) and one or several polymers represented by polyaminoacid, polysaccharide, polyamidoamine, polyethyleneimine where these blocks are alternated to give a linear block-co-polymer. In one embodiment, the overall molecular weight of a protective chain may be larger than 300 Daltons but not exceeding 10,000 Daltons. In one embodiment, one or more protective chains are linked to the polymeric backbone by a single linkage.

In one example provided herein, a composition of the present invention comprises a linear polymeric backbone with a degree of polymerization in the range of 2-10,000 to which independently and covalently linked are methoxy-polyethylene glycol (mPEG) protective chains with a mass of 300-25,000 Daltons and anionic groups (which may be from sulfate, sulfonate or phosphate but does not exclude carboxyl groups as the anionic groups) where said protective chains and anionic groups are independently linked or pendant to the backbone. In another example, the degree of polymerization of the polymeric backbone is in the range of 25-1,000. In still another example, the degree polymerization of polymeric backbone is in the range of 50 to 300.

d) Active Agents: Basic Proteins and Peptides

1) Proteins:

Basic proteins and peptides are art-recognized as proteins and peptides with isoelectric point greater than 7. Basic proteins include metalloexopeptidases such as lysostaphin which is an anti-infective agent. The carriers of the present invention can bind essential majority of basic proteins or the basic protein active agents and derivatives, fragments, and analogs thereof so long as they remain basic or their isoelectric point remains above 7. Basic proteins and their derivatives, fragments and analogs may be produced by recombinant techniques from DNA constructs. Those proteins with isoelectric point below 7 can be made to have isoelectric point greater than 7, by adding basic amino acids in the sequence either by using DNA recombinant techniques or during synthesis. The basic amino acids are lysine and arginine. Peptides can be made basic during synthesis by adding basic amino acid at their terminal while maintaining the bioactivity of the main sequence. Alternatively, the basic sequence can be added such that once release in the blood or enters the cell, the basic sequence can be cleaved by an endogenous (naturally present in the body of an organism) protease releasing the active peptides. The basic protein active agents of the present invention may or may not be recombinant products. The basic protein active agents of the present invention may be product of recombinant production in mammalian cells that may or may not involved the DNA sequence modification that prevents glycosylation. The basic protein active agents of the present invention may be native version purified from organism that naturally produces the basic protein. The basic protein active agents of the present invention may be purified from an organism. For example, lysostaphin, an exemplary basic protein, can be purified from organism that naturally produces it, such as *Staphylococcus simulans* or *Staphylococcus staphylolyticus*. The carriers of the present invention can bind to basic proteins as well as analogs, derivatives, and fragments thereof.

Carriers of the present invention can bind basic proteins and analogs, derivatives, and fragments thereof. In specific embodiments carriers of the present invention bind lysostaphin. Lysostaphin is art-recognized and is bacteriolytic for *Staphylococcus aureus*. This includes derivatives and fragments of lysostaphin that have substantially the same biological effect as naturally occurring lysostaphin. The lysostaphin may be isolated or synthetically prepared. Derivatives and fragments may also be isolated or synthetically prepared. It is possible that certain derivatives of lysostaphin may have different isoelectric point or even have isoelectric point below 7, but as long as there is a cluster of positive charges in a protein far away from negative charges, the protein can potentially bind to the anionic group of the carrier of the present invention. To determine whether the interaction of lysostaphin to the carrier is direct anionic-cationic interaction and not through intermediary multivalent metal ion is by adding 0.4M NaCl. Anionic-cationic interaction can be disrupted by 0.4 M NaCl whereas the interaction mediated by multivalent metal ion through coordinate bonding cannot be disrupted by 0.4M NaCl (see example below). In one embodiment, a derivate of lysostaphin can be generated by truncation of the amino acid sequence or addition of other amino acids or functional groups such as basic amino groups. In one embodiment lysostaphin (including its analogs, derivatives and fragments) comprises a total basic amino acids (lysine and arginine) greater than the total acidic amino acids (glutamate and aspartate), thus giving the protein a net positive charge capable of binding anionic-core carrier of the present invention. Occasionally, a protein or peptide with isoelectric point below 7 may have all the basic amino acids in one end of the molecule and all the acidic amino acids in the other end of the molecule or alternatively the protein or peptide may fold in such a way that acidic amino acid is buried and the basic amino acids are exposed. Under this circumstance it can still bind the anionic carrier of the present invention so long as the basic amino acids are in spatially separate region of the molecule. The determination of whether a protein or a peptide with isoelectric point below 7 will interact with the carrier of the present composition will need to be determined on a case by case basis using method described here and which can easily be performed by a person skilled in the art without undue experimentations. Lysostaphin naturally has an isoelectric point between pH 9-10, allowing it to bind tightly to the carrier of the present invention. Lysostaphin, therefore, supplies positively charged amino groups such that there is no need to modify it synthetically to contain basic amino acids. Lysostaphin may be loaded to the carrier of the present invention by mixing a carrier solution with a lysostaphin solution at temperature between 15 to 37 degrees Celsius. The loaded carrier can be lyophilized and reconstituted prior to use. The lysostaphin of the present invention or basic proteins in general can be further modified to contain more basic amino acids to enhance binding to the carriers of the present invention.

Lysostaphin, one of the active agents of the present invention, is a peptidase enzyme produced by certain strains of *Staphylococcus* microorganisms with antibacterial activity against staphylococci. Lysostaphin is a 25-kDa peptidase produced by *Staphylococcus simulans* which cleaves a glycine-glycine bond unique to an inter-peptide cross-bridge of the *Staphylococcus aureus* cell wall with EC number designation of EC 3.4.24.75. Lysostaphin is an exemplary basic protein, more specifically a glycyl-glycyl basic protein.

2) Peptides:

Among intracellular acting peptides are peptides that can modify signal transduction pathways. In order for the peptides to modify signal transduction pathways, they may be required to penetrate cell membranes. The ability of peptides to penetrate cell membrane depends on the number of basic amino acids in close proximity with each other. These basic amino acids in close proximity with each other are termed peptide transduction domain or cell penetrating peptides (Cell-Penetrating Peptides by Ulo Langel, Pharmacology & Toxicology Series, 2002, CRC Press, New York). All these peptides and their derivatives are ideal load molecules for the anionic core carrier of the present invention. In general all peptides (polypeptides with 50 or less amino acids) containing peptide transduction domain or cell penetrating sequence can be delivered using the carrier of the present invention. The peptide transduction domain or cell penetrating peptide sequence is characterized by the presence of a sequence of 5-10 amino acids with at least 2 basic amino acids (lysine and/or arginine) more than the number of acidic amino acids (glutamate and aspartate). Some examples of these are all listed in a book entitled Cell-Penetrating Peptides by Ulo Langel, Pharmacology & Toxicology Series, 2002, CRC Press, New York, which is hereby incorporated by reference. It should be noted that in all cases the cell penetrating peptide follows the same general rule that it contains 5-10 amino acids with at least 2 basic amino acids (lysine and/or arginine) more than the number of acidic amino acids (glutamate and aspartate). Unfortunately all these peptides are degraded and eliminated by kidney very quickly once in the circulation requiring administration of large amount of this peptide (10 mg/Kg in mice). These peptides will benefit significantly from the carrier of the present invention. Because all these intracellular acting peptides with cationic cell penetrating sequence will have basic sequences, they will all be ideal load molecules for the anionic core composition of the present invention. The carrier will increase the blood circulation half-life of this peptides and accumulate or target the peptide to site of inflammation which is present in diseases such as rheumatoid arthritis, chronic inflammatory bowel disease, Crohn's disease, ulcerative colitis, atherosclerosis, and diabetes among others.

a) Anti-Inflammatory Peptides and Proteins.

In one embodiment, the peptides/proteins of the present invention are useful in the treatment of inflammation may be a peptide that blocks NFkB action and contains a cell penetrating sequence. Examples of chronic inflammatory diseases that can benefit from the composition of the present invention are: rheumatoid arthritis, chronic inflammatory bowel disease, Crohn' disease, ulcerative colitis, and diabetes. The cell penetrating peptide sequence is a peptide containing a series of basic amino acids (such as lysine or arginine) that allows penetration inside the cell. This sequence can be attached to a sequence that can suppress NFkB activation and thus preventing inflammation. Examples: (SEQ ID NO: 60) Basic-peptide-Thr-Ala-Leu-Asp-Trp-Ser-Trp-Leu-Gln-Thr-Glu-OH or (SEQ ID NO: 61) Basic-peptide-Thr-Thr-Leu-Asp-Trp-Ser-Trp-Leu-Gln-Met-Glu-OH. Specific example of this type of peptide has sequence of (SEQ ID NO:1) $(Lys)_8$-Gly-Gly-Thr-Ala-Leu-Asp-Trp-Ser-Trp-Leu-Gln-Thr-Glu (or KKKKKKKK-GG-TALDWSWLQTE: from Dave S., et. al., 2007, Journal of Immunology, vol 179, p 7852-7859). Alternative to this sequence is (SEQ ID NO:2) H-Asp-Arg-Gln-Ile-Lys-Ile-Trp-Phe-Gln-Asn-Arg-Arg-Met-Lys-Trp-Lys-Lys-Thr-Ala-Leu-Asp-Trp-Ser-Trp-Leu-Gln-Thr-Glu-OH (or DRQIKIWFQNRRMKWKK-TALDWSWLQTE: from Shibata, W., et al. 2007. Journal of Immunology, vol 179, p 2681-2685; Jimi, E., et al. 2004. *Nat. Med.,* 10, 617; Siegmund, D., et al. 2001. *J. Biol. Chem.* 276, 43708. May, M. J., et al. 2000; *Science* 289, 1550; Li, Q., et al. 1999; and *Science* 284, 1999). Alternatively a sequence (SEQ ID NO:3) $(Arg)_8$-Gly-Gly-Thr-Ala-Leu-Asp-Trp-Ser-Trp-Leu-Gln-Thr-Glu-OH (or RRRRRRRR-GG-TALDWSWLQTE) will also be an ideal load molecule of the present invention. An analog of the inhibitory sequence of SEQ ID NO:1 and #2 is also an ideal load molecule for the composition of the present invention. This has sequence of (TAT-NBD; SEQ ID NO:4) H-Tyr-Gly-Arg-Lys-Lys-Arg-Arg-Gln-Arg-Arg-Arg-Gly-Thr-Thr-Leu-Asp-Trp-Ser-Trp-Leu-Gln-Met-Glu-OH (or YGRKKRRQRRRG-TTLDWSWLQME: from Dai, S., et al., 2004. *J. Biol. Chem.* 279(36): 37219). Another example is the peptide that can act at the intracellular level to stop autoimmune inflammatory diseases by binding to JNK interacting protein that activates JNK. Example is basic peptide linked to (SEQ ID NO: 62) Arg-Pro-Thr-Thr-Leu-Asn-Leu-Phe-OH (Basic-peptide-Arg-Pro-Thr-Thr-Leu-Asn-Leu-Phe-OH). More specific example of this has the sequence (SEQ ID NO:5) Tyr-Gly-Arg-Lys-Lys-Arg-Arg-Gln-Arg-Arg-Arg-Arg-Pro-Lys-Arg-Pro-Thr-Thr-Leu-Asn-Leu-Phe (or YGRKKRRQRRRRPK-RPTTLNLF from Melino, M., et.al., 2008, Journal of Immunology, vol 181, p 7300-7306). The portion of SEQ ID NO:5 Arg-Pro-Thr-Thr-Leu-Asn-Leu-Phe (residues 15-22 of SEQ ID NO: 5) is from JNK binding region and the sequence Tyr-Gly-Arg-Lys-Lys-Arg-Arg-Gln-Arg-Arg-Arg-Arg-Pro-Lys- (residues 1-14 of SEQ ID NO: 5) is the cell penetrating peptide or the peptide transduction domain. Another sequence that will fulfill the same purpose is as SEQ ID NO:4 is SEQ ID NO:6 $(Arg)_8$-Arg-Pro-Thr-Thr-Leu-Asn-Leu-Phe-OH. Another peptide that can suppress inflammation when linked to basic peptide is the P65-P1. That is basic peptide linked to (SEQ ID NO: 63) Gln-Leu-Arg-Arg-Pro-Ser-Asp-Arg-Glu-Leu-Ser-Glu-OH. When linked to basic peptide derived from antennapedia (PTD or peptide translocating domain), this can suppresses NF-kB activation induced by lipopolysaccharide, interleukin-1, okadaic acid, phorbol 12-myristate 13-acetate, and H2O2. This peptide may play a role in sensitizing cells to apoptosis induced by TNF, doxorubicin, and cisplatin. p65-P1 contains a single phosphorylation site, and it is needed to inhibit NF-kB activity. More specifically the sequence is (SEQ ID NO: 7) H-Asp-Arg-Gln-lle-Lys-Ile-Trp-Phe-Gln-Asn-Arg-Arg-Met-Lys-Trp-Lys-Lys-Gln-Leu-Arg-Arg-Pro-Ser-Asp-Arg-Glu-Leu-Ser-Glu-OH (or DRQ-IKIWFQNRRMKWKK-QLRRPSDRELSE from Takada, Y. et al., 2004, J. Biol. Chem. 279, p 15096). Alternatively the sequence can be (SEQ ID NO: 8) $(Arg)_8$-Gln-Leu-Arg-Arg-Pro-Ser-Asp-Arg-Glu-Leu-Ser-Glu-OH. Other sequences that interferes with NF-kB activation includes basic peptides linked to sequences selected from (SEQ ID NO: 64) Val-Gln-Arg-Lys-Arg-Gln-Lys-Leu-Met-Pro-OH (or VQRKRQKLMP from Lin, Y.-Z., et al. 1995. J. Biol. Chem. 270, 14255) or (SEQ ID NO: 65) Asp-Asp-Arg-His-Asp-Ser-Gly-Leu-Asp-Ser-Met-Lys-Asp-Glu-amide (or DDRHDSGLDSMKDE-$NH_2$ from Swaroop, N., et al. 2001, Pharm. Res. 18, 1631; Traenckner, E. B., et al. 1995, EMBO. J. 14, 2876). More specific examples are (SEQ ID NO: 9) $(Arg)_8$-Val-Gln-Arg-Lys-Arg-Gln-Lys-Leu-Met-Pro-OH and (SEQ ID NO: 10) $(Arg)_8$-DDRHDSGLDSMKDE-$NH_2$. Cortistatin-29 (human): (SEQ ID NO:11) Pyr-Glu-Gly-Ala-Pro-Pro-Gln-Gln-Ser-Ala-Arg-Arg-Asp-Arg-Met-Pro-Cys-Arg-Asn-Phe-Phe-Trp-Lys-Thr-Phe-Ser-Ser-Cys-Lys-OH (Disulfide bond). Pyr is pyroglutamic acid. This represents an anti-inflammatory, immunomodulatory factor with a potential multistep therapeutic use in the treatment of septic shock and Crohn's disease. (E. Gonzalez-Rey et al., J. Exp. Med., 203, 563 (2006); E. Gonzalez-Rey et al., Proc. Natl. Acad. Sci. USA, 103, 4228 (2006)). These peptides or their derivatives are examples of load molecules for the carrier of the present invention.

Interferons Type I, Type II, and Type III.

Interferons have antiinflammatory activity, especially type I interferons. Interferon beta (pI=8.9-9.7) for example is a type I interferon used for treatment of Multiple sclerosis and has antiinflammatory activity. The basic isoelectric-point of some of these interferons and/or the presence of positive charge patch on their surface is ideal for the carrier of the present invention. Such property allows them to bind the carriers of the present invention. Although such binding as exemplified by HB-EGF will be expected, by those who are knowledgeable and skilled in the art, to be overwhelmed by blood components, our surprising discovery is that such manner of binding to the carrier can withstand the presence of blood components, a result that is unexpected.

b) Anti-Infective Peptides (for Treatment of Infections)

Magainins are peptide antibiotics with antibacterial and antiparasitic activities, originally extracted from the skin of *Xenopus laevis*. Magainin 1 and 2 are closely related peptides of 23 amino acids each and differ by two substitutions. These antimicrobial peptides have broad-spectrum, non-specific activity against a wide range of micro-organisms, including viruses, gram-positive and gram-negative bacteria, protozoa, yeasts and fungi, and may also be hemolytic and cytotoxic to cancer cells. Magainin 1 is a bactericidal. Both Magainin 1 and 2 exhibit inhibitory action toward Herpes simplex virus type 1 (HSV-1) and HSV-2. (Williams, R W. et al. *Biophysical J*. 53, 631A (1988); Morvan, A. et al. *Mol. Mar. Biol. Biotechnol*. 3, 327 (1994); Matanic, A. et al. *Int. J. Antimicrob Agents* 23, 382 (2004); Zasloff, M. *Proc. Natl. Acad. Sci*. 84, 5449 (1987).) Magainin 1 sequence (SEQ ID NO:12) H-Gly-Ile-Gly-Lys-Phe-Leu-His-Ser-Ala-Gly-Lys-Phe-Gly-Lys-Ala-Phe-Val-Gly-Glu-Ile-Met-Lys-Ser-OH. This peptide or its derivative is an example of a load molecule for the carrier of the present invention.

Magainin 2 assumes an amphiphilic helix when bound to acidic phospholipids, forming a pore composed of a dynamic, peptide-lipid supramolecular complex. (SEQ ID NO:13) H-Gly-Ile-Gly-Lys-Phe-Leu-His-Ser-Ala-Lys-Lys-Phe-Gly-Lys-Ala-Phe-Val-Gly-Glu-Ile-Met-Asn-Ser-OH (Zasloff, M. Proc. Natl. Acad. Sci. USA. 84, 5449 (1987); Cruciani, R A. et al. EJPMOL 8, 187 (1992); Corzo, G. et al. Biochem. J. 359, 35 (2001); Matsuzaki, K. et al. Biochem. 36, 2104 (1997). This peptide or its derivative is an example of a load molecule for the carrier of the present invention.

Cecropin A (SEQ ID NO:14; H-Lys-Trp-Lys-Leu-Phe-Lys-Lys-Ile-Glu-Lys-Val-Gly-Gln-Asn-Ile-Arg-Asp-Gly-Ile-Ile-Lys-Ala-Gly-Pro-Ala-Val-Ala-Val-Val-Gly-Gln-Ala-Thr-Gln-Ile-Ala-Lys-NH2) is a naturally occurring, linear, cationic, 37-residue antimicrobial peptide. Cecropin A kills bacteria by dissipating transmembrane electrochemical ion-gradients. (Silvestro, L. et al. Biophysical J. 72, A195 (1997); Andreu, D. et al. Proc. Natl. Acad. Sci. USA 80, 6475 (1983); Silvestro, L. et al. Biochem. 36, 11452 (1997)). This peptide or its derivative is an example of a load molecule for the carrier of the present invention.

Cecropin B (SEQ ID NO:15; Lys-Trp-Lys-Val-Phe-Lys-Lys-Ile-Glu-Lys-Met-Gly-Arg-Asn-lle-Arg-Asn-Gly-Ile-Val-Lys-Ala-Gly-Pro-Ala-lle-Ala-Val-Leu-Gly-Glu-Ala-Lys-Ala-Leu-NH2) is a small antibacterial peptide from the giant silkmoth, *Hyalophora cecropia*. Antimicrobial peptides are essential to innate host defense as effectors of pathogen clearance and can affect host cell to promote wound repair. (Kulagina, N V. et al. *Sens Actuators B Chem.* 121, 150 (2007); Vaara, M. et al. Antimicrob. Agents Chemo. 38, 2498 (1994); Florack, D. et al. Transgenic Res. 4, 132 (1995); Lee, P. et al. Wound Repair Regen. 12, 351 (2004)). This peptide or its derivative is an example of a load molecule for the carrier of the present invention.

Human Platelet Factor 4 Derived Peptide or C18G (SEQ ID NO:16; H-Ala-Leu-Tyr-Lys-Lys-Leu-Leu-Lys-Lys-Leu-Leu-Lys-Ser-Ala-Lys-Lys-Leu-Gly-OH) from human platelet factor 4 is active against *salmonella*. C18G is a synthetic α-helical peptide derived from human platelet factor IV. This peptide was found to be antibacterial and is active against *Salmonella*. (Coconnier-Polter, M-H. et al. *Appl. Environ. Microbiol*. 71, 6115 (2005); Darveau, R. et al. *J. Clin. Invest*. 90, 447 (1992)). This peptide or its derivative is an example of a load molecule for the carrier of the present invention.

Histatin-8 [Hemagglutination-Inhibiting Peptide (HIP)]

(SEQ ID NO:17; H-Lys-Phe-His-Glu-Lys-His-His-Ser-His-Arg-Gly-Tyr-OH) is one of human salivary histatins (Hsts), which belong to a salivary polypeptide family, are small, cationic, and histidine-rich proteins. They have potent bactericidal and antifungal activities against *Candida albicans* and *Cryptococcus neoformans*, and are therefore potential therapeutic reagents against *Candida* species. They kill fungal cells by binding to the cell membrane, internalizing, and disrupting volume regulatory mechanisms and mitochondrial function, leading to the production of reactive oxygen species and non-lytic loss. (Yoshida, M. et al. *Biol. Pharm. Bull*. 24, 1267 (2001); Ahmad, M. et. al. *J. Histochem. Cytochem.* 52, 361 (2004).) This peptide or its derivative is an example of a load molecule for the carrier of the present invention.

Histatin-5

(SEQ ID NO:18; H-Asp-Ser-His-Ala-Lys-Arg-His-His-Gly-Tyr-Lys-Arg-Lys-Phe-His-Glu-Lys-His-His-Ser-His-Arg-Gly-Tyr-OH) is a human basic salivary anti-microbial peptide with strong fungicidal properties (Helmerhorst, E. et al. J. Biol. Chem. 274, 7286 (1999)). This peptide or its derivative is an example of a load molecule for the carrier of the present invention.

Histatin-3 or H3 (SEQ ID NO:19; H-Asp-Ser-His-Ala-Lys-Arg-His-His-Gly-Tyr-Lys-Arg-Lys-Phe-His-Glu-Lys-His-His-Ser-His-Arg-Gly-Tyr-Arg-Ser-Asn-Tyr-Leu-Tyr-Asp-Asn-OH) is found in human saliva and possesses powerful antimicrobial properties. This histidine-rich peptide is an inhibitor of proprotein convertases furin and PC7, but acts as substrate for PC1. (Basak, A. *J. Pept. Res.* 49, 596 (1997); Koshlukova, S. et al. *Infect Immun.* 68, 6848 (2000). This peptide or its derivative is an example of a load molecule for the carrier of the present invention.

HNP-1 or Defensin Human Neutrophil Peptide-1

(SEQ ID NO:21; H-Ala-Cys-Tyr-Cys-Arg-Ile-Pro-Ala-Cys-Ile-Ala-Gly-Glu-Arg-Arg-Tyr-Gly-Thr-Cys-Ile-Tyr-Gln-Gly-Arg-Leu-Trp-Ala-Phe-Cys-Cys-OH (Disulfide bridge: 2-30, 4-19, 9-29). Mammalian defensins are abundant in the cytoplasmic azurophilic granules of neutrophils, Paneth cells of the small intestine and some macrophages. HNP-1 is a peptide possessing both broad antimicrobial (both Gram-positive and Gram-negative bacteria) and cytotoxic activities. HNP-1 reduces adenoviral infection by more than 95%. (Frick, I. et al. J. Biol. Chem. 278, 16561 (2003); Valore, E. at al. J. Clin. Invest. 97, 1624 (1996); Mizukawa, N. et al. Anticancer Res. 20, 1125 (2000); Bastian, A. and H. Schafer, Regul Pept. 101, 157 (2001)). This peptide or its derivative is an example of a load molecule for the carrier of the present invention.

Apidaecin IA (SEQ ID NO:22; H-Gly-Asn-Asn-Arg-Pro-Val-Tyr-Ile-Pro-Gln-Pro-Arg-Pro-Pro-His-Pro-Arg-Ile-OH) is unique antibacterial peptide derivative found in immune honey bee lymph. Apidaecins, the most prominent components of the honey bee humoral defense against microbial invasion, are a series of small, proline-rich 18- to 20-residue peptides. They inhibit viability of Gram-negative bacteria; with near immediate lethal activity, independent of a conventional "lytic" mechanism, and involves stereoselective recognition of target molecules. (Casteels-Josson, K. et al. EMBO J. 12, 1569 (1993); Casteels, P. J. Biol. Chem. 269, 26107 (1994); Li, W. et al. Pept. 27, 2350 (2006)). This peptide or its derivative is an example of a load molecule for the carrier of the present invention.

Pyrrhocoricin:

(SEQ ID NO:23; H-Val-Asp-Lys-Gly-Ser-Tyr-Leu-Pro-Arg-Pro-Thr-Pro-Pro-Arg-Pro-Ile-Tyr-Asn-Arg-Asn-OH). This proline-rich cationic antibacterial peptide pyrrhocoricin kills responsive bacteria by binding to the 70 kDa heat shock protein DnaK and inhibiting protein folding. (Cudic, M. et al. Peptides 23, 2071 (2002), Bulet, P. et al. Dev. Comp. Immunol 23, 329 (1999)). This peptide or its derivative is an example of a load molecule for the carrier of the present invention.

Killer Peptide 1 (KP1):

(SEQ ID NO:24 $(KLAKLAK)_2-NH_2$) is a helical antimicrobial peptide that is disrupted highly anionic cell membrane (bacterial membrane are more highly anionic than mammalian cell membrane) and kills bacterial cells preferentially. A longer sequence (SEQ ID NO:25 $(KLAKLAK)_3-NH_2$) is more selective against bacterial cells (Javadpour, M. M. et al. J. Med. Chem. 1996, 39:3107-3113). These peptides or their derivatives will be are ideal load molecules for the carrier of the present invention.

Human Cathelecidin Fragment 104-140 (LL-37):

(SEQ ID NO: 26: LLGDFFRKSK EKIGKEFKRI VQRIKDFLRN LVPRTES). The human cationic antimicrobial protein of 18 kDa (hCAP-18) belongs to the class of cathelicidins. It is released from activated neutrophil granulocytes. After release, the 37-amino-acid alpha-helical C-terminal end is cleaved off, forming the functional antimicrobial peptide LL-37. Apart from being antimicrobial, LL-37 also binds LPS, and it was previously shown that this binding reduces LPS-induced nitric oxide release from the rat aorta and protects mice from LPS lethality. LL-37 has also been found to have immunomodulatory and chemotactic activities mediated via the formyl peptide receptor FPRL1. Because human cathelicidin-derived peptide LL-37 binds and neutralizes bacterial lipopolysaccharide (LPS), this might therefore have beneficial effects in the treatment of septic shock. Other variants including LL-37 N-terminal truncation, named 106 (aa 106 to 140, SEQ ID NO:27: GDFFRKSKEK-IGKEFKRIVQ-RIKDFLRNLV-PRTES), 110 (aa 110 to 140, SEQ ID NO: 28: RKSKEKIGKE FKRIVQRIKD FLRNLVPRTE S), BMAP-27 (SEQ ID NO: 30: GRFKRFRKKFKKLFKKLSPVIPLLHL-am), and a more hydrophobic variant, the 18-mer LLKKK (SEQ ID NO: 29: KLFKRIVKRI-LKFLRKLV). LL-37, fragments 106 and 110, and the 18-mer LLKKK inhibited the growth of *Escherichia coli, Pseudomonas aeruginosa, Staphylococcus aureus*, and *Candida albicans* in a radial diffusion assay, inhibited lipopolysaccharide-induced vascular nitric oxide production, and attracted neutrophil granulocytes similarly. While fragments 106 and 110 caused less hemolysis and DNA fragmentation in cultured cells than did LL-37, the 18-mer LLKKK induced severe hemolysis. The antibacterial effect of fragments 106 and 110 was not affected by serum, while the effect of LL-37 was reduced. The removal of N-terminal hydrophobic amino acids from LL-37 decreases its cytotoxicity as well as its inhibition by serum without negatively affecting its antimicrobial or LPS-neutralizing action. Such LL-37-derived peptides may thus be beneficial for the treatment of subjects with sepsis. (Ciornei et. al. Antimicrobial Agents and Chemotherapy, 2005, 49(7): 2845-2850; Bals et al., *J. Clin. Invest.,* 1999, 103:1113-1117; Deslouches et al., Antimicrobial Agents and Chemotherapy, 2005, 49(8)3208-3216). These peptides or their derivatives are examples of ideal load molecules for the carrier of the present invention.

Protegrin-1 or PG-1:

(SEQ ID NO: 36: RGGRLCYCRRRFCVCVGR) and derivatives IB-367 or Iseganan: SEQ ID NO: 37: RGGLCYCRGRFCVCVGR (Chen et al., Journal of Chromatography A, 853 (1999) 197-206; Jang et al., BMC Structural Biology 2007, 7:21; van Saene et al., van Saene et al., Chest, 2007, 132:1412; Kollef et al., America, Journal of Respiratory and Critical care, 2006, 173; Shi et al., Infection and Immunity, 1998, 66(8):3611-3617. The protegrin family of antimicrobial peptides was identified in porcine leukocytes. Five native protegrin sequences (PG-1 to PG-5) have now been identified. These native protegrins contain 16 to 18 amino acids, are highly homologous, and share the common feature of being cationic, amphipathic b-sheets. The molecules have disulfide bridges between cysteine residues at positions 6 and 15 as well as positions 8 and 13. Iseganan, an antimicrobial peptide, is active against aerobic and anaerobic gram-positive and gram-negative bacteria as well as fungi and yeasts. These peptides or their derivatives will be are ideal load molecules for the carrier of the present invention.

K4:

(SEQ ID NO: 38: KKKKPLFGLFFGLF) is a an antimicrobial peptide designed using Antimicrobial Peptide Database. This peptide has strong activity (lyses bacterial cells) against gram-positive and gram-negative bacteria including human pathogenic bacteria such as *Staphylococcus aureus* and some marine bacteria of the genus *Vibrio*. The peptide is non-toxic to mammalian cells for bacteriolytic concentrations. (Duval et al., Peptides, 2009, 30:1608-1612). This peptide or its derivative is an example of a load molecule for the carrier of the present invention.

Indolicidin:

Indolicidin is a 13-amino-acid antimicrobial peptide present in the cytoplasmic granules of bovine neutrophils. Indolicidin is a member of the cathelicidin family of antimicrobial peptides isolated from mammalian myeloid cells. As a naturally occurring peptide, indolicidin has a unique composition consisting of 39% tryptophan and 23% proline (SEQ ID NO: 39: ILPWKWPWWPWRR-am; and variants, SEQ ID NO: 40: ILPWKWPWWPWRR-meth; SEQ ID NO: 41: ILKKWPWWPWRRK; SEQ ID NO: 42: ILKKWPWWPWRRK-meth), and in nature the peptide is amidated at the C terminus. Indolicidin has activity against gram-negative and -positive bacteria, fungi, and protozoa. These peptides or their derivatives will be are ideal load molecules for the carrier of the present invention.

Human Lactoferrin Fragment (hLF(1-11):

(SEQ ID NO: 43: GRRRRSVQWCA) Human lactoferrin (hLF) is a major component of the nonspecific defense of mucosal surfaces and neutrophils and is active against a variety of pathogens. Studies with synthetic peptides corresponding to the first 11 N-terminal amino acids, designated hLF(1-11), has the bacterial killing activity. (Nebbering et al. Infection and Immunity, 2001, 69(3):1469-1476. This peptide or its derivative is an example of a load molecule for the carrier of the present invention.

Polyphemusin 1 and Tachyplesin I: (SEQ ID NO: 44: RRWCFRVCYRGFCYRKCR-$NH_2$, SEQ ID NO: 45: KWCFRVCYRGICYRRCR-NH2). Tachyplesins are from the Japanese horseshoe crab *Tachypleus tridentatus*, and Polyphemusins are from the American horseshoe crab *Limulus polyphemus*. These peptides are 17-18 amino acid residues in length, contain two disulfide bonds and have an amidated C-terminal arginine. Both families of peptides possess antibacterial activity, inhibiting the growth of both Gram-positive and Gram-negative species, and fungi, in addition to an ability to prevent the replication of enveloped viruses such as influenza A and HIV. These peptides or their derivatives will be are ideal load molecules for the carrier of the present invention.

Interferon gamma (pI=8.5-9.5) is a type II interferon that has anti-viral activity and can be used for treatment of hepatitis infection and other viral infections. Interferon betas (pI=8.9-9.7) are type I interferons that has anti-viral activity can be used for treatment of hepatitis infections. These interferons have basic isoelectric points and are among the ideal load molecules for the carrier of the present invention.

c) Growth-Stimulators (for Treatment of Tissue Injuries)

PR39, Anti-Apoptotic Factor (SEQ ID NO:31; H-Arg-Arg-Arg-Pro-Arg-Pro-Pro-Tyr-Leu-Pro-Arg-Pro-Arg-Pro-Pro-Pro-Phe-Phe-Pro-Pro-Arg-Leu-Pro-Pro-Arg-Ile-Pro-Pro-Gly-Phe-Pro-Pro-Arg-Phe-Pro-Pro-Arg-Phe-Pro-OH) was originally isolated from pig intestine, this proline and arginine rich 39 amino acid peptide is also found in neutrophil azurophilic granules and macrophages. This peptide plays a role in cell motility and metastatic potential in wound repair; binds to NADPH oxidase complex protein p47phox7 and a signaling adaptor protein p130Cas. And recently, PR39 is found to inhibit hypoxia-induced apoptosis and decrease caspase-3 activity in endothelial cells. (Wu, J. et al. *Circulation* 109, 1660 (2004)). Derivatives of PR39 includes SEQ ID NO:32: RRRPRPPYLPRPRPPPFFPPRLPPRI or PR26; SEQ ID NO:33: RRRPRPPYLPRPRPPPFFP or PR19; SEQ ID NO:34: RRRPRPPYLPR or PR11; and related peptide such as SEQ ID NO: 35: RLCRIVVIRVCR or Bactenecin. (Agerberth, B. et al., Eur. J. Biochem., 202, 849-854, 1991; Boman, H. G. et al., Infect. Immun., 61, 2978-2984, 1993; Agerberth, B. et al., Vet. Immunol. Immunopathol., 54, 127-131, 1996; Gallo, R. L. et al. Proc. Natl. Acad. Sci. USA, 91, 11035-11039, 1994; Li, J. et al., Circ. Res., 81, 785-796, 1997; Gudmundsson, G. H. et al., Proc. Natl. Acad. Sci. USA, 92, 7085-7089, 1995; Li, J. et al., Nature. Med., 6, 49-55, 2000; Li, J. et al., Nature. Med., 6, 356, 2000; Gao, Y. et al., J. Clin. Invest., 106, 439-448, 2000; Bao, J. et al. Am. J. Physiol. Heart Circ. Physiol., 281, 2612-2618, 2001; Madhani et al., Biochimica et Biophysica Acta 1588 (2002) 232-240). These peptides or their derivatives will be are ideal load molecules for the carrier of the present invention.

TGF beta activating peptide. A thrombospondin (TSP-1) derived Transforming Growth Factor β (TGF-β) activating peptide. This basic motif (SEQ ID NO:46) H-Lys-Arg-Phe-Lys-NH2 (KRFK) in combination with Trp-Xaa-Xaa-Trp sequences induces strong heparin binding. This sequence Trp-Xaa-Xaa-Trp is the amino acids 412-415 of TSP-1 and is sufficient to activate latent TGF-β. (Shultz-Cherry, S. et al. J. Biol. Chem. 270, 7304 (1995); Guo, N. et al. J. Biol. Chem. 267, 19349 (1992)). Example of sequences derived from th the above motif are SEQ ID NO:48 (H-Lys-Arg-Phe-Lys-Gln-Asp-Gly-Gly-Trp-Ser-His-Trp-Ser-Pro-Trp-Ser-Ser-OH; or KRFKQDGGWSHWSPWSS) and SEQ ID NO:49 (H-Lys-Arg-Phe-Lys-Gln-Asp-Gly-Gly-Trp-Ser-His-Trp-Ser-Pro-OH; or KRFKQDGGWSHWSP). These peptides or their derivatives will be are ideal load molecules for the carrier of the present invention.

d) Growth-Inhibitor (for Treatment of Cancer and Excess Growth of Cells or Scars)

Alpha Interferons (pI=8.8-9.1) are type I interferons that can be useful for the treatment of some types of cancer. Alpha interferons can be used to treat cancer of the kidney, malignant melanoma, cutaneous melanoma, multiple myeloma and carcinoid tumours. It can also be used to treat certain types of lymphoma and leukaemia. Interferon gamma (pI=8.5-9.5) is a type II interferon that has anti-scarring activity (suppresses excess growth/activity of scar forming cells) and can be used for treatment of liver cirrhosis, pulmonary fibrosis, Chronic Granulomatous disease, osteopetrosis, and mycobacterium induced scarring. Scarring or excess connective tissue deposits can be caused by chemicals or infections.

TGF-beta inhibitors derived from or comprising anyone of SEQ ID NO:56 (FCLGPCPYIWSLDT or $Tb_1$43-56), SEQ ID NO:57 (TSLDASIWAMMQNA or P144), SEQ ID NO:58 (KRIWFIPRSSWYERA or P17), and SEQ ID NO:58 (TSLDATMIWTMM). These peptides can be modified to contain basic residues to be able to bind the carrier of the present invention, with the resulting composition that will be useful for the treatment of liver cirrhosis, pulmonary fibrosis, Chronic Granulomatous disease, osteopetrosis, and mycobacterium induced scarring.

bFGF Inhibitor (SEQ ID NO:50; H-Lys-Arg-Thr-Gly-Gln-Tyr-Lys-Leu-OH): This peptide corresponds to human, bovine (119-126), mouse, rat (118-125) and Heparin-Binding Growth Factor 2 (118-125) residues of bFGF. It inhibits dimerization and activation of bFGF receptors. (Yayon, A. et al. Proc. Natl. Acad. Sci. USA, 90, 10643 (1993)). This peptide or its derivative is an example of a load molecule for the carrier of the present invention.

Fibroblast Growth Factor-2 (FGF-2) Derived Peptide:

FGF-2 is an autocrine growth factor in the autonomous proliferation of glioma cells. The FGF-2 derived peptide (SEQ ID NO:51; H-Met-Trp-Tyr-Arg-Pro-Asp-Leu-Asp-Glu-Arg-Lys-Gln-Gln-Lys-Arg-Glu-OH) suppresses growth of malignant glioma. This 16-residue peptide has conformational similarity to the putative receptor-binding domain of FGF-2. It suppresses growth of human glioma cells and is a potential new treatment product for malignant glioma (Kono, K. et al. J. Neuro-Oncology 63, 163 (2003)). This peptide or its derivative is an example of a load molecule for the carrier of the present invention.

Charybdotoxin (SEQ ID NO:52; Pyr-Phe-Thr-Asn-Val-Ser-Cys-Thr-Thr-Ser-Lys-Glu-Cys-Trp-Ser-Val-Cys-Gln-Arg-Leu-His-Asn-Thr-Ser-Arg-Gly-Lys-Cys-Met-Asn-Lys-Lys-Cys-Arg-Cys-Tyr-Ser-OH (Disulfide bridge: 7-28, 13-33 and 17-35)): Charybdotoxin (ChTX) is a Ca2+-activated K+ channel blocker. It depolarizes peripheral T lymphocytes and blocks their mitogen-induced proliferation. ChTX is a highly basic peptide isolated from venom of the scorpion, *Leiurus quinquestriatus hebraeus*. (Leonard, R. et al. Proc. Natl. Acad. Sci. USA 89, 10094 (1992); Gimenez-Gallego, Proc. Natl. Acad. Sci. USA 85, 3329 (1988). Sugg, E. et al. J. Biol. Chem. 265, 18745 (1990)). This peptide or its derivative is an example of a load molecule for the carrier of the present invention.

Antennapedia Bak BH3 (Ant-BH3) (71-89) Fusion Peptide (SEQ ID NO:53: H-Arg-Gln-Ile-Lys-Ile-Trp-Phe-Gln-Asn-Arg-Arg-Met-Lys-Trp-Lys-Lys-Met-Gly-Gln-Val-Gly-Arg-Gln-Leu-Ala-Ile-Ile-Gly-Asp-Asp-Ile-Asn-Arg-Arg-Tyr-OH). This is a fusion peptide containing amino acids 71 to 89 fragment of the Bak BH3 domain fused to antennapedia peptide. The Bcl-2 homology 3 (BH3) domain is crucial for the death-inducing and dimerization properties of pro-apoptotic members of the Bcl-2 protein family, including Bak, Bax, and Bad. Synthetic peptides corresponding to the BH3 domain of Bak bind to Bcl-xL, antagonize its anti-apoptotic function, and rapidly induce apoptosis when delivered into intact cells via fusion to the antennapedia homeoprotein internalization domain. Holinger, E. et al. J. Biol. Chem. 274, 13298 (1999). This peptide or its derivative is an example of a load molecule for the carrier of the present invention.

Tumor Targeted Pro-Apoptotic Peptide:

(SEQ ID NO:54: H-Cys-Asn-Gly-Arg-Cys-Gly-Gly-D-Lys-D-Leu-D-Ala-D-Lys-D-Leu-D-Ala-D-Lys-D-Lys-D-Leu-D-Ala-D-Lys-D-Leu-D-Ala-D-Lys-NH2 (with intrapeptide disulfide bond and the D represent D-isomer of the amino acid). This is the same as CNGRCGGklaklakklaklak-NH$_2$ (Disulfide bond) (SEQ ID NO: 54) or CNGRC-GG-(klaklak)$_2$-NH$_2$ (with intrapeptide disulfide bond) (SEQ ID NO: 54) where the small letter amino acid codes represent the D-isomer of the corresponding amino acids. This peptide consists of two functional domains, on the one hand a "homing" or targeting domain, which guides the peptide to targeted cells and allows its internalization and on the other hand a programmed cell death-inducing sequence. The targeting domain contains the Asn-Gly-Arg (NGR) motif which has proven useful for delivering various anti-tumor compounds and viral particles to tumor vessels. As programmed cell death-inducing sequence the synthetic 14 amino acid peptide klaklakklaklak, also called (klaklak)$_2$, was selected, because it kills bacteria at concentrations 1% of those required to kill eukaryotic cells. This pro-apoptotic domain is non-toxic outside of cells, but toxic when internalized into targeted cells by the disruption of mitochondrial membranes. Therefore, targeted pro-apoptotic peptides represent a potential new class of anti-cancer agents. They combine two levels of specificity: "homing" to targeted cells and selective apoptosis of such cells after entry. (H. M. Ellerby et al., Nat. Med., 5, 1032 (1999); G. Colombo et al., J. Biol. Chem., 277, 47891 (2002); L. A. Plesniak et al., Protein Sci., 13, 1988 (2004). This peptide or its derivative is an example of a load molecule for the carrier of the present invention. Sequences presented in Table 1 are based on single letter abbreviation for each amino acid as known in the art and the represented amino acids can be D or L isomers. "Pyr" indicates pyroglutamate, "am" indicates aminated at the carboxyl terminal, and "meth" indicates methylation.

TABLE 1

Examples of peptide load molecules as elements of the present invention.

Anti-Inflammatory Peptides (for Diabetes, RA, Crohn's disease, MS, etc.)

| ID NO. | Sequence | Name/derivative of/(action) |
|---|---|---|
| 1 | KKKKKKKK-GG-TALDWSWLQTE | IKK inh./NBD/(bl NFkB act) |
| 2 | DRQIKIWFQNRRMKWKK-TALDWSWLQTE | IKK inh./NBD(bl NFkB act) |
| 3 | RRRRRRRR-GG-TALDWSWLQTE | IKK inh./NBD/(bl NFkB act) |
| 4 | YGRKKRRQRRRG-TTLDWSWLQME | IKK inh/NBD/(bl NFkB act) |
| 5 | YGRKKRRQRRRPK-RPTTLNLF | JNK inh. (no AP1 act) |
| 6 | RRRRRRRR-RPTTLNLF | JNK inh. (no AP1 act) |
| 7 | DRQIKIWFQNRRMKWKK-QLRRPSDRELSE | NFkB inh. (apoptotic)P65-P1 |
| 8 | RRRRRRRR-QLRRPSDRELSE | NFkB inh. (enhance apoptosis) |

TABLE 1-continued

| ID NO. | Sequence | Name/derivative of/action |
|---|---|---|
| | Examples of peptide load molecules as elements of the present invention. | |
| 9 | RRRRRRRR-VQRKRQKLMP | NFkB nuclear Trans inh. |
| 10 | RRRRRRRR-DDRHDSGLDSMKDE-am | IKK inh. (bl NFkB act) |
| 11 | Pyr-EGAPPQSARRDRMPCRNFFWKTFSSCK | Cortistatin (like somatostatin) |
| ID NO. | Sequence | Name/derivative of/action |
| | Anti-Infective Peptides | |
| 12 | GIGKFLHSAGKFGKAFVGEIMKS | Magainin1 |
| 13 | GIGKFLHSAKKFGKAFVGEIMNS | Magainin2 |
| 14 | KWKLFKKIEKVGQNIRDGIIKAGPAVAVVGQATQIAK | Cecropin A |
| 15 | KWKVFKKIEKMGRNIRNGIVKAGPAIAVLGEAKAL | Cecropin B |
| 16 | ALYKKLLKKLLKSAKKLG | C18G (platelet-Factor4) |
| 17 | KFHEKHHSHRGY | Histatin 8 |
| 18 | DSHAKRHHGYKRKFHEKHHSHRGY | Histatin 5 |
| 19 | DSHAKRHHGYKRKFHEKHHSHRGYRSNYLYDN | Histatin 3 |
| 20 | AKRHHGYKRKFH-am | P-113-Histatin derivative |
| 21 | ACYCRIPACI-AGERRYGTCI-YQGRLWAFCC (S-S; 2-30, 4-19, 9-29) | Defensin HNP-1 |
| 22 | GNNRPVYIPQPRPPHPRI | Apidaecin IA |
| 23 | VDKGSYLPRPTPPRPIYNRN | Pyrrhocoricin |
| 24 | $(KLAKLAK)_2$-$NH_2$ | KP1; More potent than 12-15, less tox on 3T3 cells |
| 25 | $(KLAKLAK)_3$-$NH_2$ | |
| 26 | LLGDFFRKSKEKIGKEFKRIVQRIKDFLRNLVPRTES | LL-37 |
| 27 | GDFFRKSKEKIGKEFKRIVQRIKDFLRNLVPRTES | F-106 from LL37 |
| 28 | RKSKEKIGKEFKRIVQRIKDFLRNLVPRTES | F-110 from LL37 |
| 29 | KLFKRIVKRILKFLRKLV | LLKKK from LL37 |
| 30 | GRFKRFRKKFKKLFKKLSPVIPLLHL-am | BMAP-27 Bovine Cathelicidin |
| 31 | RRRPRPPYLPRPRPPPFFPPRLPPRIPPGFPPRFPPRFP | PR39 (also growth stimulator) |
| 32 | RRRPRPPYLPRPRPPPFFPPRLPPRI | PR26 from PR39 |
| 33 | RRRPRPPYLPRPRPPPFFP | PR19 from PR39 |
| 34 | RRRPRPPYLPR | PR11 from PR39 |
| 35 | RLCRIVVIRVCR; with intramolecule disulfide bond | Bactenecin |
| 36 | RGGRLCYCRRRFCVCVGR | Protegrin 1 (Jang 07; fr Sepsis; Steinstraesser 2003) |
| 37 | RGGLCYCRGRFCVCVGR | IB-367; Iseganan |
| 38 | KKKKPLFGLFFGLF | K4 |
| 39 | ILPWKWPWWPWRR-am | Indolicidin (Falla 1996&1997) |
| 40 | ILPWKWPWWPWRR-meth | Indolicidin-C |
| 41 | ILKKWPWWPWRRK | C11 from Indolicidin |
| 42 | ILKKWPWWPWRRK-meth | C11-C from Indolicidin |
| 43 | GRRRRSVQWCA | hLF(1-11) from human lactoferrin |

TABLE 1-continued

| Examples of peptide load molecules as elements of the present invention. | | |
|---|---|---|
| 44 | RRWCFRVCYRGFCYRKCR-$NH_2$ | Polyphemusin I |
| 45 | KWCFRVCYRGICYRRCR-$NH_2$ | Tachyplesin I |
| | Growth stimulator | |
| 46 | KRFK | Heparin Binder |
| 47 | KRFK-$(Xaa)_y$-W-Xaa-Xaa-W; where Xaa = any amino acids and y is 0-10. | TGF-beta activator (TSP-1) |
| 48 | KRFKQDGGWSHWSPWSS | TGF-beta activator (TSP-1) |
| 49 | KRFKQDGGWSHWSP | TGF-beta activator (TSP-1) |
| (31) | RRRPRPPYLPRPRPPPFFPPRLPPRIPPGFPPRFPPRFP | PR39, Anti-Apoptotic (for Sepsis) |
| (32) | RRRPRPPYLPRPRPPPFFPPRLPPRI | PR26 from PR39 |
| (33) | RRRPRPPYLPRPRPPPFFP | PR19 from PR39 |
| (34) | RRRPRPPYLPR | PR11 from PR39 |
| | Cell growth inhibitors or scar growth inhibitors or pro-apototic agents | |
| 50 | KRTGQYKL | bFGF inhibitor; prevent dimer |
| 51 | MWYRPDLDERKQQKRE | FGF-2 inhibitor; Anti-glioma |
| 52 | PyrFTNVSCTTSKECWSVCQRLHNTSRGKCMNKKCRCYS (S-S; 7-28, 13-33 and 17-35); Pyr is pyroglutamate | Charybdotoxin; blocks T-lymp |
| 53 | RQIKIWFQNRRMKWKKMGQVGRQLAIIGDDINRRY | Ant-BH3 fusion; pro-apototic by blocking anti-apoptotic Bcl-2 (Bcl-xL) |
| 54 | CNGRCGGklaklakklaklak-$NH_2$; small case are D-amino acids to prevent degradation; with disulfide bond | Tumor Targeted Pro-Apoptotic Peptide |
| 55 | CNGRC-GG-KLAKLAKKLAKLAK-am; with disulfide bonds | Tumor Targeted Pro-Apoptotic Peptide |
| 56 | FCLGPCPYIWSLDT | $Tb_1$43-56 (anti-TGF beta) |
| 57 | TSLDASIWAMMQNA | P144 (anti-TGF beta) |
| 58 | KRIWFIPRSSWYERA | P17 (anti-TGF beta) |
| 59 | TSLDATMIWTMM | P54 (anti-TGF beta) |

Protein and peptide electrostatically bound to the carrier according to the present invention may result in longer circulation in the body, more stability in the blood, and/or more convenient administration (for example, quicker administrations such as through bolus instead of infusion, and less frequent administrations, e.g. once every few days instead of infusion or once a day). Often chronic administration of a basic protein active agent may be immunogenic. Carrier based formulations generally result in less immunogenicity than PEG based delivery systems so the basic protein or peptide is expected to be less immunogenic in compositions of the present inventions. "Direct PEGylation" of the active agent is the direct bonding of the protein to PEG and can results in loss of activity. A cationic protein or peptide electrostatically bound to anionic groups which is covalently linked to the backbone of the carrier with protective side chains, however, can result in a stable, long circulating alternative to PEGylation. In one embodiment, the interaction between the load molecule and the anionic group of the composition is more stable in the blood than the interaction between the load molecule and hydrophobic groups that may be elements of the composition. The carriers of the present invention may act as a cryoprotectant and macromolecular stabilizer preserving basic protein or peptide active agent in solution as well as during the lyophilization and reconstitution process.

While the electrostatically-bound protein or peptide/carrier combinations are described herein as compositions, they may alternatively be understood as compounds that include electrostatic bonds. In various embodiments of the invention, components not listed herein that may alter the operation of the invention may be excluded while still permitting the inclusion of components that do not alter the operation of required components. Features not listed herein that may alter the operation of the invention may be excluded by use of the phrase "consisting essentially of" in describing the required features of the invention. However, the use of the phrase "consisting essentially of" does not exclude features that do not alter the operation of the required components. In one embodiment, "consisting essentially of" means that the Kd for ionic interactions is less than 10 μM and no other interaction, such as hydrophobic interactions, will have a Kd less than 10 μM.

Sustained Release:

When the carrier of the present invention is use to formulate a protein or peptide active agent, a release of the active agent for an extended period will be observed as evident from the sustained presence of the active agent in the blood compared to administering the active agent alone. The association of carrier with the active agent is defined by specific dissociation constant (Kd) that can easily be determined by those skilled in the art. The release will be determined by the concentration of free active agent such that the when the free active agent concentration goes down (due to degradation or elimination by the body) and Kd is no longer satisfied, more active agent will be released to satisfy the Kd. The Kd is the product of concentration of free active agent and the concentration of anionic clusters (not associated with the active agent) divided by the concentration of the active agent associated with anionic groups. For the compositions of the present invention that form supramolecular structures such as micelles, liposomes and other structures, the release rate will still follow the Kd but due to compartmentalization the Kd will only be satisfied in each specific compartment. However, long term mixing of the various compartments can result in eventual release of the active agent into the surrounding environment. In both cases whether compartmentalization is involved or not, a release profile will result in prolonged delivery (over, for example 1 to about 4,000 hours, or alternatively about 4 to about 1500 hours) of effective amounts (e.g., about 0.00001 mg/kg/hour to about 10 mg/kg/hour) of the active agent. The advantage of the formulation is less frequent bolus administration from continuous to once a day or even once a week. This will provide a more constant level of active agent in the blood with less fluctuation compared to an unformulated active agent. The frequency of bolus administration will vary according to the needs of the subject and can easily be determined by those skilled in the art. Without wishing to be bound by theory, in one embodiment, an advantage of the invention over a carrier containing a hydrophobic moiety is in the manufacture process of the present invention, which may allow the use of water without the need for organic solvents. Aqueous systems may represent a significant manufacturing advantage.

Therapeutic Uses

A "patient," "subject" or "host" to be treated with the composition of the present invention may mean either a human or non-human animal. The basic proteins (cationic protein) of the present invention are useful in the treatment of such diseases and disorders such as but not limited to bacterial infections, cancer and related neoplastic diseases, and Alzheimer's disease. In one embodiment, the compositions of the present invention may be used in the manufacture of a medicament for any number of uses, including for example treating any disease or other treatable condition of a subject.

A) Treatment of Inflammation

In one embodiment, the composition of the present invention with load molecule comprising SEQ ID NO:1-11 or their derivatives or analogs can be used to treat inflammation. Examples of chronic inflammatory diseases that can benefit from the composition of the present invention are: rheumatoid arthritis, chronic inflammatory bowel disease, Crohn's disease, ulcerative colitis, and diabetes.

B) Treatment of Infections

In one embodiment, the composition of the present invention with load molecule comprising SEQ ID NO:12-45 or their derivatives or analogs can be used to treat infections. In another embodiment, the basic proteins of the present invention are useful in the treatment of bacterial infections. Exemplary active agents for treatment include lysostaphin, a basic protein that has overall positive charge at physiological pH. Lysostaphin cleaves pentaglycine cross-bridges in the cell wall peptidoglycan of gram positive bacteria. *S. aureus* is particularly susceptible to the bacteriolytic effects of this enzyme since its cell wall contains a high proportion of pentaglycine cross-bridges. Lysostaphin is a potential systemic therapy for treating multidrug-resistant *S. aureus* mediated infections including endocarditis, osteomyelitis, catheter related infections, and MRSA-mediated community acquired furunculosis and pneumonia.

C) Treatment of Tissue or Cell Damage

In one embodiment, the basic proteins of the present invention includes Transforming Growth Factor (TGF-alpha, -beta 1, -beta 2, -beta 3; pI 8-9), Vascular endothelial growth factor (VEGF-A, -B, -C, -D; pI 8.0-9.5), Fibroblast growth factor (FGF, with 22 members; pI 8.0-9.0), Hepatocyte growth factor (HGF; has positive sites that bind sulfate residues), Nerve growth factor (NGF, pI 8.5-9.5), and a platelet derived growth factor (PDGF-AA, -BB, -AB; pI 8.5-10). Theses growth factors are useful in stimulating growth of injured organ such pancreatic islets in case of diabetes or heart is case of myocardial infarction. These growth factors can be formulated or combined with the carrier of the present invention and used for the treatment of diabetes or myocardial infarction. The above proteins have overall positive charge at physiological pH or that have a patch of positive charge and are capable of binding the anionic groups of the carrier of the present invention. Other members of epidermal growth factor (EGF) family including heparin binding EGF (HB-EGF), Betacellulin (BTC), Amphiregulin (AR), Epiregulin (EPR), Epigen (EPR), and neuroregulin have binding sites capable of binding sulfate moieties and can be formulated using the carrier of the present invention. TGF-alpha, VEGF, and HB-EGF can be use to grow islet cells in diabetes. In another embodiment, the composition of the present invention with load molecule comprising SEQ ID NOS: 31-34 and 46-49 or their derivatives or analogs can be used to treat tissue or cell damage. In yet another embodiment, the load molecule of the present invention can be anyone of Fibroblast growth factor (FGF; pI 9.6), basic Fibroblast growth factor (bFGF) or erythropoietin without sialic acid (pI 8.5). All members of FGF family have basic isoelectric point or have patches of positive charges on their surface that can bind anionic groups in the carrier of the present invention. These growth factors are useful for the treatment of radiation or chemical injuries that requires organ regeneration. For example, accidental exposure to radiation will benefit from the use of long acting FGF (a formulation of FGF with anionic core carrier of the present invention) that will improve regeneration of the intestinal mucosa and the bone marrow. The formulation of erythropoietin in the anionic core carrier of the present invention will be useful for the treatment of bone marrow damage or collapse by accelerating the recovery of bone marrow, especially when the level of erythropoietin is maintained for a sustain period of time due to the carrier of the present invention.

D) Treatment of Cancer or Excess Growth

In another embodiment, the composition of the present invention with load molecule comprising SEQ ID NO:50-55 or their derivatives or analogs can be used to treat cancer or excess growth.

Administration and Dosages

A "patient," "subject" or "host" to be treated with the composition of the present invention may mean either a human or non-human animal.

The term "pharmaceutically acceptable excipient" is art-recognized and refers to a pharmaceutically-acceptable material, composition or vehicle, such as a liquid or solid filler, diluent, solvent or encapsulating material administered along with the composition. Each excipient is "acceptable" in the sense of being compatible with the other ingredients of the supplement and not injurious to the subject. Some examples of materials which may serve as pharmaceutically acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The dosage of the peptide/protein active agent of the present invention will vary depending on the symptoms, age and body weight of the subject, the nature and severity of the disease or disorder, the route of administration, and other drugs/active agents being administered to the subject in conjunction. The dosage should always be given to insure that the benefit of the peptide/protein outweighs the risk to the subject in terms of toxicity and other side effects. In embodiments where the active agent is lysostaphin, the dosage will depend on the severity of the infections, and the form of other supplemental antibiotics. In embodiments where the active agent is anti-inflammatory agent, the dosage will depend on the severity of the inflammation and the cause of inflammation, and the form of other supplemental anti-inflammatory drugs. In embodiments where the active agent is growth factor, the dosage will depend on the safety and tolerability of the growth factor and the benefit outweighs the risk, and whether the growth factor is being used alone or in combination with other growth factor and growth factor inducing agent such as Omeprazole, in case of diabetes. Any of the subject formulations may be administered in a single dose or in divided doses. Dosages for the peptide/protein formulation of the present invention may be readily determined by techniques known to those of skilled in the art or as taught herein. Also, the present invention contemplates mixtures of one or more of the formulations of the present invention along with one or more antibiotics or other therapeutic agents. In particular embodiments, the carrier containing lysostaphin of the present invention may be administered along with any one or more of other antibiotics selected from: amoxicillin, ampicillin, azidocillin, azlocillin, aztreonam, bacitacin, benzathine benzylpenicillin, benzathine phenoxymethylpenicillin, benzylpenicillin (G), biapenem, carbenicillin, cefacetrile, cefadroxil, cefalexin, cefaloglycin, cefalonium, cefaloridine, cefalotin, cefapirin, cefatrizine, cefazedone, cefazaflur, cefazolin, cefradine, cefroxadine, ceftezole, cefaclor, cefamandole, cefminox, cefonicid, ceforanide, cefotiam, cefprozil, cefbuperazone, cefuroxime, cefuzonam, cephamycin (such as cefoxitin, cefotetan, cefmetazole), carbacephem (such as loracarbef), cefcapene, cefdaloxime, cefdinir, cefditoren, cefetamet, cefixime, cefmenoxime, cefodizime, cefoperazone, cefotaxime, cefpimizole, cefpiramide, cefpodoxime, cefsulodin, ceftazidime, cefteram, ceftibuten, ceftiolene, ceftizoxime, ceftriaxone, oxacephem (such as flomoxef, latamoxef), cefepime, cefozopran, cefpirome, cefquinome, ceftobiprole, chloramphenicol, chlorohexidine, clindamycin, clometocillin, cloxacillin, colistin, cycloserine, daptomycin, doripenem, doxycycline, epicillin, ertapenem, erythromycin, faropenem, fostomycin, gentamycin, imipenem, linezolid, mecillinam, meropenem, methicillin, meticillin, mezlocillin, minocycline, mupirocin, nafcillin, neomycin, oxacillin, panipenem, penamecillin, pheneticillin, phenoxymethylpenicillin (V), piperacillin, polymyxin, polymyxin B, procaine benzylpenicillin, propicillin, quinupristin/dalfopristin, ramoplanin, rifampicin, rifampin, sulbenicillin, teicoplanin, tigecycline, tigemonam, trimethoprim/sulfamethoxazole, and vancomycin. In particular embodiments, the carrier containing basic proteins of the present invention may be administered along with any one or more of other antibiotics selected from: aztreonam, bacitacin, ceftazidime, chloramphenicol, chlorohexidine, clindamycin, daptomycin, doxycycline, erythromycin, gentamycin, linezolid, methicillin, minocycline, mupirocin, neomycin, oxacillin, polymyxin, quinupristin/dalfopristin, rifampicin, rifampin, teicoplanin, temocillin, ticarcillin, tigecycline, trimethoprim/sulfamethoxazole, and vancomycin. In particular embodiments, the carrier containing basic proteins of the present invention may be administered along with any glycopeptide antibiotic in weight ratios of basic protein to glycopeptide antibiotic ranging from 0.1:1 to 20:1. In particular embodiments, the range of weight ratios is from 0.5:1 to 7:1. The glycopeptides antibiotic may be selected from the group consisting of vancomycin, teicoplanin and ramoplanin. The composition of the present invention may be in a form suitable for intravenous, intramuscular, subcutaneous, intraperitoneal, intrathecal or topical administration.

The present invention also pertains to a method of treating a staphylococcal infection in a human subject comprising: administering composition of the present invention comprising a carrier with anionic charge that electrostatically bound to lysostaphin; wherein lysostaphin is administered in an amount of from 1 mg to 150 mg/kg body weight/day to the human subject; and administering a beta-lactam antibiotic in an amount of from 50 to 250 mg/kg body weight/day to the human subject. The beta-lactam antibiotic may be administered along with the carrier and lysostaphin; such that the dose of beta-lactam in the human subject is antibiotic is from 100 to 200 mg/kg body weight/day. The beta-lactam antibiotic may be an penicillin, a cephalosporin, penem, a carbapenem, or a monobactam. The beta-lactam antibiotics that belong to penicillins include: aminopenicillins (such as amoxicillin, ampicillin, and epicillin); carboxypenicillins (such as carbenicillin, ticarcillin, temocillin); ureidopenicillins (azlocillin, piperacillin, mezlocillin); and others: (such as mecillinam, sulbenicillin, benzylpenicillin (G), azidocillin, penamecillin, clometocillin, benzathine benzylpenicillin, procaine benzylpenicillin, phenoxymethylpenicillin (V), propicillin, benzathine, phenoxymethylpenicillin, pheneticillin, oxacillin, cloxacillin, meticillin, nafcillin). The beta-lactam antibiotics that belong to cephalosporins are: cefacetrile, cefadroxil, cefalexin, cefaloglycin, cefalonium, cefaloridine, cefalotin, cefapirin, cefatrizine, cefazedone, cefazaflur, cefazolin, cefradine, cefroxadine, ceftezole, cefaclor, cefamandole, cefminox, cefonicid, ceforanide, cefotiam, cefprozil, cefbuperazone, cefuroxime, cefuzonam, cephamycin, carbacephem, cefcapene, cefdaloxime, cefdinir, cefditoren, cefetamet, cefixime, cefmenoxime, cefodizime, cefoperazone, cefotaxime, cefpimizole, cefpiramide, cefpodoxime, cefsulodin, ceftazidime, cefteram, ceftibuten, ceftiolene, ceftizoxime, ceftriaxone, oxacephem, cefepime, cefozopran, cefpirome, cefquinome, and ceftobiprole. The beta-lactam antibiotics that belong to carbopenems are: biapenem, doripenem, ertapenem, imipenem, meropenem, and panipenem. The beta-lactam antibiotics that is penem is faropenem.

In certain embodiments, the dosage of a peptide/protein formulation will generally be in the range of about 0.01 ng to about 1000 mg of basic protein per kg body weight, specifically in the range of about 1 ng to about 100 mg of basic protein per kg, and more specifically in the range of about 100 ng to about 20 mg of basic protein per kg. The more preferable dose range will be about 100 ng to about 20 mg of basic protein per kg. The amount of peptide/protein relative to the weight of the carrier in a formulation may be in the range of about 1% to 1000% of the weight of the carrier. In one embodiment, the amount of basic protein relative to the weight of the carrier in a formulation may be in the range of about 5% to 500% of the weight of the carrier. In other embodiments, the amount of basic protein relative to the weight of the carrier in a formulation may be in the range of about 10% to 100% of the weight of the carrier.

An effective dose or amount, and any possible affects on the timing of administration of the formulation, may need to be identified in the present invention. This may be accomplished by routine experiment as described herein, using one or more groups of animals (preferably at least 5 animals per group), or in human trials if appropriate. The effectiveness of the peptide/protein formulation may be assessed by administering and assessing the effect of the administration by measuring one or more indices associated with the disease/disorder/infection of interest, and comparing the post-treatment values of these indices to the values of the same indices prior to treatment.

The precise time of administration and amount of any particular compound that will yield the most effective treatment in a given subject will depend upon the activity, pharmacokinetics, and bioavailability of the basic protein, physiological condition of the subject (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

Treatment may be initiated with smaller dosages which are less than the optimum dose of the compound. Thereafter, the dosage may be increased by small increments until the optimum therapeutic effect is attained.

The combined use of the lysostaphin formulation of the present invention with other antibiotics or other therapeutic agents may reduce the required dosage for the lysostaphin formulation. This is because the effect of other antibiotics or other therapeutic agents may be complimentary to the effect of the lysostaphin formulation. In such combined therapy, the different active agents may be delivered together or separately, and simultaneously or at different times within the day.

Toxicity and therapeutic efficacy of the antibacterial peptide/protein formulation of the present invention may be determined by standard pharmaceutical procedures in cell cultures or experimental animals, e.g., for determining the $LD_{50}$, $ED_{50}$, MIC (Minimum concentration of the product that will still inhibit the growth of a test microorganism), and/or MBC (Minimum concentration of the product that will kill a- or bacteriocidal to a test organism). Formulations that exhibit large therapeutic indices are preferred. Although formulations that exhibit toxic side effects may be used, care should be taken that the carrier-antibacterial peptide/protein complex accumulates at the desired site in order to reduce side effects.

The data obtained from the cell culture assays and animal studies may be used in formulating a range of dosage for use in humans. It is important that the dosage of any carrier-antibacterial peptide/protein complex formulations provides a range of circulating concentrations in the blood that is above MIC with little or no toxicity. The dosage may vary within this range depending upon the dosage form employed and the route of administration utilized. For agents of the present invention, the therapeutically effective dose may be estimated initially from bacterial culture assays to obtain the MIC and the MBC. A dose of the formulation may be derived from animal models based on the dose that gives a circulating plasma concentration range above MIC and/or MBC as determined in cell culture. Such information may be used to more accurately determine useful doses in humans.

The carrier-antibacterial peptide/protein complex of the present invention may be used for external administration in a form of ointment, paste, cream or gels and may further contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

The carrier with basic proteins of the present invention may be used for external administration in a form of powder or spray and may further contain excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

The carrier-peptide/protein complex of the present invention may be used for external administration in a form of aerosol. This is accomplished by preparing an aqueous aerosol, liposomal preparation or solid particles containing the composition of the present invention but not covalently bonded to the solid. A non-aqueous (e.g., fluorocarbon propellant) suspension could be used. Sonic nebulizers may be used because they minimize exposing the agent to shear, which may result in degradation of the compound. Ordinarily, an aqueous aerosol is made by formulating an aqueous solution or suspension of the formulation together with conventional pharmaceutically acceptable carriers and stabilizers. The excipients and stabilizers vary with the requirements of the particular compound, but typically include non-ionic surfactants (Tweens, Pluronics, or polyethylene glycol), innocuous proteins like serum albumin, sorbitan esters, oleic acid, lecithin, aminoacids such as glycine, buffers, salts, sugars or sugar alcohols. Aerosols generally are prepared from isotonic solutions.

Pharmaceutical compositions comprising carrier-peptide/protein complex of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous excipients which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Kits

This invention also provides kits for conveniently and effectively implementing the methods of this invention. Such kits comprise any of the carrier-peptide/protein complex of the present invention or a combination thereof, and a means for facilitating compliance with methods of this invention. Such kits, in the case of carrier-peptide/protein complex formulations, provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use. The sample can be liquids from many sources including serum, plasma, whole blood, urine, tissue extract, bacterial extracts, viral extracts, fungal extracts, or any samples in which the presence of basic proteins (for example lysostaphin) is suspected or needed to be quantified.

In one aspect, the present invention relates to a kit comprising a composition comprising: (i) a polymeric backbone (ii) an anionic group of sulfate, sulfonate, or phosphate moiety covalently linked or bonded to the backbone; (iii) an active agent with positively charge groups electrostatically bound to the anionic group ion; and (iii) a protective chain covalently linked or bonded to the backbone. Uses for such kits include, for example, therapeutic applications. Such kits may have a variety of other uses, including, for example, imaging, targeting, diagnosis, therapy, vaccination, and the like.

EXAMPLES

The invention is further illustrated by the following Examples. The Examples are provided for illustrative purposes only, and are not to be construed as limiting the scope or content of the invention in any way.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

While preferred embodiments of the present invention have been shown and described herein, it will be obvious to those skilled in the art that such embodiments are provided by way of example only. It should be understood that apparent alternatives to the embodiments of the invention described herein may be employed in practicing the invention.

Examples of Compositions with Polymeric Backbones Derived from Polysaccharides

Example 1: Synthesis of HPPEG52g 2 g of MPEGAM (MW=5 kDa; 0.4 mmol; Lysan; lot #111-102; clear in soln) was dissolved in 10 ml of water and 5 ml of 1M HEPES pH 7.3 and 100 μl 10N NaOH added to bring pH to 7.8. The amino group was measured by TNBS and was found to be 0.579 mmol NH2 total in 2 g. In a separate container, 1 g of Heparin sodium salt (25 kDa by size exclusion chromatography using globular protein standards, Cat #41121-1G Acros. Lot #B0128763; MW=~593+4sodium−4H=681 Da/disaccharide; 1 g of HP has 1.47 mmol of theoretical Carboxyl group assuming no substitution at the carboxyl) was dissolved to 5 ml of water (total volume). The amino group was measured by TNBS and was found to be negligible 2.6 μmol total per gram. This HP solution (5 ml) was activated for 20 minutes by adding 80 mg of NHSS (MW=115.14; 0.7 mmol) and 285 mg EDC (MW=191.71; 1.5 mmol). This was then added to the MPEGAM solution and allowed to react for 3 hours. After 3 hours, the amino group was measured and found to be 192 μmol total, indicating 67% of MPEG were used up Amino group was measured again the next day and found to be 84 μmol total, indicating 85% of PEG were used up. The reaction mixture was washed with 15 changes of 1M NaCl and 10 changes of water in a 50,000 MWCO ultrafiltration cartridge (UFP-50-E-5A). Sample HPPEG52g was filter-sterilized (0.2 μm polysulfone filter, Nalgene, Rochester, N.Y.) and lyophilized yielding 1.86 grams. One mg/ml was analyzed and contain 0+/−5 uM $NH_2$ or 0 nmol/mg. Ten mg/ml was measured for GPC and showed a retention time of 14 min (approx 11.5 nm).

Example 2: Synthesis of HPPEG104G 4 g of MPEGAM (MW=10 kDa; 0.4 mmol; Sunbio; lot #C1AM-010-05053) was dissolved to 10 ml of water and 5 ml of 1M HEPES pH 7.3 and 100 ul 10N NaOH added to bring pH to 7.8. The amino group was measured by TNBS and was found to be 0.528 mmol $NH_2$ total in 4 g. There seems to be more amino groups than expected perhaps MPEGAM has smaller molecular weight. In a separate container, 1 g of Heparin sodium salt (25 kDa by size exclusion chromatography using globular protein standards, Cat #41121-1G Acros. Lot #B0128763; MW=~593+4sodium−4H=681 Da/disaccharide; 1 g of HP has 1.47 mmol of theoretical Carboxyl group assuming no substitution at the carboxyl) was dissolved to 5 ml of water (total volume). The amino group was measured by TNBS and was found to be negligible 2.2 μmol total per gram. This HP solution (5 ml) was activated for 20 minutes by adding 80 mg of NHSS (MW=115.14; 0.7 mmol) and 285 mg EDC (MW=191.71; 1.5 mmol). This was then added to the MPEGAM solution and allowed to react for 3 hours. After 3 hours, the amino group was measured and found to be 152 μmol total, indicating 71% of MPEG were used up. Amino group was measured again the next day and found to be 58 μmol total, indicating 89% of PEG were used up. The reaction mixture was washed with 15 changes of 1M NaCl and 10 changes of water in a 50,000 MWCO ultrafiltration cartridge (UFP-50-E-5A). Sample HPPEG52g was filtered (using #5 filter paper from Fisher) and lyophilized yielding 2.05 grams. One mg/ml was analyzed and contain 0+/−5 uM $NH_2$ or 0 nmol/mg. Ten mg/ml was measured for GPC and showed a retention time of 13.2 min (approx 17 nm).

Example 3: Synthesis of 50CSPEG106G

This composition has chondroitin sulfate or CS (shark origin from Fisher Scientific, Pittsburgh, Pa. Cat #21355, MW=50 kDa) as the polymeric backbone with the carboxyl groups reacted with 6 grams of 10 kDa MPEGAM (MW=10 kDa MPEG with amino group at the terminal; Sunbio, Orinda, Calif.; Cat #P1AM-10)/gram of CS. This composition contains anionic groups capable of binding peptide/proteins or small molecule with pI greater than 7. Further, the remaining carboxyl groups can further be modified to contain more sulfate, sulfonate or phosphate groups. 50CSPEG106G was made as follows; 6 g of MPEGAM (MW=10 kDa MPEG with amino group at the terminal; Sunbio, Orinda, Calif.; Cat #P1AM-10) dissolved in 20 ml of 80% ethanol, 5 ml of 1M HEPES was added to the solution and the pH was adjusted to pH 7.8 using 10N NaOH. The amino group was measured by TNBS and was found to be 0.91 mmol. In a separate container, 1 gram of CS was dissolved in 8 ml water, to obtain a CS solution and the carboxyl groups were activated by adding 115 mg of NHS (MW=115.14; 1 mmol), followed by 575 mg EDC (MW=191.71; 3 mmol). After 20 minutes of activation, this was added directly to the MPEGAM. After 2 hours, the total amino group was found to be 0.24 mmol indicating 74% of MPEG was incorporated. The reaction mixture was concentrated to 100 ml and washed with 15 changes of water in a 100 kDa MWCO ultrafiltration cartridge (UFP-100-E-5A). The 50CSPEG106G sample was filter-sterilized (0.2 μm polysulfone filter, Nalgene, Rochester, N.Y.) and lyophilized yielding 2.4 grams. One mg/ml was analyzed and contain 4.8+/−5 μM NH2 or 4.8 nmol/mg. Ten mg/ml of 50CSPEG106G was analyzed by Size Exclusion chromatography using TosohG4000WXL and showed a retention time of 10.7 min (approx 29.8 nm).

Example 4: Synthesis of 50CSPEG106GNTA

The resulting 50CSPEG106G (see above) can be converted to 50CSPEG106GNTA and then to 50CSPEG106GNTASO (see below). The resulting 50CSPEG106G (see above) can be converted to 50CSPEG106GNTA as follows: Measure the remaining carboxyl groups of 2.4 grams of 50CSPEG106G according to the protocol by Kobayahi and Chiba (Analytical biochemistry 1994, vol 219, p 189-194). To synthesize 50CSPEG106G, take 2.4 g of 50CSPEG106G (with 1 equivalent carboxyl group) and dissolve in 25 ml of 20 mM MES (2-(N-morpholino)ethanesulfonic acid, Pierce, Rockford, Ill.) buffer pH 4.7 to obtain 50CSPEG106G solution. Add 1 equivalent of NHS and 2 equivalents EDC (MW=191.71) and activate for 20 minutes. After 20 minutes add this activated 50CSPEG106G solution to 10 equivalents of Nalpha,Nalpha-biscarboxymethyl-lysine (MW=262 Da) in to 25 ml of 1M HEPES buffer at pH 7.4 and allow to react overnight. Concentrate the reaction mixture to 100 ml and wash with 15 changes of water in a 100 kDa-MWCO ultrafiltration cartridge (UFP-100-E-5A). Filter-sterilize the 50CSPEG106GNTA product (using 0.2 μm polysulfone filter, Nalgene, Rochester, N.Y.) and lyophilize. Make 10 mg/ml solution of resulting 50CSPEG106GNTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should consistent with diameter of approx 30-40 nm.

Example 5: Synthesis of 50CSPEG106GNTASO or 50CSPEG106GNTASF or 50CSPEG106GNTAPO This structure comprises 50 kDa chondroitin sulfate with the carboxyl groups reacted with 6 grams of 10 kDa MPEG and the remaining carboxyl groups covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the chondroitin sulfate backbone. The 50CSPEG106GNTA (see above) can be converted to sulfated (or sulfonated, or phosphorylated) carrier containing clusters of sulfate (or sulfonate, or phosphate) groups with up to three sulfate (or sulfonate, or phosphate) groups in each cluster. To do this, take 2 grams of the 50CSPEG106GNTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, keep pH at 7.3 using NaOH) and measure the starting amino groups by TNBS (Spadaro et al., 1979, Anal. Chem., 96, p 317-329) which should be around 2.6 mmol, depending on the purity of AES (or SNA or OPE). Add the activated carrier to the AES (or SNA or OPE) solution and stir the solution overnight. Measure the amino groups by TNBS to determine the amount of decrease in amino groups which is equivalent to the amount of sulfate (or sulfonate, or phosphate) groups incorporated. Wash the sulfated (or sulfonated, or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize (50CSPEG106GNTASO, or 50CSPEG106GNTASF, or 50CSPEG106GNTAPO). This product will have clusters of up to three sulfate (or sulfonate, or phosphate) groups per cluster that is pendant to the backbone.

Example 6: Synthesis of 14HPPEG104G

This composition has 14 kDa Heparin ((H4784-1G Sigma. Lot #047K1195; MW 14 kDa; 1 g has 0.827 mmol carboxyl groups) as the polymeric backbone with the carboxyl groups reacted with 4 grams of 10 kDa MPEGAM (MW=10 kDa MPEG with amino group at the terminal; Sunbio, Orinda, Calif.; Cat #P1AM-10). This composition contains anionic groups capable of binding peptide/proteins or small molecule with pI greater than 7. Further, the remaining carboxyl groups can further be modified to contain more sulfate, sulfonate or phosphate groups. The 14HPPEG104G was prepared as follows: A) 1 g of Heparin (HP) sodium salt (H4784-1G Sigma. Lot #047K1195; 1 g of HP has 0.827 mmol of Carboxyl group) was dissolved in 8 ml of water (HP solution). B) In a separate container, 4 g of MPEG-AM (MW=10000; 0.4 mmol; Sunbio; lot #C1AM-010-05053; clean in soln) was dissolved in 15 ml of 80% ethanol and the HP solution were added directly to the MPEG-AM. C) The reaction was made up to 20 mM MES pH=4.7 with addition of water to clear up the precipitate. The reaction was initiated by addition of 80 mg of NHS (MW=115.14; 0.7 mmol) and 380 mg EDC (MW=191.71; 2 mmol) and stirred for 20 minutes. After 20 minutes, 4 ml of 1M HEPES was added to the solution and the pH was adjusted to pH 7.8 slowly with 10N NaOH one drop at a time, and allowed to react overnight. Aliquot was taken to determine the remaining amino groups from the MPEG-AM and determine the MPEG incorporated. The amino group was found to 0.011 mmol total indicating all MPEG was incorporated (14HPPEG104G). D) The reaction mixture was concentrated to 100 ml and washed with 20 changes of water in 100,000 MWCO ultrafiltration cartridge (UFP-100-E-5A), filter-sterilized (0.2 μm polysulfone filter, Nalgene, Rochester, N.Y.) and lyophilized yielding 2.4 grams. One mg/ml was analyzed and contain 0+/−5 uM $NH_2$ or 0 nmol/mg. E) Size Exclusion chromatography using TosohG4000WXL column (0.79×30 cm) eluted with phosphate buffered saline (PBS; 11.9 mM phosphate, 137 mM NaCl, 2.7 mM $KPO_4$, pH 7.4) containing 15% Acetonitrile at a flow rate of 0.6 ml/min showed a retention time of 12.7 min (approx 13.8 nm).

Example 7: Synthesis of 14HPPEG104GNTA

The resulting 14HPPEG104G (see above) can be converted to 14HPPEG104GNTA and then to of 14HPPEG104GNTASO, 14HPPEG104GNTASF, or 14HPPEG104GNTAPO (see below). The resulting 14HPPEG104G (see above) can be converted to 14HPPEG104GNTA as follows: Measure the remaining carboxyl groups of 2.4 grams of 14HPPEG104G according to the protocol by Kobayahi and Chiba (Analytical biochemistry 1994, vol 219, p 189-194). To synthesize 14HPPEG104GNTA, take 2.4 g of 14HPPEG104G carboxyl group) and dissolve in 25 ml of 20 mM MES (2-(N-morpholino)ethanesulfonic acid, Pierce, Rockford, Ill.) buffer pH 4.7 to obtain 14HPPEG104G solution. Add 1 equivalent of NHS and 2 equivalents EDC (MW=191.71) and activate for 20 minutes. After 20 minutes add this activated 14HPPEG104G solution to 10 equivalents of Nalpha,Nalpha-biscarboxymethyl-lysine (MW=262 Da) in to 25 ml of 1M HEPES buffer at pH 7.4 and allow to react overnight. Measure the remaining amino groups to determine the extent of NTA incorporation. Concentrate the reaction mixture to 100 ml and wash with 15 changes of water in a 100 kDa-MWCO ultrafiltration cartridge (UFP-100-E-5A). Filter-sterilize the 14HPPEG104GNTA product (using 0.2 μm polysulfone filter, Nalgene, Rochester, N.Y.) and lyophilize. Make 10 mg/ml solution of resulting 14HPPEG104GNTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should consistent with diameter of approx 15-20 nm.

Example 8: Synthesis of 14HPPEG104GNTASO or 14HPPEG104GNTASF or 14HPPEG104GNTAPO This structure comprises of 14 kDa heparin in which 27% of theoretical carboxyl groups are covalently linked to 10 kDa MPEG and the remaining carboxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the heparin backbone (other backbones can also be used). To do this, take 2 grams of the 14HPPEG104GNTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, keep pH at 7.3 using NaOH) and measure the starting amino groups by TNBS (Spadaro et al., 1979, Anal. Chem., 96, p 317-329) which should be around 2.6 mmol, depending on the purity of AES (or SNA, or OPE). After 20 minutes, add the activated carrier to the AES (or SNA, or OPE) solution. After overnight reaction measure the amino groups by TNBS to determine the amount of decrease in amino groups which is equivalent to the amount of sulfate (or sulfonate, or phosphate) groups incorporated. Wash the sulfated (or sulfonated, or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize (14HPPEG104GNTASO or 14HPPEG104GNTASF or 14HPPEG104GNTAPO). This product will have clusters of up to three sulfate (or sulfonate, or phosphate) groups per cluster pendant to the backbone.

Example 9: Synthesis of 1000HYPEG1035NTA

This will be used as starting materials for the synthesis of some of the anionic core compositions of the present invention. This composition has hyaluronic acid or HY (Sigma Chem. Co. St Luis Mo. Cat #53747, MW=1000 kDa) as the polymeric backbone with 35% of theoretical carboxyl groups replaced with 10 kDa MPEGAM (MW=10 kDa MPEG with amino group at the terminal; Sunbio, Orinda, Calif.; Cat #P1AM-10) and the remaining carboxyl groups occupied with nitrilotriacetic acid. To do this the Hyluronic acid can be used without addition of more carboxyl groups or additional carboxyl groups can be added. To add additional carboxyl groups, the hydroxyl groups in hyaluronan can be converted to carboxy groups according to the protocol by Tijsen et al. (Carbohydrate Polymers 2001, vol 45; p 219-226). At the end of Tijsen et al. protocol the carboxymethylated hyaluronan is washed with 15 changes of water in a 3 kDa-MWCO ultrafiltration cartridge (UFP-3-E-5A). Filter-sterilize the resulting product using (0.2 um polysulfone filter, Nalgene, Rochester, N.Y.) and lyophilize to obtain hyaluronan with extra carboxyl groups. Before synthesis of 1000HYPEG1035NTA, measure the starting carboxyl group (1 equivalent) of 1.0 g HY (this could be HY without additional carboxyl groups or that modified to have additional carboxyl groups) according to the protocol by Kobayahi and Chiba (Analytical biochemistry 1994, vol 219, p 189-194). To synthesize 1000HYPEG1035NTA, take 1.0 g of HY (with 1 equivalent carboxyl group) and dissolve in 25 ml of 20 mM MES (2-(N-morpholino)ethanesulfonic acid, Pierce, Rockford, Ill.) buffer pH 4.7 to obtain HY solution. Dissolve 0.35 equivalents of MPEGAM (MW=10 kDa MPEG with amino group at the terminal; Sunbio, Orinda, Calif.; Cat #P1AM-10) in 20 ml of 80% ethanol and add to the HY solution to make HYPEG solution. To the HYPEG solution, add 1 equivalent of NHS (MW=115.14) and 1 equivalent EDC (MW=191.71) solution while stirring. Maintain the pH at pH 4.7-5.0 with 6N HCl for 20 minutes using HCl. After 20 minutes of activation, adjust the pH to 7.8 by adding 10 ml of 1M HEPES, pH 7.4 and further adjust pH with 10N NaOH one drop at a time to reach 7.8. Allow the reaction to proceed for 2 hours and measure the remaining amino group of the MPEGAM by TNBS and should be none indicating that all 0.35 equivalents amino group is used up and conjugated to the HY. If there are remaining amino group in add 1 equivalent EDC (MW=191.71), and allow to react overnight to form 1000HYPEG1035. Take an aliquot of the resulting 1000HYPEG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with diameter of approx 30-50 nm. Adjust pH down to 5 with 6N HCl and add 1.5 equivalents EDC (MW=191.71) and activate for 20 minutes. After 20 minutes add this activated 1000HYPEG1035 solution to 10 equivalents of Nalpha,Nalpha-biscarboxymethyllysine (MW=262 Da) in to 25 ml of 1M HEPES buffer at pH 7.4 and allow to react overnight. Concentrate the reaction mixture to 100 ml and wash with 15 changes of water in a 100 kDa-MWCO ultrafiltration cartridge (UFP-100-E-5A). Filter-sterilize the 1000HYPEG1035NTA product (using 0.2 μm polysulfone filter, Nalgene, Rochester, N.Y.) and lyophilize. Make 10 mg/ml solution of resulting 1000HYPEG1035NTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should be consistent with diameter of approx 30-70 nm.

Example 10: Synthesis of 1000HYPEG1035NTASO or 1000HYPEG1035NTASF or 1000HYPEG1035NTAPO This structure comprises of 1000 kDa hyuronic acid in which 35% of theoretical carboxyl groups are covalently linked to 10 kDa MPEG and the remaining carboxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the hyuronic acid backbone (other backbones can also be used). The 1000HYPEG1035NTA (see above) can be converted to contain sulfate (or sulfonate, or phosphate) with up to three sulfate (or sulfonate, or phosphate) groups in each cluster. To do this, take 2 grams of the 1000HYPEG1035NTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, keep pH at 7.3 using NaOH) and measure the starting amino groups by TNBS (Spadaro et al., 1979, Anal. Chem., 96, p 317-329) which should be around 2.6 mmol, depending on the purity of AES (or SNA or OPE). After 20 minutes, add the activated carrier to the AES (or SNA, or OPE) solution. After overnight reaction measure the amino groups by TNBS to determine the amount of decrease in amino groups which is equivalent to the amount of sulfate (or sulfonate, or phosphate) groups incorporated. Wash the sulfated (or sulfonated, or phosphorylated) carrier by 20 volumes of water using a 100 kDa MWCO ultrafiltration cartridge (UFP-100-E-5A; GE-Amersham), filter-sterilize (0.2 um polysulfone filter, Nalgene, Rochester, N.Y.) and lyophilize (1000HYPEG1035NTASO or 1000HYPEG1035NTASF or 1000HYPEG1035NTAPO). This product will have clusters of up to three sulfate (or sulfonate, or phosphate) groups per cluster that is pendant to the backbone.

Example 11: Synthesis of 60PGAPEG1035NTA

This will be used as starting materials for the synthesis of some of the anionic core compositions of the present invention. This composition has pectin or polygalacturonic acid (Sodiumpolypectate; Sigma Chem. Co. St Luis Mo. Cat #p3889, MW=60 kDa) as the polymeric backbone with 35% of theoretical carboxyl groups replaced with 10 kDa MPEGAM (MW=10 kDa MPEGAM has amino group at the terminal; Sunbio, Orinda, Calif.; Cat #P1AM-10) and the remaining carboxyl groups occupied with nitrilotriacetic acid. The modification of 60PGAPEG1035NTA into 60PGAPEG1035NTASO, 60PGAPEG1035NTASF, and 60PGAPEG1035NTAPO; where SO, SF, and PO are sulfate, sulfonate, and phosphate covalently linked to the carbonyl groups of NTA; is as described above for other NTA containing compositions. To make 60PGAPEG1035NTA, the starting pectin can be used without addition of more carboxyl groups or additional carboxyl groups can be added. To add additional carboxyl groups, the hydroxyl groups in hyaluronan can be converted to carboxy groups according to the protocol by Tijsen et al. (Carbohydrate Polymers 2001, vol 45; p 219-226). At the end of Tijsen et al. protocol the carboxymethylated pectin is washed with 15 changes of water in a 3 kDa-MWCO ultrafiltration cartridge (UFP-3-E-5A). Filter-sterilize the resulting product (PMA) using (0.2 um polysulfone filter, Nalgene, Rochester, N.Y.) and lyophilize to obtain pectin with extra carboxyl groups. Occasionally, pectin will have significant percent of the carboxyl group blocked with methyl groups. This can be removed using acid to expose all carboxyl groups of pectin. Briefly, dissolve 2 g of pectin in 100 water and adjust the pH to 0.5 using concentrated HCl and keep at 80° C. for 2 hours according to Constenla and Lazano (Latin American Applied Research 2003, vol 33, p 91-96). Neutralize with NaOH and wash 15 changes of water in a 3 kDa-MWCO ultrafiltration cartridge (UFP-3-E-5A). Filter-sterilize the resulting product using (0.2 um polysulfone filter, Nalgene, Rochester, N.Y.) and lyophilize. This pectin can be processed to increase the amount of carboxyl groups as described above.

60PGAPEG1035NTA can be made using any of the pectin (PGA) described above, unprocessed or processed to increase carboxyl group. Before synthesis of 60PGAPEG1035NTA, measure the starting carboxyl group (1 equivalent) of 1.0 g PGA (this could be PGA without additional carboxyl groups or PGA modified to have additional carboxyl groups) according to the protocol by Kobayahi and Chiba (Analytical biochemistry 1994, vol 219, p 189-194). To synthesize 60PGAPEG1035NTA, take 1.0 g of PGA (with 1 equivalent carboxyl group) and dissolve in 50 ml of 20 mM MES (2-(N-morpholino) ethanesulfonic acid, Pierce, Rockford, Ill.) buffer pH 4.7 to obtain PGA solution. Dissolve 0.35 equivalents of MPEGAM (MW=10 kDa MPEG with amino group at the terminal; Sunbio, Orinda, Calif.; Cat #P1AM-10) in 20 ml of 80% ethanol and add to the PGA solution to make PGAPEG solution. To the PGAPEG solution, add 1 equivalent 1 of NHS (MW=115.14) and 1 equivalent EDC (MW=191.71) solution while stirring. Maintain the pH at pH 4.7-5.0 with 6N HCl for 20 minutes using HCl. After 20 minutes of activation, adjust the pH to 7.8 by adding 10 ml of 1M HEPES, pH 7.4 and adjust pH to 7.8 with 10N NaOH one drop at a time. Allow the reaction to proceed for 2 hours and measure the remaining amino group of the MPEGAM by TNBS and should be none indicating that all 0.35 equivalents amino group is used up and conjugated to the PGA. If there are remaining amino group in MPEGAM, adjust pH to 5 with 6N HCl and add 1 equivalent EDC (MW=191.71), after 20 minutes adjust back the pH to 7.8 and allow to react overnight to form 60PGAPEG1035. Take an aliquot of the resulting 60PGAPEG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with diameter of approx 18-30 nm. Adjust pH down to 5 with 6N HCl and add 1.5 equivalents EDC (MW=191.71) and activate for 20 minutes. After 20 minutes add this activated 60PGAPEG1035 solution to 10 equivalents of Nalpha,Nalpha-biscarboxymethyl-lysine (MW=262 Da) in to 25 ml of 1M HEPES buffer at pH 7.4 and allow to react overnight. Concentrate the reaction mixture to 100 ml and wash with 15 changes of water in a 100 kDa-MWCO ultrafiltration cartridge (UFP-100-E-5A). Filter-sterilize the 60PGAPEG1035NTA product (using 0.2 μm polysulfone filter, Nalgene, Rochester, N.Y.) and lyophilize. Make 10 mg/ml solution of resulting 60PGAPEG1035NTA and determine the hydrodynamic diameter by size exclusion chromatography using TosohG4000WXL column (0 79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should consistent with diameter of approx 20-40 nm.

Example 12: Synthesis of 30CHIPEG1035DTPA

This will be used as starting materials for the synthesis of some of the anionic core compositions of the present invention. This composition has chitosan (Sigma Chem. Co. St Luis Mo. Cat #448869, MW=35 kDa) as the polymeric backbone with 35% of theoretical amino groups occupied with 10 kDa MPEGC (MW=10 kDa; MethoxyPEG with carboxyl group at the terminal, from Lysan bio; Arab, Ala.) and the remaining amino group occupied with diethyenediaminepentaacetic acid (DTPA). The modification of 30CHIPEG1035DTPA into 30CHIPEG1035DTPASO, 30CHIPEG1035DTPASF, and 30CHIPEG1035DTPAPO; where SO, SF, and PO are sulfate, sulfonate, and phosphate covalently linked to the carbonyl groups of DTPA; is as described above for other carboxyl containing composition. To synthesize 30CHIPEG1035DTPA, take 1.0 g of chitosan hydrochloride (with 1 equivalents amino group as measured by TNBS) and dissolve in 25 ml of 1M HEPES buffer at pH 7.4 (Pierce, Rockford, Ill.) to obtain a 30CHI solution. In a separate container, dissolve 0.35 equivalents of MPEGC (MW=10 kDa; MethoxyPEG with carboxyl group at the terminal, from Lysan bio; Arab, Ala.) in 60 ml of 80% ethanol with 20 mM MES pH=4.7 (12000 of 1M MES added to 60 ml), add 0.5 equivalents of NHS (MW=115.14), once dissolved add 1 equivalent EDC (MW=191.71; 10.43 mmol) while stirring and allow the activation to proceed for 20 minutes. Add activated MPEGC directly to 30CHI solution, allow for the reaction to accrue for 2 hours and measure amino groups by TNBS to insure if 35% saturation of amino groups else add more of the appropriate amount of activated MPEGC. This is the 30CHIPEG1035 solution. Perform size exclusion chromatography using TosohG4000WXL column (0 79×30 cm) with phosphate buffered saline (PBS; 11.9 mM phosphate, 137 mM NaCl, 2.7 mM $KPO_4$, pH 7.4) containing 15% Acetonitrile elution at a flow rate of 0.6 ml/min. The retention time of should be consistent with approximately 14-17 nm molecular diameter. Add 5 equivalents DTPA dianhydride (MW=357; Sigma Chem. Co., St Louis, Mo. Cat #D6148) followed by 2004 TEA. Titrate the reaction slowly with 10 N NaOH to pH 7.1 and stir for 4 hours. Using TNBS reaction, confirm that no amino groups remain indicative of a complete reaction, and that the 30CHIPEG1035DTPA product is made. Perform size exclusion chromatography using TosohG4000WXL column (0.79×30 cm) with phosphate buffered saline (PBS; 11.9 mM phosphate, 137 mM NaCl, 2.7 mM $KPO_4$, pH 7.4) containing 15% Acetonitrile elution at a flow rate of 0.6 ml/min. The retention time should be consistent with 17-21 nm molecular diameter. Wash the resulting 30CHIPEG1035DTPA with 15 volumes of water using a 100,000 MWCO ultrafiltration cartridge (UFP-100-E-5A; GE-Amersham) and lyophilize.

Example 13: Synthesis of 40DXPEG1035NTA

This will be used as starting materials for the synthesis of some of the anionic core compositions of the present invention. This composition has dextran or polyglucose (alpha 1-6 with alpha 1-4 branch; Sigma Chem. Co. St Luis Mo. Cat #31389, MW=40 kDa) as the polymeric backbone with 35% of the hydroxyl groups derivatized with 10 kDa MPEGAM (MW=10 kDa MPEGAM has amino group at the terminal; Sunbio, Orinda, Calif.; Cat #P1AM-10) and the remaining hydroxyl groups occupied with nitrilotriacetic acid. The modification of 40DXPEG1035NTA into 40DXPEG1035NTASO, 40DXPEG1035NTASF, and 40DXPEG1035NTAPO; where SO, SF, and PO are sulfate, sulfonate, and phosphate covalently linked to the carbonyl groups of NTA; is as described above for other carboxyl containing compositions. To make 40DXPEG1035NTA, the starting dextran hydroxyl groups are converted to carboxyl groups. To add carboxyl groups, the hydroxyl groups in dextran can be converted to carboxy groups according to the protocol by Tijsen et al. (Carbohydrate Polymers 2001, vol 45; p 219-226). Briefly, suspend 10 gram of dextran 100 ml of 90% propanol/water and add 4 grams NaOH pellet and stir overnight at 40° C. The next day add 10 grams of sodiummonochloroacetate (Sigma Chem Co. St Luis, Mo. Cat #291773) as outlined in Tijsen et al. (Carbohydrate Polymers 2001, vol 45; p 219-226). At the end of the reaction the carboxymethylated dextran is washed with 15 changes of water in a 3 kDa-MWCO ultrafiltration cartridge (UFP-3-E-5A). Filter-sterilize the resulting product (DX) using (0.2 μm polysulfone filter, Nalgene, Rochester, N.Y.) and lyophilize to obtain carboxymethylated dextran. Before synthesis of 40DXPEG1035NTA, measure the starting carboxyl group (1 equivalent) of 1.0 g DX according to the protocol by Kobayahi and Chiba (Analytical biochemistry 1994, vol 219, p 189-194). To synthesize 40DXPEG1035NTA, take 1.0 g of DX (with 1 equivalent carboxyl groups) and dissolve in 50 ml of 20 mM MES (2-(N-morpholino)ethanesulfonic acid, Pierce, Rockford, Ill.) buffer pH 4.7 to obtain a DX solution. Dissolve 0.35 equivalent of MPEGAM (MW=10 kDa MPEG with amino group at the terminal; Sunbio, Orinda, Calif.; Cat #P1AM-10) in 20 ml of 80% ethanol and add to the DX solution to make DXPEG solution. To the DXPEG solution, add 1 equivalent of NHS (MW=115.14) and 1 equivalent EDC (MW=191.71) solution while stirring. Maintain the pH at pH 4.7-5.0 with 6N HCl for 20 minutes using HCl. After 20 minutes of activation, adjust the pH to 7.1 by adding 10 ml of 1M HEPES, pH 7.4. If pH is below 7.1 adjust pH with 10N NaOH one drop at a time to reach 7.1. Allow the reaction to proceed for 2 hours and measure the remaining amino group of the MPEGAM by TNBS and should be none indicating that all 0.35 equivalents amino group is used up and conjugated to the PGA. If there are remaining amino groups in MPEGAM, adjust pH to 5 with 6N HCl and add 1 equivalent EDC (MW=191.71), after 20 minutes adjust back the pH to 7.1 and allow to react overnight to form 40DXPEG1035. Take an aliquot of the resulting 40DXPEG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM KPO4, pH 7.4) containing 15% Acetonitrile as elution solvent at a flow rate of 0.6 ml/min. The retention time should be consistent with diameter of approx 14-20 nm. Adjust pH down to 5 with 6N HCl and add 1.5 equivalents EDC (MW=191.71) and activate for 20 minutes. After 20 minutes add this activated 40DXPEG1035 solution to 10 equivalents of Nalpha,Nalpha-biscarboxymethyl-lysine (MW=262 Da) in to 25 ml of 1M HEPES buffer at pH 7.4 and allow to react overnight. Concentrate the reaction mixture containing 40DXPEG1035NTA to 100 ml and wash with 15 changes of water in a 100 kDa-MWCO ultrafiltration cartridge (UFP-100-E-5A). Filter-sterilize the 40DXPEG1035NTA product (using 0.2 um polysulfone filter, Nalgene, Rochester, N.Y.) and lyophilize. Make 10 mg/ml solution of resulting 40DXPEG1035NTA and determine the hydrodynamic diameter by size exclusion chromatography using TosohG4000WXL column (0.79×30 cm) and elution at a flow rate of 0.6 ml/min with phosphate buffered saline (PBS; 11.9 mM phosphate, 137 mM NaCl, 2.7 mM KPO4, pH 7.4) containing 15% Acetonitrile. The retention time should be consistent with diameter of approx 17-25 nm.

Examples of Compositions with Polymeric Backbones Derived from Polyaminoacids

Example 14: Synthesis of 20PLPEG1030DTPASO or 20PLPEG1030DTPASF or 20PLPEG1030DTPAPO This structure comprises of 20 kDa polylysine in which 30% of the epsilon amino groups are covalently linked to 10 kDa MPEG and the remaining amino groups are covalently linked to diethylenetriaminepentaacetic acid (DTPA) modified to contain sulfate (or sulfonate or phosphate) groups covalently linked to the carbonyl groups of DTPA. Essentially, each DTPA acts as spacer to allow a cluster of four sulfate (or sulfonate or phosphate) groups to be attached to the polylysine backbone (other backbones can also be used). This was synthesized as follows: A) 1 gm of 20 kDa polylysine (20PL; product #Q4926 from SAFC lot #018K7775; DP=126) was dissolved in 6.5 ml of 1 M HEPES. The amino group was measured by TNBS and was found to be 2.4 mmol NH2/g. This is the 20PL solution. B) In a separate container, 5 g of MPEGC (Methoxypolyethylene glycolcarboxymethyl; MW=10 kDa; 0.5 mmol; Laysan Bio; lot #108-108) was dissolved in 12.5 ml of 80% ethanol with 10 mM MES buffer, pH=4.7, with 120 mg of NHS (MW=115.14; 1.0 mmol). Once dissolved 320 g EDC (MW=191.71; 1.7 mmol) was added while stirring. Activation was allowed to proceed for 20 minutes. The activated MPEGC was added to the 20PL solution. The pH was adjusted to pH 7.8 slowly with 10N NaOH one drop at a time, and allowed to react overnight. Aliquot was taken for amino group measurement using TNBS and found be 1.60 mmol indicating 33.5% PEG saturation. This is the 20PLPEG1030DA solution. C) Size Exclusion chromatography using TosohG4000WXL column (0.79×30 cm) eluted with phosphate buffered saline (PBS; 11.9 mM phosphate, 137 mM NaCl, 2.7 mM KPO4, pH 7.4) containing 15% Acetonitrile at a flow rate of 0.6 ml/min showed a retention time of 11.3 min (approx 23.9 nm in diameter). D) 3.5 g of DTPA (Diethylenetriaminepenta-acetic acid dianhydride; MW=357.32; 9.8 mmol; 6 molar equivalent of amino group) was added to solution in step B (20PLPEG1030DA; 1.6 mmol NH2) and followed by 100 ul TEA (triethylamine). The mixture was titrated slowly to pH 7.8 with 10N NaOH and allowed to react overnight. Amino groups was measured and found to be 0 uM. The reaction mixture was diluted with 50 ml 50% ethanol and washed with 10 changes of water in 100,000 MWCO ultrafiltration cartridge (UFP-100-E-5A). The solution was concentrated to 100 ml in water. E) 12.7 mmol of 2-Aminoethyl hydrogen sulfate (AES; C2H7N-SO4; MW=141.14; 12.7 mmol; Acros; Cas #926-39-6; lot #A004514401) or Sulfanilic acid (SNA, C6H7N-SO3; MW=173.19; 12.7 mmol; Acros; Cas #121-57-3; lot #A018717701) or O-Phosphorylethanolamine (C2H8N-$PO_4$; MW=141.06; 12.7 mmol; Acros; Cas #1071-23-4; lot #0001437763) was dissolved in 25 ml of 1 M HEPES. The mixture was titrated slowly to pH 7.8 with 10N NaOH. The amino group was measured by TNBS and was found to be about 16 mmol NH2. F) Solution in step D (20PLPEG1030DTPA; 4×1.6=6.4 mmol carboxyl) was made up to 10 mM MES pH=4.7 (1100 uL of 1M MES added to 110 ml) and 880 mg of NHS (MW=115.14; 7.7 mmol) was added. Once dissolved, activation was started by adding 4 g EDC (MW=191.71; 21 mmol) and allowed to proceed for 20 minutes. The activated carrier was added to the solution E allowed to react overnight. Aliquot was taken for amino group analysis by TNBS and was found to be about 9 mmol and indicating DTPA fully saturated with sulfate (or sulfonate or phosphate). This is the 20PLPEG1030DTPASO or 20PLPEG1030DTPASF or 20PLPEG1030DTPAPO solution. F) The solution was washed with 10 changes of water using 100 kDa MWCO ultrafiltration cartridge (UFP-100-E-5A from GE), and further concentrated to 100 ml. G) Sample was filter-sterilized (0.2 μm polysulfone filter, Nalgene, Rochester, N.Y.) and lyophilized yielding ~4 grams.

Example 15: Synthesis of 40PLPEG535DTPA and 40PLPEG535DTPAIDA

This will be used as starting materials for the synthesis of some of the anionic core compositions of the present invention. To make this, 1.0 g of 40PL (P3995 Sigma lot #085K5102) was dissolved in 50 ml of 200 mM HEPES. Amino group was measured by TNBS assay and was found to be 2.86 mmol $NH_2$/g. Three grams of MPEGC (Methoxy-PolyEthyleneGlycol-CarboxyMethyl; 1 mmol; MW=5 kDa; 9.0 mmol; Laysan Bio; lot #108-41; clear in soln) in 17.5 ml of 10 mM MES pH=4.7 was activated by adding 150 mg of NHSS (MW=217.14; 0.7 mmol), followed by 300 mg EDC (MW=191.71; 1.57 mmol). Activation is allowed to proceed for 20 minutes. Total volume of MPEGC solution at this stage was 18 ml. The activated MPEGC was added to 40PL solution and allowed to react. After 45 minutes, additional 3 g of MPEGC was activated and added as above and allowed to react for 2 hrs. Amino group was measured by TNBS and found to be 103 uM giving 28% saturation. Size Exclusion chromatography using TosohG4000WXL column (0 79×30 cm) eluted with phosphate buffered saline (PBS; 11.9 mM phosphate, 137 mM NaCl, 2.7 mM KPO4, pH 7.4) containing 15% Acetonitrile at a flow rate of 0.6 ml/min showed a retention time of 11.72 min on UV or 12.20 min on RI (18.4 nm). Another 1.5 g were activated and added to reach 35% amino group saturation based on the remaining amino group as measured (91 μM in 94 ml or 1.82 mmol total) by TNBS. After addition of 1.5 g of MPEG retention time on UV becomes of 11.60 min or 12.10 min on RI or 19 nm. Four grams of DTPA-dianhydride were added and pH was adjusted continuously to maintain pH between 7 to 8. After 4 hours, the total amino group was measured by TNBS and was found to be 0.0 μM. The reaction mixture containing 40PLPEG535DTPA was washed with 20 volumes of water using ultrafiltration cartridge with molecular weight cut off (MWCO) of 100 kDa (UFP-100-E-5A; GE Healthcare) and lyophilized, giving 4.7 g (40PLPEG535DTPA). Half (2.35 g) was saturated with iminodiacetic acid (IDA) as follows: IDA (3 gr) was made up to 10 ml of 1M HEPES, the pH adjusted to 7.5, and made up to 50 ml in 1M HEPES. Half of 40PLPEG535DTPA was divided into 3 equal portions (1.3 mmol carboxyl each based on stoichiometry) and each (25 ml) made to pH 4.7 with 200 ul 1M MES, pH 4.7, the pH did not go down to 4.7 and therefore 20 μl of 6N HCl was added. This was activated by addition of 2 mmol NHSS (434 mg) and 4.5 mmol EDC (864 mg). After 20 minutes, the activated 40PLPEG535DTPA was added to IDA above and repeated 2 more times and stirred for 2 hrs. The product (40PLPEG535DTPAIDA) was washed with 20 volumes of water, filter-sterilized (0.2 μm polysulfone filter, Nalgene, Rochester, N.Y.) and lyophilized giving 2.0 g (40PLPEG535DTPAIDA).

Example 16: Synthesis of 40PLPEG535DTPASO or 40PLPEG535DTPASF or 40PLPEG535DTPAPO or 40PLPEG535DTPAIDASO or 40PLPEG535DTPAIDASF or 40PLPEG535DTPAIDAPO This structure comprises of 40 kDa polylysine in which 35% of the epsilon amino groups are covalently linked to 5 kDa MPEG and the remaining amino groups are covalently linked to diethylenetriaminepentaacetic acid (DTPA) modified to contain sulfate (or sulfonate, or phosphate) groups covalently linked to the carbonyl groups of DTPA. Essentially, each DTPA acts as spacer to allow a cluster of four sulfate groups to be attached to the polylysine backbone (other backbones can also be used). The 40PLPEG535DTPA or 40PLPEG535DTPAIDA can be converted to sulfated (or sulfonated or phosphorylated) carrier containing up to several sulfate (or sulfonate or phosphate) groups in each cluster. To do this, take 2 grams 40PLPEG535DTPA or 1 gram of 40PLPEG535DTPAIDA and dissolve it in 50 ml of 10 mM MES buffer (pH 4.7). Activate the carrier by adding 0.37 g of NHSS (MW=217.14; 1.7 mmol), followed by 0.75 g EDC (MW=191.71; 3.9 mmol), and allow to activate for 20 minutes. In a separate container dissolve 0.5 g 2-aminoethylhydrogensulfate (AES; MW=141; 3.5 mmol) or 0.6 g sulfanilic acid (SNA; MW=173; 3.5 mmol) or 0.5 g O-phosphorylethanolamine (OPE; MW=141; 3.5 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 3.5 mmol. Add activated carrier to AES (or SNA or OPE) solution. After 2 hours add another 0.75 g EDC and stir the solution overnight. Measure the amino groups by TNBS to determine the amount of decrease in amino groups which is equivalent to the amount of sulfate (or sulfonate, or phosphate) groups incorporated. Wash the sulfated (or sulfonated, or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize. This product (40PLPEG535DTPASO or 40PLPEG535DTPASF or 40PLPEG535DTPAPO or 40PLPEG535DTPAIDASO or 40PLPEG535DTPAIDASF or 40PLPEG535DTPAIDAPO) will have a cluster of up to 4-8 sulfate, sulfonate or phosphate groups pendant to the backbone.

Example 17: Synthesis of 40PLPEG537NDA from NTA Attached to amino group of Polylysine (lot #20080124b)

The 40PLPEG537NDA will be used as the starting material for the synthesis of some of the anionic core compositions of the present invention. This structure comprises of 40 kDa polylysine in which 37% of the amino groups are covalently linked to 5 kDa MPEG and the remaining amino groups are covalently linked to one of the carbonyl group of nitrilotriacetic acid (NTA). To make this, 1.0 gram of 40PL (Sigma P3995 lotnumber127K5101; 1 g contains 2.62 mmol $NH_2$) was dissolved in 50 ml of 400 mM HEPES. Five g of MPEGC (1 mmol; MW=5 kDa; Sigma/Fisher/Fluka; Cat #70718; lot #64748/1) in 20 ml of 10 mM MES pH=4.7 was activated by adding 250 mg of NHS (MW=115.09; 2 mmol), followed by 500 mg EDC (MW=191.71; 1.8 mmol). Activation is allowed to proceed for 20 minutes (total volume is 20 ml). The activated MPEGC was added to 40PL solution (pH 7.45 before addition). The mixture was allowed to react for 4 hrs. The amino group measurement before (2.62 mmol) and after (1.64 mmol) the addition of MPEG indicated that the PEG saturation of amino group was 37%. Size Exclusion chromatography using TosohG4000WXL column (0.79×30 cm) eluted with phosphate buffered saline (PBS; 11.9 mM phosphate, 137 mM NaCl, 2.7 mM $KPO_4$, pH 7.4) containing 15% Acetonitrile at a flow rate of 0.6 ml/min showed a retention time of 12.5 min (or approximately 16 nm in diameter). This is the 40PLPEG537DA solution. In a separate container, NTA (MW=191; 1 g or 5.2 mmol) was neutralized in water with 1 ml of 10N NaOH and buffered with 20 mM MES at pH 4.7 (total volume is 10 ml). This was activated with 1 g (5.2 mmol) EDC in the presence of 345 mg NHS (MW=115.09; 3 mmol). After 20 minutes of activation this was added to 40PLPEG537DA and the pH was adjusted to 7.8 using 10N NaOH. After 2 hours, additional 2 g EDC was added and allowed to react overnight. The total amino group was measured and found to be 0.03 mmol which is compared to 1.63 mmol original amino groups before the reaction. Sample was washed with 20 volume changes of water using a 100 kDa MWCO ultrafiltration cartridge (UFP-100-E-5A; GE-Amersham), filter-sterilized (0.2 um polysulfone filter; Nalgene, Rochester, N.Y.) and lyophilized giving 4.1 g of 40PLPEG537NDA.

Example 18: Synthesis of 40PLPEG537NDASO or 40PLPEG537NDASF or 40PLPEG537NDAPO

This structure comprises of 40 kDa polylysine in which 37% of the amino groups are covalently linked to 5 kDa MPEG and the remaining amino groups are covalently linked to one of the carbonyl group of NTA and the remaining carbonyl groups of NTA is modified to contain sulfate (or sulfonate, or phosphate) groups. Essentially, each NTA acts as spacer to allow a cluster of two sulfate (sulfonate, or phosphate) groups to be attached to the polylysine backbone (other backbones can also be used). The 40PLPEG537NDA can be converted to sulfated (sulfonated, or phosphorylated) carrier containing up to two sulfate (or sulfonate, or phosphate) groups in each cluster. To do this, take 2 grams of the carrier, (40PLPEG537NDA) and dissolve it in 50 ml of 10 mM MES buffer (pH 4.7). Activate the carrier by adding 0.19 g of NHSS (MW=217.14; 0.87 mmol), followed by 0.37 g EDC (MW=191.71; 1.9 mmol), and allow to activate for 20 minutes. In a separate container dissolve 0.25 g 2-aminoethylhydrogensulfate (AES; MW=141; 1.8 mmol) or 0.31 g sulfanilic acid (SNA; MW=173; 1.8 mmol) or 0.25 g O-phosphorylethanolamine (OPE; MW=141; 1.8 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 1.8 mmol, depending on the purity of AES (or SNA or OPE). Add the AES (SNA or OPE) solution to the carrier after 20 minutes of carrier activation. After 2 hours add another 0.37 g EDC and stir the solution overnight. Measure the amino groups by TNBS to determine the amount of decrease in amino groups which is equivalent to the amount of sulfate (or sulfonate, or phosphate) groups incorporated. Wash the sulfated (or sulfonated, or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize. This product (40PLPEG537NDASO or 40PLPEG537NDASF or 40PLPEG537NDAPO) will have a cluster of up to 2 sulfate (or sulfonate, or phosphate) groups pendant to the backbone.

Example 19: Synthesis of 20PLPEG550DTPANTA

The 20PLPEG550DTPANTA will be used as the starting material for the synthesis of some of the anionic core compositions of the present invention. This structure comprises of 20 kDa polylysine in which 50% of the amino groups are covalently linked to 5 kDa MPEG and the remaining amino groups are covalently linked to one of the carbonyl group of DTPA. The remaining carbonyl groups of DTPA are linked to the epsilon aminogroup of biscarboxymethyl lysine. To make this: a) 1 mL or 0.4 g equivalent of 20PL (Q4926 SAFC lot #018K7775; DP=126; 0.4 g was found to contain 0.895 mmol $NH_2$ by TNBS) was dissolved in 5 ml of 1 M HEPES. This is the 20PL solution. b) In a separate container, 2.5 g MPEG was activated in 20 mM MES pH=4.7 (35 ml) by adding 125 mg of NHS (MW=115.14; 1.09 mmol) and 500 mg EDC (MW=191.71; 2.60 mmol) while stirring. Activation was allowed to proceed for 20 minutes and the activated MPEGC was added directly to 20PL solution in step a. The pH of the reaction mixture was adjusted to pH 7.1 slowly with 10N NaOH one drop at a time, and allowed to react overnight. Amino group analysis by TNBS showed 0.464 mmol amino groups remains, indicating 50% PEG saturation. This is the 20PLPEG550DA solution. c) Size Exclusion chromatography using TosohG4000WXL column (0.79×30 cm) eluted with phosphate buffered saline (PBS; 11.9 mM phosphate, 137 mM NaCl, 2.7 mM $KPO_4$, pH 7.4) containing 15% Acetonitrile at a flow rate of 0.6 ml/min showed a retention time of 12.8 min in refractive index detector or approximately 14.4 nm molecular diameter. d) Diethylenetriaminepentaacetic acid dianhydride (1 gram; FW=357.3; 2.80 mmol) was added and slowly titrated with 10 N NaOH to pH 7.1 and stirred for 2 hours. After 2 hours, amino group measurement by TNBS indicated 0% amino group remains. e) The pH of the solution was adjusted to 7.5 using 10N NaOH to facilitate washing as crystals of un-reacted DTPA remains. The solution was concentrated to 100 ml and washed with 15 changes of water using a 100,000 MWCO ultrafiltration cartridge (UFP-100-E-5A; GE-Amersham) and lyophilized. Size Exclusion chromatography using TosohG4000WXL column (0.79×30 cm) eluted with phosphate buffered saline (PBS; 11.9 mM phosphate, 137 mM NaCl, 2.7 mM $KPO_4$, pH 7.4) containing 15% Acetonitrile at a flow rate of 0.6 ml/min showed a retention time of 12.7 min in a refractive index detector or approximately 15.04 nm molecular. f) 2 gram of NTA-amine (Nalpha,Nalpha, -Bis (carboxymethyl)-L-Lysine; MW=262.26+50% impurity, up to 2 mol water and 10% inorganic) or ~4 mmol amino groups was dissolved in 10 ml of 1M HEPES. Amino group analysis by TNBS indicated that the NTA-amine solution contains 3.4 mmol amino groups. g) 20PLPEG550DTPA (0.70 mmol carboxyl) was dissolved in 10 ml of 20 mM MES, 140 mg NHS (MW=115.09; 1.2 mmol) was added, followed by 560 mg EDC (MW=191.71; 2.9 mmol). The pH went up slowly but was maintained below 5.5 by HCl. This solution was added to NTA solution and the pH was adjusted to pH 7.1 with 10N NaOH. After 2 hours, amino group analysis showed a total of 3.2 mmol amino groups remains, indicating that 0.2 mmol of NTA-amine was incorporated to 0.8 mg carrier. h) The solution was concentrated to 100 ml and washed with 15 changes of water using a 100,000 MWCO ultrafiltration cartridge (UFP-100-E-5A; GE-Amersham), filter-sterilize (0.2 um polysulfone filter, Nalgene, Rochester, N.Y.) and lyophilized yielding 0.5 g (20PLPEG550DTPANTA). Analysis by Size Exclusion chromatography using TosohG4000WXL column (0.79×30 cm) eluted with phosphate buffered saline (PBS; 11.9 mM phosphate, 137 mM NaCl, 2.7 mM $KPO_4$, pH 7.4) containing 15% Acetonitrile at a flow rate of 0.6 ml/min showed a retention time of 12.7 min in a refractive index detector showing approximately 15.04 nm molecular diameter.

Example 20: Synthesis of 20PLPEG550DTPANTASO or 20PLPEG550DTPANTASF or 20PLPEG550DTPANTAPO This structure comprises of 20 kDa polylysine in which 50% of the amino groups are covalently linked to 5 kDa MPEG and the remaining amino groups are covalently linked to one of the carbonyl group of DTPA and the remaining carbonyl groups of DTPA is linked to epsilon amino group of carboxymethyl lysine. The carboxymethyllysine is further modified to contain three sulfate (or sulfonate, or phosphate) groups, each attached to the carboxyl groups of carboxymethlylysine. Essentially, each DTPA($NTA)_3$ acts as spacer to allow a cluster of twelve sulfate (or sulfonate, or phosphate) groups to be attached to the polylysine backbone (other backbones can also be used). The product (20PLPEG550DTPANTA) can be converted to sulfated (or sulfonated, or phosphorylated) carrier containing up to twelve sulfate (or sulfonate, or phosphate) groups in each cluster. To do this, take 2 grams of the carrier, (20PLPEG550DTPANTA) and dissolve it in 50 ml of 10 mM MES buffer (pH 4.7). Activate the carrier by adding 1.1 g of NHSS (MW=217.14; 5.1 mmol), followed by 2.2 g EDC (MW=191.71; 11.5 mmol), and allow to activate for 20 minutes. In a separate container dissolve 1.5 g 2-aminoethylhydrogensulfate (AES; MW=141; 10.6 mmol), or 1.8 g sulfanilic acid (SNA; MW=173; 10.6 mmol), or 1.5 g O-phosphorylethanolamine (OPE; MW=141; 10.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 10.6 mmol, depending on the purity of AES (SNA or OPE). After 20 minutes of carrier activation, add the carrier to AES (or SNA or OPE) solution. After 2 hours add another 2.2 g EDC and stir the solution overnight. Measure the amino groups by TNBS to determine the amount of decrease in amino groups which is equivalent to the amount of sulfate (or sulfonate, or phosphate) groups incorporated. Wash the sulfated (or sulfonated, or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize. This product (20PLPEG550DTPANTASO or 20PLPEG550DTPANTASF or 20PLPEG550DTPANTAPO) will have clusters of up to twelve sulfate (or sulfonate, or phosphate) groups each pendant to the backbone.

Example 21: Synthesis of 35PEPEG1035NTA

The 35PEPEG1035NTA will be used as the starting material for the synthesis of some of the anionic core compositions of the present invention. This composition has polyglutamic acid (Sigma Chem. Co. St Luis Mo. Cat #P4033, MW=15-50 kDa; or Fisher Chem. Co. Pittsburgh, Pa., Cat #ICN15191891, MW=15-50 kDa) as the polymeric backbone with 35% of the carboxyl group occupied with 10 kDa MPEGAM (MW=10 kDa MPEG with amino group at the terminal; Sunbio, Orinda, Calif.; Cat #P1AM-10) and the remaining carboxyl groups occupied with nitrilotriacetic acid. To synthesize 35PEPEG1035NTA, measure the starting carboxyl group (1 equivalent) of 1.0 g poly-glutamic acid according to the protocol by Kobayahi and Chiba (Analytical biochemistry 1994, vol 219, p 189-194). Take 1.0 g of polyglutamic acid (Sigma Chem. Co. St Luis Mo. Cat #P4033; MW=15-50 kDa, with 1 equivalent carboxyl group/gram), dissolve in 25 ml of 10 mM MES (2-(N-morpholino)ethanesulfonic acid, Pierce, Rockford, Ill.) buffer pH 4.7, add 1 equivalent of NHS (MW=115.14) and 1 equivalent EDC (MW=191.71) and stir to activate PE for 20 minutes. In a separate container, dissolve 0.35 equivalents of MPEGAM (MW=10 kDa MPEG with amino group at the terminal; Sunbio, Orinda, Calif.; Cat #P1AM-10) in 20 ml of 0.2M HEPES, pH 7.8 to obtain MPEGAM solution. After 20 minute of PE activation, add PE to MPEGAM solution and allow the reaction to proceed for 2 hours. Measure the remaining amino group of the MPEGAM by TNBS and should be none indicating that all 0.35 equivalent amino group is used up and conjugated to the polyglutamic acid. If there are remaining amino group, adjust pH to 5 with 6N HCl and add 1 equivalent EDC (MW=191.71), after 20 minutes adjust back the pH to 7.8 and allow to react overnight. Take an aliquot of the resulting 35PEPEG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with hydrodynamic diameter of approx 16-24 nm. Adjust pH down to 5 with 6N HCl and add 1.5 equivalents EDC (MW=191.71) and activate for 20 minutes. After 20 minutes add this activated 40PEPEG1035 solution to 10 equivalents of Nalpha,Nalpha-biscarboxymethyl-lysine (MW=262 Da) in 25 ml of 0.2M HEPES buffer at pH 7.8 and allow to react overnight. Concentrate the reaction mixture to 100 ml and wash with 15 changes of water in a 100 kDa-MWCO ultrafiltration cartridge (UFP-100-E-5A). Filter-sterilize the sample using (0.2 um polysulfone filter, Nalgene, Rochester, N.Y.) and lyophilize. Make 10 mg/ml solution of resulting 35PEPEG1035NTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should be consistent with hydrodynamic diameter of approx 19-28 nm.

Example 22: Synthesis of 35PGPEG1035NTASO or 35PGPEG1035NTASF or 35PGPEG1035NTAPO This structure comprises of 35 kDa polyglutamate in which 35% of the carboxyl groups are covalently linked to 10 kDa MPEG and the remaining carboxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the polyglutamate backbone (other backbones can also be used). The 35PGPEG1035NTA can be converted to sulfated (or sulfonated, or phosphorylated) carrier containing clusters of sulfate (or sulfonate, or phosphate) groups with up to three sulfate (or sulfonate, or phosphate) groups in each cluster. To do this, take 2 grams of the carrier, (35PGPEG1035NTA) and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). After 20 minutes of carrier activation, add the activated carrier to AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate, or phosphate) groups incorporated. Wash the sulfated (or sulfonated, or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize. This product (35PGPEG1035NTASO or 35PGPEG1035NTASF or 35PGPEG1035NTAPO) will have clusters of up to three sulfate (or sulfonate, or phosphate) groups each pendant to the backbone Example 23: Synthesis of 10PDPEG1035NTA The 10PDPEG1035NTA will be used as the starting material for the synthesis of some of the anionic core compositions of the present invention. This composition has polyaspartic acid (Sigma Chem. Co. St Luis Mo. Cat #P5387, MW=5-15 kDa) as the polymeric backbone with 35% of the carboxyl groups occupied with 10 kDa MPEGAM (MW=10 kDa MPEG with amino group at the terminal; Sunbio, Orinda, Calif.; Cat #P1AM-10) and the remaining carboxyl group occupied with nitrilotriacetic acid. Measure the starting carboxyl group 1 equivalent of 1.0 g poly-glutamic acid according to the protocol by Kobayahi and Chiba (Analytical biochemistry 1994, vol 219, p 189-194). To synthesize 10PDPEG1035NTA, take 1.0 g of polyaspartic acid (Sigma Chem. Co. St Luis Mo. Cat #P4033; MW=15-50 kDa, with 1 equivalent carboxyl group/gram) and dissolve in 25 ml of 20 mM MES (2-(N-morpholino)ethanesulfonic acid, Pierce, Rockford, Ill.) buffer pH 4.7 to make the PD solution. Dissolve 0.25 equivalents of MPEGAM (MW=10 kDa MPEG with amino group at the terminal; Sunbio, Orinda, Calif.; Cat #P1AM-10) in 20 ml of 80% ethanol and add to the PD solution to make PDPEG solution. To the PDPEG solution, add 1 equivalent NHS (MW=115.14) and 1 equivalent EDC (MW=191.71) while stirring. Maintain the pH at pH 4.7-5.0 with 6N HCl for 20 minutes using HCl. After 20 minutes of activation, adjust the pH to 7.8 by adding 10 ml of 1M HEPES, pH 7.4. Adjust pH to 7.8 with 10N NaOH one drop at a time. Allow the reaction to proceed for 2 hours and measure the remaining amino group of the MPEGAM by TNBS and should be none indicating that all 0.35 equivalents amino group is used up and conjugated to the polyaspartic acid. If there are remaining amino group, add 1 equivalent EDC (MW=191.71) and allow to react overnight. Take an aliquot of the resulting 10PDPEG1035 solution and determine the hydrodynamic diameter by size exclusion chromatography using TosohG4000WXL column (0.79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with hydrodynamic diameter of approx 12-18 nm. Adjust pH down to 5 with 6N HCl and add 1.5 equivalents EDC (MW=191.71) and activate for 20 minutes. After 20 minutes add this activated 10PDPEG1035 solution to 10 equivalents of Nalpha,Nalpha-biscarboxymethyl-lysine (MW=262 Da) in to 25 ml of 1M HEPES buffer at pH 7.8 and allow to react overnight. Concentrate the reaction mixture to 100 ml and wash with 15 changes of water in a 100 kDa-MWCO ultrafiltration cartridge (UFP-100-E-5A). Filter-sterilize the sample using (0.2 μm polysulfone filter, Nalgene, Rochester, N.Y.) and lyophilize. Make 10 mg/ml solution of resulting 10PDPEG1035NTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should be with hydrodynamic diameter of approx 14-20 nm.

Example 24: Synthesis of 10PDPEG1035NTASO or 10PDPEG1035NTASF or 10PDPEG1035NTAPO This structure comprises of 10 kDa polyaspartate in which 35% of the carboxyl groups are covalently linked to 10 kDa MPEG and the remaining carboxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the polyaspartate backbone (other backbones can also be used). The 10PDPEG1035NTA can be converted to sulfated (or sulfonated, or phosphorylated) carrier containing clusters of sulfate groups with up to three sulfate groups in each cluster. To do this, take 2 grams of the 10PDPEG1035NTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate, or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 um polysulfone filter, Nalgene, Rochester, N.Y.) and lyophilize. This product (10PDPEG1035NTASO or 10PDPEG1035NTASO or 10PDPEG1035NTA SF or 10PDPEG1035NTAPO) will have clusters of up to three sulfate (sulfonate, or phosphate) groups per cluster that is pendant to the backbone.

Example 25: Synthesis of 10PSPEG1035NTA

The 10PSPEG1035NTA will be used as the starting material for the synthesis of some of the anionic core compositions of the present invention. This composition has polyserine (Sigma Chem. Co. St Luis Mo. Cat #P5857, MW=5-15 kDa) as the polymeric backbone with 35% of the hydroxyl groups occupied with 10 kDa MPEGAM (MW=10 kDa MPEG with amino group at the terminal; Sunbio, Orinda, Calif.; Cat #P1AM-10) and the remaining hydroxyl group occupied with nitrilotriacetic acid. To prepare this composition all hydroxyl groups will be converted to carboxyl group using succinic anhydride. Briefly, dissolve 1 g of polyserine in 25 ml of dioxane and add 5.2 gram of succinicanhydride (five-fold molar excess over total theoretical hydroxyl group) and 900 mg of N,N'-dimethylaminopyridine as catalyst and incubate the mixture at 60° C. for 3 hours. Remove dioxane by rotary evaporation at 40° C., dissolve the solid in water, neutralized with NaOH and wash 15 changes of water in a 3 kDa-MWCO ultrafiltration cartridge (UFP-3-E-5A). Filter-sterilize the resulting product (PS) using (0.2 um polysulfone filter, Nalgene, Rochester, N.Y.) and lyophilize. Measure the starting carboxyl group (1 equivalent) in 1.0 g PS according to the protocol by Kobayahi and Chiba (Analytical biochemistry 1994, vol 219, p 189-194). To synthesize 10PSPEG1035NTA, take 1.0 g of PS (with 1 equivalent carboxyl group), dissolve in 25 ml of 10 mM MES (2-(N-morpholino)ethanesulfonic acid, Pierce, Rockford, Ill.) buffer pH 4.7 (PS solution), add 1 equivalent of NHS (MW=115.14) and 1 equivalent EDC (MW=191.71; 4 mmol) and stir for 20 minutes to activate. In a separate container, dissolve 0.35 equivalents of MPEGAM (MW=10 kDa MPEG with amino group at the terminal; Sunbio, Orinda, Calif.; Cat #P1AM-10) in 20 ml of 0.2M HEPES pH 7.8 to make MPEGAM solution. After 20 minutes of PS activation, add PS solution to MPEGAM solution and allow the reaction to proceed for 2 hours. Measure the remaining amino group of the MPEGAM by TNBS and should be none indicating that all 0.35 equivalents amino group of MPEGAM is used up and conjugated to the PS. If there are remaining amino group, adjust pH to 5 with 6N HCl and add 1 equivalent EDC (MW=191.71), after 20 minutes adjust back the pH to 7.8 and allow to react overnight. Take an aliquot of the resulting 10PSPEG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be with hydrodynamic diameter of approx 13-18 nm. Adjust pH down to 5 with 6N HCl and add 1.5 equivalents EDC (MW=191.71) and activate for 20 minutes. After 20 minutes add this activated 10PSPEG1035 solution to 10 equivalents of Nalpha, Nalpha-biscarboxymethyl-lysine (MW=262 Da) in to 25 ml of 0.2M HEPES buffer at pH 7.8 and allow to react overnight. Concentrate the reaction mixture to 100 ml and wash with 15 changes of water in a 100 kDa-MWCO ultrafiltration cartridge (UFP-100-E-5A). Filter-sterilize the sample using (0.2 um polysulfone filter, Nalgene, Rochester, N.Y.) and lyophilize. Make 10 mg/ml solution of resulting 10PSPEG1035NTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should be with hydrodynamic diameter of approx 14-19 nm.

Example 26: Synthesis of 10PSPEG1035NTASO or 10PSPEG1035NTASF or 10PSPEG1035NTAPO This structure comprises of 10 kDa polyserine in which 35% of the hydroxylxyl groups are covalently linked to 10 kDa MPEG and the remaining hydroxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the polyaspartate backbone (other backbones can also be used). The 10PSPEG1035NTA (see above) can be converted to sulfated (or sulfonated, or phosphated) carrier containing clusters of sulfate (or sulfonate, or phosphate) groups with up to three sulfate (or sulfonate, or phosphate) groups in each cluster. To do this, take 2 grams of the 10PSPEG1035NTA (above) and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 um polysulfone filter, Nalgene, Rochester, N.Y.) and lyophilize. This product (10PSPEG1035NTASO or 10PSPEG1035NTASF or 10PSPEG1035NTAPO) will have clusters of up to three sulfate (or sulfonate or phosphate) groups per cluster pendant to the backbone.

Example 27: Synthesis of 10PTPEG1035NTA

The 10PTPEG1035NTA will be used as the starting material for the synthesis of some of the anionic core compositions of the present invention. This composition has polythreonine (Sigma Chem. Co. St Luis Mo. Cat #P8077, MW=5-15 kDa) as the polymeric backbone with 35% of the hydroxyl groups occupied with 10 kDa MPEGAM (MW=10 kDa MPEG with amino group at the terminal; Sunbio, Orinda, Calif.; Cat #P1AM-10) and the remaining hydroxyl group occupied with nitrilotriacetic acid. To prepare this composition all hydroxyl groups will be converted to carboxyl group using succinic anhydride. Briefly, dissolve 1 g of polythreonine in 25 ml of dioxane and add 4.5 gram of succinic-anhydride (five-fold molar excess over theoretical hydroxyl group in 1 gram of polythreonine) and 900 mg of N,N'-dimethylaminopyridine as catalyst and incubate the mixture at 60° C. for 3 hours. Remove dioxane by rotary evaporation at 40° C., dissolve the solid in water, neutralized with NaOH and wash 15 changes of water in a 3 kDa-MWCO ultrafiltration cartridge (UFP-3-E-5A). Filter-sterilize the resulting product (PT) using (0.2 um polysulfone filter, Nalgene, Rochester, N.Y.) and lyophilize to obtain PT. Measure the starting carboxyl group (1 equivalent) in 1.0 g PT according to the protocol by Kobayahi and Chiba (Analytical biochemistry 1994, vol 219, p 189-194). To synthesize 10PTPEG1035NTA, take 1.0 g of PT (with 1 equivalent carboxyl group), dissolve in 25 ml of 10 mM MES (2-(N-morpholino)ethanesulfonic acid, Pierce, Rockford, Ill.) buffer pH 4.7 (PT solution), add 1 equivalent of NHS (MW=115.14), 1 equivalent EDC (MW=191.71), and allow to activate for 20 minutes. In a separate container, dissolve 0.35× mmol of MPEGAM (MW=10 kDa MPEG with amino group at the terminal; Sunbio, Orinda, Calif.; Cat #P1AM-10) in 20 ml of 0.2M HEPES, pH 7.8 to make MPEGAM solution. After 20 minutes of PT activation, add PT solution to MPEGAM solution and allow the reaction to proceed for 2 hours. Measure the remaining amino group of the MPEGAM by TNBS and should be none indicating that all 0.35 equivalents amino group is used up and conjugated to the PT. If there are remaining amino group, adjust pH to 5 with 6N HCl and add 1 equivalent EDC (MW=191.71), after 20 minutes adjust back the pH to 7.8 and allow to react overnight. Take an aliquot of the resulting 10PTPEG1035 solution and determine the hydrodynamic diameter by size exclusion chromatography using TosohG4000WXL column (0.79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with hydrodynamic diameter of approx 12-18 nm. Adjust pH down to 5 with 6N HCl and add 1.5 equivalents EDC (MW=191.71) and activate for 20 minutes. After 20 minutes add this activated 10PTPEG1035 solution to 10 equivalents of Nalpha,Nalpha-biscarboxymethyl-lysine (MW=262 Da) in to 25 ml of 0.2M HEPES buffer at pH 7.8 and allow to react overnight. Concentrate the reaction mixture to 100 ml and wash with 15 changes of water in a 100 kDa-MWCO ultrafiltration cartridge (UFP-100-E-5A). Filter-sterilize the 10PTPEG1035NTA product (using 0.2 um polysulfone filter, Nalgene, Rochester, N.Y.) and lyophilize. Make 10 mg/ml solution of resulting 10PTPEG1035NTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should be consistent with hydrodynamic diameter of approx 14-20 nm.

Example 28: Synthesis of 10PTPEG1035NTASO or 10PTPEG1035NTASF or 10PTPEG1035NTAPO This structure comprises of 10 kDa polythreonine in which 35% of the hydroxylxyl groups are covalently linked to 10 kDa MPEG and the remaining hydroxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the polythreonine backbone (other backbones can also be used). The 10PTPEG1035NTA (see above) can be converted to sulfated (or sulfonated, or phosphated) carrier containing clusters of sulfate (or sulfonate, or phosphate) groups with up to three sulfate (or sulfonate, or phosphate) groups in each cluster. To do this, take 2 grams of the 10PTPEG1035NTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 um polysulfone filter, Nalgene, Rochester, N.Y.) and lyophilize. This product (10PTPEG1035NTASO or 10PTPEG1035NTASF or 10PTPEG1035NTAPO) will have clusters of up to three sulfate (or sulfonate, or phosphate) groups per cluster pendant to the backbone.

Example 29: Synthesis of 20PYPEG1035NTA

The 20PYPEG1035NTA will be used as the starting material for the synthesis of other anionic core compositions of the present invention. This composition has polytyrosine (Sigma Chem. Co. St Luis Mo. Cat #P1800, MW=10-40 kDa) as the polymeric backbone with 35% of the hydroxyl groups occupied with 10 kDa MPEGAM (MW=10 kDa MPEG with amino group at the terminal; Sunbio, Orinda, Calif.; Cat #P1AM-10) and the remaining hydroxyl group occupied with nitrilotriacetic acid. To prepare this composition all hydroxyl groups will be converted to carboxyl group using succinic anhydride. Briefly, dissolve 1 g of polytyrosine in 25 ml of dioxane and add 2.9 gram of succinicanhydride (five-fold molar excess over theoretical hydroxyl group in 1 gram of polytyrosine) and 900 mg of N,N'-dimethylaminopyridine as catalyst and incubate the mixture at 60° C. for 3 hours. Remove dioxane by rotary evaporation at 40° C., dissolve the solid in water, neutralized with NaOH and wash 15 changes of water in a 3 kDa-MWCO ultrafiltration cartridge (UFP-3-E-5A). Filter-sterilize the resulting product (PY) using (0.2 um polysulfone filter, Nalgene, Rochester, N.Y.) and lyophilize to obtain PY. Measure the starting carboxyl group (1 equivalent) in 1.0 g PY according to the protocol by Kobayahi and Chiba (Analytical biochemistry 1994, vol 219, p 189-194). To synthesize 20PYPEG1035NTA, take 1.0 g of PY (with 1 equivalent carboxyl group) and dissolve in 25 ml of 10 mM MES (2-(N-morpholino)ethanesulfonic acid, Pierce, Rockford, Ill.) buffer pH 4.7 (PY solution), add 1 equivalent of NHS (MW=115.14) and 1 equivalent EDC (MW=191.71) and stir for 20 minutes to activate. In a separate container, dissolve 0.35 equivalents of MPEGAM (MW=10 kDa MPEG with amino group at the terminal; Sunbio, Orinda, Calif.; Cat #P1AM-10) in 20 ml of 0.2M HEPES buffer at pH 7.8 to make MPEGAM solution. Add activated PY solution to MPEGAM solution and allow the reaction to proceed for 2 hours. Measure the remaining amino group of the MPEGAM by TNBS and should be none indicating that all 0.35 equivalents amino group is used up and conjugated to the PY. If there are remaining amino group, adjust pH to 5 with 6N HCl and add 1 equivalent EDC (MW=191.71), after 20 minutes adjust back the pH to 7.8 and allow to react overnight. Take an aliquot of the resulting 20PYPYG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with hydrodynamic diameter of approx 13-18 nm. Adjust pH down to 5 with 6N HCl and add 1.5 equivalents EDC (MW=191.71) and activate for 20 minutes. After 20 minutes add this to 10 equivalents of Nalpha,Nalpha-biscarboxymethyl-lysine (MW=262 Da) in to 25 ml of 0.2M HEPES buffer at pH 7.8 and allow to react overnight. Concentrate the reaction mixture to 100 ml and wash with 15 changes of water in a 100 kDa-MWCO ultrafiltration cartridge (UFP-100-E-5A). Filter-sterilize the sample using (0.2 um polysulfone filter, Nalgene, Rochester, N.Y.) and lyophilize. Make 10 mg/ml solution of resulting 20PYPEG1035NTA and determine the hydrodynamic diameter by size exclusion chromatography using TosohG4000WXL column (0 79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should be consistent with hydrodynamic diameter of approx 14-20 nm.

Example 30: Synthesis of 20PYPEG1035NTASO or 20PYPEG1035NTASF or 20PYPEG1035NTAPO This structure comprises of 20 kDa polytyrosine in which 35% of the hydroxylxyl groups are covalently linked to 10 kDa MPEG and the remaining hydroxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate groups to be attached to the polytyrosine backbone (other backbones can also be used). The 20PYPEG1035NTA (see above) can be converted to sulfated (or sulfonated, or phosphorylated) carrier containing clusters of sulfate (or sulfonate, or phosphate) groups with up to three sulfate (or sulfonate, or phosphate) groups in each cluster. To do this, take 2 grams of the 20PYPEG1035NTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize. This product (20PYPEG1035NTASO or 20PYPEG1035NTASF or 20PYPEG1035NTAPO) will have clusters of up to three sulfate (or sulfonate, or phosphate) groups per cluster pendant to the backbone.

Example 31: Synthesis of 20PCPEG1035DTPA

The 20PCPEG1035DTPA will be used as the starting material for the synthesis of other anionic core compositions of the present invention. This composition has polycysteine (Sigma Chem. Co. St Luis Mo. Cat #P1800, MW=10-40 kDa) as the polymeric backbone with 35% of the thiol groups occupied with 10 kDa MPEGC (MW=10 kDa; SunBright; ME-100HS; lot #M62503; clean in solution) and the remaining thiol group occupied with diethylenetriamine-pentaacetic acid (DTPA). To prepare this composition all thiol groups will be converted to amino group using Aminoethyl-8 (N-(Iodoethyl) Trifluoroacetamide (Pierce, Rockford, Ill., Cat #23010). Briefly, dissolve 1 g of polycysteine in 25 ml of 20 mM tricine buffer at pH 8.5 and add 4.7 gram of Aminoethyl-8 (N-(Iodoethyl) Trifluoroacetamide (2 fold molar excess over theoretical thiol group in 1 gram of polycysteine) and incubate the mixture at room temperature for 3 hours. Wash 15 changes of water in a 3 kDa-MWCO ultrafiltration cartridge (UFP-3-E-5A). Filter-sterilize the resulting product (PC) using (0.2 um polysulfone filter, Nalgene, Rochester, N.Y.) and lyophilize to obtain PC. Measure the starting aminogroup group (1 equivalent) in 1.0 g PC using TNBS as above. To synthesize 20PCPEG1035DTPA, take 1.0 g of PC (with 1 equivalent aminogroup) and dissolve in 25 ml of 0.2M HEPES buffer at pH 7.8 (Pierce, Rockford, Ill.) to obtain a 20PC solution. In a separate container, dissolve 0.35 equivalents of MPEGC (MW=10 kDa; MethoxyPEG with carboxyl group at the terminal, from Lysan bio; Arab, Ala.) in 60 ml of 10 mM MES pH=4.7, add 0.5 equivalents of NHS (MW=115.14), once dissolved add 1 equivalent EDC (MW=191.71; 10.43 mmol) while stirring and allow the activation to proceed for 20 minutes. Add activated MPEGC directly to 20PC solution, allow for the reaction to accrue for 2 hours and measure amino groups by TNBS to insure 35% saturation of amino groups, else add more of the appropriate amount of activated MPEGC. This is the 20PCPEG1035 solution. Perform size exclusion chromatography using TosohG4000WXL column (0 79×30 cm) with phosphate buffered saline (PBS; 11.9 mM phosphate, 137 mM NaCl, 2.7 mM $KPO_4$, pH 7.4) containing 15% Acetonitrile elution at a flow rate of 0.6 ml/min. The retention time of should be consistent with hydrodynamic diameter of approximately 14-17 nm. Add 5 equivalents DTPA dianhydride (MW=357.32; Sigma Chem. Co., St Louis, Mo. Cat #284025) followed by 200 uL TEA. Titrate the reaction slowly with 10 N NaOH to pH 7.8 and stirred for 4 hours. Using TNBS reaction, confirm that no amino groups remain indicative of a complete reaction, and that the 20PCPEG1035DTPA product is made. Perform size exclusion chromatography using TosohG4000WXL column (0 79×30 cm) with phosphate buffered saline (PBS; 11.9 mM phosphate, 137 mM NaCl, 2.7 mM $KPO_4$, pH 7.4) containing 15% Acetonitrile elution at a flow rate of 0.6 ml/min. The retention time should be consistent with 17-21 nm molecular diameter. Washed the resulting 20PCPEG1035DTPA with 15 volumes of water using a 100,000 MWCO ultrafiltration cartridge (UFP-100-E-5A; GE-Amersham) and lyophilized.

Example 32: Synthesis of 20PCPEG1035DTPASO or 20PCPEG1035DTPASF or 20PCPEG1035DTPAPO This structure comprises of 20 kDa polycysteine in which 35% of the thiol groups are covalently linked to 10 kDa MPEG and the remaining thiol groups are covalently linked to one of the carbonyl group of ethylenediaminetetraacetic acid (DTPA). The DTPA is further modified to contain four sulfate (or sulfonate, or phosphate) groups, each attached to the carbonyl groups of DTPA. Essentially, each DTPA acts as spacer to allow a cluster of four sulfate (or sulfonate, or phosphate) groups to be attached to the polycysteine backbone (other backbones can also be used). The 20PCPEG1035DTPA (see above) can be converted to sulfated (or sulfonated, or phosphorylated) carrier containing clusters of sulfate (or sulfonate, or phosphate) groups with up to four sulfate (or sulfonate, or phosphate) groups in each cluster. To do this, take 2 grams of the 20PCPEG1035DTPA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 um polysulfone filter, Nalgene, Rochester, N.Y.) and lyophilize. This product (20PCPEG1035DTPASO or 20PCPEG1035DTPASF or 20PCPEG1035DTPAPO) will have clusters of up to four sulfate (or sulfonate, or phosphate) groups per cluster that is pendant to the backbone.

Examples of Compositions with Polymeric Backbones Derived from Non-Biological Monomers

Example 33: Synthesis of 15PALPEG1035DTPA

15PALPEG1035DTPA will be used as the starting material for the synthesis of some of the anionic core compositions of the present invention. This composition has polyallylamine hydrochloride (Sigma Chem. Co. St Luis Mo. Cat #283215, MW=15 kDa) as the polymeric backbone with 35% of the amino groups occupied with 10 kDa MPEGC (MW=10 kDa; SunBright; ME-100HS; lot #M62503; clean in soln) and the remaining amino group occupied with ethylenediaminetetraacetic acid (DTPA). To synthesize 15PALPEG1035DTPA, take 1.0 g of polyallylamine hydrochloride (with 1 equivalent aminogroup as measured by TNBS) and dissolve in 25 ml of 0.2M HEPES buffer at pH 7.4 (Pierce, Rockford, Ill.) to obtain a 15PAL solution. In a separate container, dissolve 0.35 equivalents of MPEGC (MW=10 kDa; MethoxyPEG with carboxyl group at the terminal, from Lysan bio; Arab, Ala.) in 60 ml of 20 mM MES pH=4.7, add 0.5 equivalents of NHS (MW=115.14), once dissolved add 1 equivalent EDC (MW=191.71; 10.43 mmol) and stir for 20 minutes. After 20 minutes, add activated MPEGC directly to 15PAL solution, after 2 hours and measure amino groups by TNBS to insure if 35% saturation of amino groups else add more of the appropriate amount of activated MPEGC. This is the 15PALPEG1035 solution. Perform size exclusion chromatography using TosohG4000WXL column (0.79×30 cm) with phosphate buffered saline (PBS; 11.9 mM phosphate, 137 mM NaCl, 2.7 mM $KPO_4$, pH 7.4) containing 15% Acetonitrile elution at a flow rate of 0.6 ml/min. The retention time of should be consistent with approximately 14-17 nm molecular diameter. Add 5 equivalents DTPA dianhydride (MW=357.32; Sigma Chem. Co., St Louis, Mo. Cat #284025) followed by 200 uL TEA. Titrate the reaction slowly with 10 N NaOH to pH 7.8 and stir for 4 hours. Using TNBS reaction, confirm that no amino groups remain indicative of a complete reaction, and that the 15PALPEG1035DTPA product is made. Perform size exclusion chromatography using TosohG4000WXL column (0.79×30 cm) with phosphate buffered saline (PBS; 11.9 mM phosphate, 137 mM NaCl, 2.7 mM $KPO_4$, pH 7.4) containing 15% Acetonitrile elution at a flow rate of 0.6 ml/min. The retention time should be consistent with 17-21 nm molecular diameter. Wash the resulting 15PALPEG1035DTPA with 15 volumes of water using a 100,000 MWCO ultrafiltration cartridge (UFP-100-E-5A; GE-Amersham) and lyophilize.

Example 34: Synthesis of 15PALPEG1035DTPASO or 15PALPEG1035DTPASF or 15PALPEG1035DTPAPO This structure comprises of 15 kDa polyallylamine in which 35% of the amino groups are covalently linked to 10 kDa MPEG and the remaining amino groups are covalently linked to one of the carbonyl group of diethylenetriaminepentaacetic acid (DTPA). The DTPA is further modified to contain four sulfate groups, each attached to the carbonyl groups of DTPA. Essentially, each DTPA acts as spacer to allow a cluster of four sulfate (or sulfonate, or phosphate) groups to be attached to the polyallylamine backbone (other backbones can also be used). The 15PALPEG1035DTPA (see above) can be converted to sulfated (or sulfonated, or phosphorylated) carrier containing clusters of sulfate (or sulfonate, or phosphate) groups with up to four sulfate groups in each cluster. To do this, take 2 grams of the 15PALPEG1035DTPA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 um polysulfone filter, Nalgene, Rochester, N.Y.) and lyophilize. This product (15PALPEG1035DTPASO or 15PALPEG1035DTPASF or 15PALPEG1035DTPAPO)

will have clusters of up to four sulfate (or sulfonate, or phosphate) groups per cluster pendant to the backbone.

Example 35: Synthesis of 20PMAPEG1035NTA

The 20PMAPEG1035NTA will be used as the starting material for the synthesis of some of the anionic core compositions of the present invention. This composition has polymethylmethacrylate (Sigma Chem. Co. St Luis Mo. Cat #81498, MW=20 kDa) as the polymeric backbone with 35% of the methoxy groups replaced with 10 kDa MPEGAM (MW=10 kDa MPEG with amino group at the terminal; Sunbio, Orinda, Calif.; Cat #P1AM-10) and the remaining methoxy groups occupied with nitrilotriacetic acid. To prepare this composition all methoxy groups in polymethylmethacrylate (Sigma Chem. Co. St Luis Mo. Cat #81498, MW=20 kDa) will be removed using Methanolic/KOH to obtain polymethylacrylic acid (PMA). Briefly, dissolve 2 g of polymethylmethacrylate in 25 ml of 10% methanolic KOH for and reflux for 96 h. Neutralize with HCl and remove methanol by rotary evaporation at 40° C., dissolve the solid in water and wash 15 changes of water in a 3 kDa-MWCO ultrafiltration cartridge (UFP-3-E-5A). Filter-sterilize the resulting product (PMA) using (0.2 μm polysulfone filter, Nalgene, Rochester, N.Y.) and lyophilize to obtain PMA. Measure the starting carboxyl group (1 equivalent) in 1.0 g PMA according to the protocol by Kobayahi and Chiba (Analytical biochemistry 1994, vol 219, p 189-194). To synthesize 20PMAPEG1035NTA, take 1.0 g of PMA (with 1 equivalent carboxyl group) and dissolve in 25 ml of 10 mM MES (2-(N-morpholino)ethanesulfonic acid, Pierce, Rockford, Ill.) buffer pH 4.7 (PS solution) and activate by adding 1 equivalent of NHS (MW=115.14) and 1 equivalent EDC (MW=191.71). In separate container, dissolve 0.35 equivalents of MPEGAM (MW=10 kDa MPEG with amino group at the terminal; Sunbio, Orinda, Calif.; Cat #P1AM-10) in 10 ml of 0.2M HEPES and adjust pH top 7.8 with 10N NaOH. After 20 minutes of PMA activation, add PMA to MPEGAM solution. Allow the reaction to proceed for 2 hours and measure the remaining amino group of the MPEGAM by TNBS and should be none indicating that all 0.35 equivalents amino group is used up and conjugated to the PMA. If there are remaining amino group, adjust pH to 5 with 6N HCl and add 1 equivalent EDC (MW=191.71), after 20 minutes adjust back the pH to 7.8 and allow to react overnight. Take an aliquot of the resulting 20PMAPEG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with diameter of approx 13-18 nm. Adjust pH down to 5 with 6N HCl and add 1.5 equivalents EDC (MW=191.71) and activate for 20 minutes. After 20 minutes add this activated 20PMAPEG1035 solution to 10 equivalents of Nalpha,Nalpha-biscarboxymethyl-lysine (MW=262 Da) in to 25 ml of 1M HEPES buffer at pH 7.4 and allow to react overnight. Concentrate the reaction mixture to 100 ml and wash with 15 changes of water in a 100 kDa-MWCO ultrafiltration cartridge (UFP-100-E-5A). Filter-sterilize the 20PMAPEG1035NTA product (using 0.2 μm polysulfone filter, Nalgene, Rochester, N.Y.) and lyophilize. Make 10 mg/ml solution of resulting 20PMAPEG1035NTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should consistent with diameter of approx 16-20 nm.

Example 36: Synthesis of 20PMAPEG1035NTASO or 20PMAPEG1035NTASF or 20PMAPEG1035NTAPO This structure comprises of 20 kDa polymethylacrylate which 35% of the carboxyl groups are covalently linked to 10 kDa MPEG and the remaining carboxyl groups are covalently linked to the epsilon amino group of biscarboxymethyllysine which is a nitrilotriacetic acid (NTA) derivative. The NTA is further modified to contain three sulfate (or sulfonate, or phosphate) groups, each attached to the carbonyl groups of NTA. Essentially, each NTA acts as spacer to allow a cluster of three sulfate (or sulfonate, or phosphate) groups to be attached to the polymethylacrylate backbone (other backbones can also be used). The 20PMAPEG1035NTA (see above) can be converted to sulfated (or sulfonated, or phosphorylated) carrier containing clusters of sulfate (or sulfonate, or phosphate) groups with up to three sulfate (or sulfonate, or phosphate) groups in each cluster. To do this, take 2 grams of the 20PMAPEG1035NTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 μm polysulfone filter, Nalgene, Rochester, N.Y.) and lyophilize. This product (20PMAPEG1035NTASO or 20PMAPEG1035NTASF or 20PMAPEG1035NTAPO) will have clusters of up to three sulfate (or sulfonate, or phosphate) groups per cluster pendant to the backbone.

Example 37: Synthesis of 15PACPEG1035NTA

The 15PACPEG1035NTA will be used as the starting material for the synthesis of some of the anionic core compositions of the present invention. This composition has polyacrylic acid or PAC (Sigma Chem. Co. St Luis Mo. Cat #81123, MW=16 kDa) as the polymeric backbone with 35% of the carboxyl groups linked 10 kDa MPEGAM (MW=10 kDa MPEG with amino group at the terminal; Sunbio, Orinda, Calif.; Cat #P1AM-10) and the remaining carboxyl groups occupied with nitrilotriacetic acid. Measure the starting carboxyl group (1 equivalent) in 1.0 g PAC according to the protocol by Kobayahi and Chiba (Analytical biochemistry 1994, vol 219, p 189-194). To synthesize 15PACPEG1035NTA, take 1.0 g of PAC (with 1 equivalent carboxyl group) and dissolve in 25 ml of 10 mM MES (2-(N-morpholino)ethanesulfonic acid, Pierce, Rockford, Ill.) buffer pH 4.7 (PAC solution). Add 1 equivalent of NHS (MW=115.14) and 1 equivalent EDC (MW=191.71) to PAC solution while stirring to activate PAC. In a separate container, dissolve 0.35 equivalents of MPEGAM (MW=10 kDa MPEG with amino group at the terminal; Sunbio, Orinda, Calif.; Cat #P1AM-10) in 20 ml of 0.2M HEPES and adjust the pH to 7.8 using NaOH to obtain MPEGAM. After 20 minute activation of PAC, add to the PAC solution to MPEGAM solution. Allow the reaction to proceed for 2 hours and measure the remaining amino group of the MPEGAM by TNBS and should be none indicating that all 0.35 equivalents amino group is used up and conjugated to the PAC. If there are remaining amino group in MPEGAM, adjust pH to 5 with 6N HCl and add 1 equivalent EDC (MW=191.71), after 20 minutes adjust back the pH to 7.8 and allow to react overnight to form 15PACPEG1035. Take an aliquot of the resulting 15PACPEG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with diameter of approx 12-17 nm. Adjust pH down to 5 with 6N HCl and add 1.5 equivalents EDC (MW=191.71) and activate for 20 minutes. After 20 minutes add this activated 15PACPEG1035 solution to 10 equivalents of Nalpha,Nalpha-biscarboxymethyl-lysine (MW=262 Da) in to 25 ml of 1M HEPES buffer at pH 7.4 and allow to react overnight. Concentrate the reaction mixture to 100 ml and wash with 15 changes of water in a 100 kDa-MWCO ultrafiltration cartridge (UFP-100-E-5A). Filter-sterilize the 15PACPEG1035NTA product (using 0.2 μm polysulfone filter, Nalgene, Rochester, N.Y.) and lyophilize. Make 10 mg/ml solution of resulting 15PACPEG1035NTA and determine the hydrodynamic diameter by size exclusion chromatography using TosohG4000WXL column (0 79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should be consistent with diameter of approx 15-20 nm.

Example 38: Synthesis of 15PACPEG1035NTASO or 15PACPEG1035NTASF or 15PACPEG1035NTAPO This structure comprises of 15 kDa polyacrylic acid in which 35% of the carboxyl groups are covalently linked to 10 kDa MPEG and the remaining carboxyl groups are covalently linked to the epsilon amino group of biscarboxymethyllysine which is a nitrilotriacetic acid (NTA) derivative. The NTA is further modified to contain three sulfate (or sulfonate or phosphate) groups, each attached to the carbonyl groups of NTA. Essentially, each NTA acts as spacer to allow a cluster of three sulfate (or sulfonate or phosphate) groups to be attached to the polyacrylic acid backbone (other backbones can also be used). The 15PACPEG1035NTA (see above) can be converted to sulfated (or sulfonated or phosphorylated) carrier containing clusters of sulfate groups with up to three sulfate groups in each cluster. To do this, take 2 grams of the 15PACPEG1035NTA and dissolve it in 50 ml of 10 mM MES buffer (pH 4.7). Activate the carrier by adding 0.28 g of NHSS (MW=217.14; 1.3 mmol), followed by 0.56 g EDC (MW=191.71; 2.9 mmol), and allow to activate for 20 minutes. In a separate container dissolve 0.37 g 2-aminoethylhydrogensulfate (AES; MW=141; 2.6 mmol) or 0.45 g sulfanilic acid (SNA; MW=173; 2.6 mmol) or 0.37 g O-phosphorylethanolamine (OPE; MW=141; 2.6 mmol) in 25 ml of 1 M HEPES buffer (pH 7.3, adjust pH to 7.8 using NaOH) and measure the starting amino groups by TNBS (Spadaro et al., 1979, Anal. Chem., 96, p 317-329) which should be around 2.6 mmol, depending on the purity of AES (or SNA or OPE). Add 20-minute activated carrier to the AES (or SNA or OPE) solution. After 2 hours add another 0.56 g EDC and stir the solution overnight. Measure the amino groups by TNBS to determine the amount of decrease in amino groups which is equivalent to the amount of sulfate (or sulfonate or phosphate) groups incorporated. Wash the sulfated (or sulfonated or phosphorylated) carrier by 20 volumes of water using a 100 kDa MWCO ultrafiltration cartridge (UFP-100-E-5A; GE-Amersham), filter-sterilize (0.2 um polysulfone filter, Nalgene, Rochester, N.Y.) and lyophilize. This product (0.2 um polysulfone filter, Nalgene, Rochester, N.Y.) and lyophilize. This product (15PACPEG1035NTASO or 15PACPEG1035NTASF or 15PACPEG1035NTAPO) will have clusters of up to three sulfate (or sulfonate or phosphate) groups per cluster that is pendant to the backbone.

Use of Polymeric Backbones without Specific Modifiable Functional Groups

Example 39: Use of Polyglycine, Polyalanine, Polyvaline, Phenylalanine, Polyoxyethyleneglycol, Polyoxypropyleneglycol, and the Like (Designated in this Example as INRT as a Group) as a Polymeric Backbone is Possible by the Use of Non-Specific Photoreactive Heterobifunctional Crosslinkers that can Introduce Carboxyl Functional Groups Throughout these Polymers Examples of photoreactive heterobifunctional crosslinkers includes NHS-diazirine (Succinimidyl 4,4'-azipentanoate), NHS-LC-diazirine (Succinimidyl 6-(4,4'-azipentanamido)hexanoate), NHS-SS-diazirine (Succinimidyl 2-([4,4'-azipentanamido]ethyl)-1,3'-dithioproprionate), Sulfo-NHS-diazirine (Sulfosuccinimidyl 4,4'-azipentanoate), Sulfo-NHS-LC-diazirine (Sulfosuccinimidyl 6-(4,4'-azipentanamido)hexanoate), Sulfo-NHS-SS-diazirine (Sulfosuccinimidyl 2-([4,4'-azipentanamido]ethyl)-1,3'-dithioproprionate), ANB-NOS (N-5-Azido-2-nitrobenzoyloxysuccinimide), NHS-ASA (N-Hydroxysuccinimidyl-4-azidosalicylic acid), SADP (N-Succinimidyl(4-azidophenyl)-1,3'-dithioproprionate), Sulfo-SAND (Sulfosuccinimidyl-2-(m-azido-o-nitrobenzamido)-ethyl-1,3'-proprionate), SANPAH (N-Succinimidyl-6-(4'-azido-2'-nitrophenylamino) hexanoate), Sulfo-HSAB (N-Hydroxysulfosuccinimidyl-4-azidobenzoate), Sulfo-NHS-LC-ASA (Sulfosuccinimidyl[4-azidosalicylamido]-hexanoate), Sulfo-SADP (N-Sulfosuccinimidyl(4-azidophenyl)-1,3'-dithioproprionate), Sulfo-SAED (Sulfosuccinimidyl 2-[7-amino-4-methylcoumarin-3-acetamido] ethyl-1,3'-dithiopropionate), Sulfo-SANPAH(N-Sulfosuccinimidyl-6-(4'-azido-2'-nitrophenylamino) hexanoate), Sulfo-SBED (Sulfo-N-hydroxysuccinimidyl-2-(6-[biotinamido]-2-(p-azido benzamido)-hexanoamido) ethyl-1,3'-dithioproprionate), and Sulfo-SFAD (Sulfosuccinimidyl-(perfluoroazidobenzamido)-ethyl-1,3'-dithioproprionate). All these reagents are commercially available from Pierce, Rockford, Ill. Photo-reactive reagents are chemically inert reagents that become reactive when exposed to ultraviolet or visible light. The traditional photo-reactive groups in these reagents are aryl azides. When an aryl azide is exposed to UV light, it forms a nitrene group that can initiate addition reactions with double bonds, insertion into C—H in the absence of N—H sites (e.g., primary amines), which is the case for INRT polymers. The reaction with N—H path dominates when primary amines are present in the sample and must be avoided. Thiol-containing reducing agents (e.g., DTT or 2-mercaptoethanol) must be avoided in the sample solution during all steps before and during photoactivation. These reagents will reduce the azide. The succinimidyl-ester diazirine (SDA) reagents are a new class of crosslinkers that combine proven amine-reactive chemistry with an efficient diazirine-based photochemistry for photo-crosslinking to nearly any other functional group. Diazirine-based photocrosslinkers have better photostability than phenyl azide-based photocrosslinkers and are easily activated with long-wave UV light (330-370 nm). In the synthesis example that will follow, INRT will designate a polymer that has no readily modifiable groups.

Example 40: Synthesis of 20INRTPEGG1035NTA

This composition has INRT as the polymeric backbone with 35% of the photo-introduced carboxyl groups linked to 10 kDa MPEGAM (MW=10 kDa MPEGAM has amino group at the terminal; Sunbio, Orinda, Calif.; Cat #P1AM-10) and the remaining carboxyl groups occupied with nitrilotriacetic acid. As described above once the NTA is introduced into the polymer, addition of sulfate, sulfonate, and phosphate is straight forward (see above). Once sulfate, sulfonate, and phosphate are introduced, the chelating function of NTA is significantly reduced or eliminated. To introduce carboxyl groups to INRT polymer, dissolve 2 g of INRT (20 kDa) in 50-100 ml of appropriate solvent, add 20-40 mmol of Sulfo-NHS-diazirine and expose the solution to UV light (330-370 nm) for 2-10 minutes. Adjust pH to 9 and leave at room temperature for 2 hours to cleave the NHS and expose the carboxyl groups for analysis and quality control testing. Wash the modified product with 15 changes of water in a 3 kDa-MWCO ultrafiltration cartridge (UFP-3-E-5A). Filter-sterilize the resulting carboxylated product (20INRT) using (0.2 μm polysulfone filter, Nalgene, Rochester, N.Y.) and lyophilize to obtain 20INRT. Before using 20INRT for synthesis of 20INRTPEGG1035NTA, measure the starting carboxyl group (1 equivalent) in 1.0 g 20INRT according to the protocol by Kobayahi and Chiba (Analytical biochemistry 1994, vol 219, p 189-194). If there are less than 1 mmol of carboxyl in 1 gram of 20INRT, introduce more carboxyl by repeating the above process. To synthesize 20INRTPEGG1035NTA, take 1.0 g of INRT (with 1 equivalent carboxyl group) and dissolve in 50 ml of 10 mM MES (2-(N-morpholino)ethanesulfonic acid, Pierce, Rockford, Ill.) buffer pH 4.7 to obtain INRT solution. To the INRTPEG solution, add 1 equivalent of NHS (MW=115.14) and 1 equivalent EDC (MW=191.71) solution while stirring allow to activate for 20 minutes. In a separate container, dissolve 0.35 equivalents of MPEGAM (MW=10 kDa MPEG with amino group at the terminal; Sunbio, Orinda, Calif.; Cat #P1AM-10) in 20 ml of 0.2M HEPES and adjust the pH to 7.8 using NaOH. After 20 minute activation of INRT, add to the INRT solution to make INRTPEG solution. Allow the reaction to proceed for 2 hours and measure the remaining amino group of the MPEGAM by TNBS and should be none indicating that all 0.35 equivalents amino group is used up and conjugated to the INRT. If there are remaining amino group in MPEGAM, adjust pH to 5 with 6N HCl and add 1 equivalent EDC (MW=191.71), after 20 minutes adjust back the pH to 7.1 and allow to react overnight to form 20INRT-PEGG1035. Take an aliquot of the resulting 20INRT-PEGG1035 solution and determine the hydrodynamic diameter by size exclusion chromatography using TosohG4000WXL column (0 79×30 cm) and phosphate buffered saline (PBS; 11.9 mM phosphate, 137 mM NaCl, 2.7 mM $KPO_4$, pH 7.4) containing 15% Acetonitrile as elution solvent at a flow rate of 0.6 ml/min. The retention time should be consistent with diameter of approx 12-17 nm. Adjust pH down to 5 with 6N HCl and add 1.5 equivalents EDC (MW=191.71) and activate for 20 minutes. After 20 minutes add this activated 20INRTPEGG1035 solution to 10 equivalents of Nalpha,Nalpha-biscarboxymethyl-lysine (MW=262 Da) in to 25 ml of 1M HEPES buffer at pH 7.4 and allow to react overnight. Concentrate the reaction mixture to 100 ml and wash with 15 changes of water in a 100 kDa-MWCO ultrafiltration cartridge (UFP-100-E-5A). Filter-sterilize the 20INRTPEGG1035NTA product (using 0.2 μm polysulfone filter, Nalgene, Rochester, N.Y.) and lyophilize. Make 10 mg/ml solution of resulting 20INRTPEGG1035NTA and determine the hydrodynamic diameter by size exclusion chromatography using TosohG4000WXL column (0.79×30 cm) and phosphate buffered saline as elution solvent (PBS; 11.9 mM phosphate, 137 mM NaCl, 2.7 mM $KPO_4$, pH 7.4) containing 15% Acetonitrile at a flow rate of 0.6 ml/min. The retention time should consistent with diameter of approx 16-22 nm.

Example 41: Distinction Between Anionic Interaction and Metal-Bridge Interaction Binding studies were conducted with 50% loading (where amount of load molecule by weight is 50% of the weight of the carrier used) onto seven different carriers in the presence and absence of high salt concentration. The anionic interaction can be displaced by high concentration of NaCl (0.4M) whereas the metal bridge interaction cannot be displaced easily with high concentration of NaCl. Following carriers were tested on this study: CSPEG104G, HPPEG105G, 20PLPEG1030DTPA, 20PLPEG1030DTPASO, 20PLPEG1030DTPASF, and 20PLPEG1030DTPAPO. The 20PLPEG570DANTA-Zn is a carrier having 20 kDa plolysine backbone in which 70% of the amino groups were derivatized with 5 kDa MPEG and the remaining amino groups were derivatized with nitrilotriacetic acid using bicarbxymethyl lysine. In this case succinic acid was used as a spacer between epsilon amino group of lysine and bicarboxymethyllysine. The resulting product (20PEPEG570DANTA-Zn) was then saturated with Zinc ion and used for demonstration of metal bridge interaction. In the binding study below, no metal was used in this experiment except control with 6×His (SEQ ID NO: 66) Lysostaphin as a metal bridge positive control. For this study 0.25 mg of carrier in 250 ul solution (10 mM HEPES/400 mM NaCl, or 10 mM HEPES only) was loaded with Lysostaphin (50% carrier weight (0.125 mg)) and incubated two hours in RT. Analysis was done in triplicates. All solutions were centrifuged at 13000 rpm for 12 minutes (Eppendorf micro-centrifuge) to rule out possibility of precipitation pellet that can interfere with the analysis. The supernatants were filtered using 100 kDa MWCO membrane (cellulose) at 13000 rpm for 12 minutes to remove carrier-peptide complex (bound). The filtrate (containing free Lysostaphin) was analyzed (results shown in Table 2 below) by TNBS assay. [TNBS assay: TNBS solution was prepared by adding 30 ul of 1M Picrylsulfonic acid solution (Fluka Cat#92823) in 12 ml of 0.1M Sodium tetraborate pH 9.2. In the clear 96-well plate, 150 ul of filtrates and standards were added to assign well. 100 ul of TNBS solution was added to the wells (final volume of 250 µl). The plate was incubated for 30 minutes and the absorbance at 420 nm was measured by BioScan]. Table 2 below shows that the interaction of lysostaphin with the composition of the present invention is through anionic interaction and not by metal bridge interaction. For positive control, it is shown (last column) that the 6-his (SEQ ID NO: 66) lysostaphin interacts with Zinc (a multivalent metal ion required to form metal bridge)-containing control carrier though metal ion interaction as evident from the inability of 0.4MNaCl to displace 6-his (SEQ ID NO: 66) lysostaphin from the carrier. The second row in table 2 is the type of lysostaphin loaded to the anionic carrier. The third row in the table 2 is the percent of total lysostaphin that did not bind the carrier when there is 0.4M NaCl in the incubation mixture (note that sodium and potassium ions are not multivalent and does not form multi-coordination complex). The fourth row in the table 2 is the percent of total lysostaphin that did not bind the carrier when there is no NaCl in the incubation mixture. Note that binding of 6-His (SEQ ID NO: 66) lyso is resistant to 0.4M NaCl (a metal bridge positive control). In the presence of multivalent metal ions (not shown here), it is very surprising that the native lysostaphin binding to anionic core composition of the present invention remains sensitive to 0.4M NaCl indicating that no metal bridge is occurring.

TABLE 2

Shows the percent of the total lysostaphin loaded to the carrier that did not bind to the carrier (free unbound lysostaphin). (Table 2 discloses "6-His" as SEQ ID NO: 66)

| Carrier | CSPEG104G No metal | HPPEG105G No metal | 20PLPEG10 30DTPA No metal | 20PLPEG10 30DTPASO No metal | 20PLPEG10 30DTPASF No metal | 20PLPEG103 0DTPAPO No metal | 20PLPEG570 DANTA-Zn |
|---|---|---|---|---|---|---|---|
| Lysostaphin loaded | Native lyso | Native lyso | Native lyso | Native lyso | Native lyso | Native lyso | 6-His lyso |
| 50% loading with 0.4M NaCl | 98.2% free | 96.3% free | 98.4% free | 93.9% free | 76% free | 92.7% free | 4.6% free |
| 50% loading no NaCl | 12.1% free | 6.8% free | 8.1% free | 7.1% free | 5.1% free | 8.7% free | 2.1% free |

Example 42: Kd Determination of the Interaction Between Lysostaphin and Anionic Core Carrier Composition of the Present Invention The dissociation constant (Kd) between Lysostaphin and various carriers were determined Kds of lysostaphin was measured with following carriers in the absence of multivalent metal ions: CSPEG104G, HPPEG104G, 20PLPEG1030DTPA, 20PLPEG1030DTPASO, 20PLPEG1030DTPASF, and 20PLPEG1030DTPAPO. Lot #20090508 was loaded with 25%-150% Lysostaphin (compared to carrier weight) to measure Kd. CSPEG104G was loaded with 150%-500% Lysostaphin. Samples of the carriers listed above were loaded with 50%-250% Lysostaphin to measure Kd. Bound and free lysostaphin were separated as in Example 44 above. All the samples were measured by TNBS assay to determine free and bound as described above. With free and bound information, Scatchard plots were constructed (y-axis is bound/free and x-axis is bound). From Scatchard plots, Kd and capacity of the carrier were calculated (Slope is −1/Kd and x-intercept is the capacity) and summarized in Table 3. This shows that there is direct interaction between lysostaphin (protein with basic isoelectric point of 9.56) and the anionic core composition of the present invention. No intermediary multivalent metal ions were present in the mixture and yet Kd in nanomolar range was observed. Further, the interaction was sensitive to high NaCl concentration indicating ionic interaction and not coordination bonding.

TABLE 3

All anionic core carriers bind lysosostaphin with the most effective binder being that of highly sulfated polysaccharide (heparin).

| Carrier | CSPEG104G | HPPEG104G | 20PLPEG1030-DTPA | 20PLPEG1030-DTPASO | 20PLPEG1030-DTPASF | 20PLPEG1030-DTPAPO |
|---|---|---|---|---|---|---|
| Capacity | 6 sites | 7 sites | 5 sites | 13 sites | 6 sites | 12 sites |
| Kd | 515 nM | 96 nM | 240 nM | 290 nM | 131 nM | 606 nM |

Example 43: Lysostaphin PK Study

Four carriers were selected for PK study. CSPEG106G, HPPEG105G, 20PLPEG1030-DTPA, and 20PLPEG1030-DTPA-SO were loaded with Lysostaphin equivalent to 50% of the carrier weight. These formulations were obtained by dissolving together an appropriate amount of carrier and Lysostaphin in water and incubating for two hours followed by lyophilization. Each lyophilized formulation (including unformulated lysostaphin alone) was dissolved in saline and administered to Sprague Dawley rats (n=4) by slow (at least 1 min) i.v. bolus (12 mg lysostaphin/Kg) via the lateral tail vein. Blood samples were taken from the orbital sinus at 5 m, 15 m, 30 m, 60 m, 120 m, 4 h, 6 h, 24 h, 32 h (30 h), and 48 h and placed in tubes containing Protease Inhibitors (AEBSF, Aprotinin, E-64, EDTA, and Leupeptin). Sera were obtained by centrifugation at 13,000 rpm. All the sera were stored at −80° C. until used in the assay. 100 of serum was used in this assay for each time point. Lysostaphin's activity was measured by activity assay as follow: Stock buffer (10×) was prepared to contain 1M MOPS/10% Tween (by wt.)/5 mM EDTA/pH 7.3. The final reaction mixtures (2000) in black 96-well plate were prepared to contain 5 μg substrate, 100 mM MOPS, 1% Tween20, 0.5 mM EDTA, pH 7.3, and 100 of serum samples. The samples were added last and after addition the wells were mixed and bubbles in the solution was removed using pipette tip wet with ethanol. Fluorescence (Ex485 nm/Em535 nm) increase was monitored for two hours using Chameleon 96-well microplate fluorometer (Bioscan) every 7.5 minutes for 2 hours. The substrate gave fluorescence product when lysostaphin proteolytically cleaved it.

TABLE 4

Shows the PK profile of lysostaphin formulated with various anionic core composition of the present invention.

| Carrier | CSPEG106G | HPPEG105G | 20PLPEG1030-DTPA | 20PLPEG1030-DTPA-SO | Lysostaphin without carrier |
|---|---|---|---|---|---|
| $C_0$, μg/ml | 342 | 324 | 257 | 765 | 301 |
| $AUC_{0\ to\ last}$, hr (μg/ml) | 181 | 120 | 66.9 | 96.6 | 64.2 |
| $AUC_{0\ to\ \infty}$, hr (μg/ml) | 185 | 124 | 68.7 | 97.9 | 67 |
| Terminal $t_{1/2}$, hr | 8.44 | 6.13 | 0.713 | 0.343 | 1.53 |
| Mean residence time, hr | 5.07 | 7.91 | 1.77 | 2.11 | 0.984 |

Example 44: Binding of Various Therapeutic Peptides to Anionic Core Composition of the Present Invention Anti-inflammatory peptides (SEQ ID NO:2; SEQ ID NO:7; SEQ ID NO:31) that act intracellularly and contain basic amino acid residues that allow them to penetrate the membrane. The same property that allows them to penetrate the membrane allows them to bind to the carrier of the present invention. Binding studies were conducted with these peptides to five different anionic core carriers of the present invention. Following metal-free carriers were tested on this study: CSPEG104G, HPPEG105G, 20PLPEG1030DTPA, 20PLPEG1030DTPASO, 20PLPEG1030DTPASF, and 20PLPEG1030DTPAPO. For this study 0.1 mg (for 20% loading) or 1 mg (for 2% Loading) of each carrier in 250 ul solution (100 mM HEPES/100 mM NaCl) loaded with peptides (0.02 mg) and incubated two hours in RT. Analysis was done in duplicate. The solution was centrifuge all at 13000 rpm for 12 minutes to rule out possibility of precipitation pellet that can interfere with the analysis. The supernatant was filtered using 100 kDa MWCO membrane (cellulose) at 13000 rpm for 12 minutes to remove carrier-peptide complex (bound). The filtrate (free peptides) was analyzed by HPLC assay. Table 5 below shows that heparin with PEG was the best carrier for most of the peptides but any anionic carrier can be used for peptide SEQ ID NO:2.

TABLE 5

Shows the percent of total peptides that did not bind to the carrier (free) with the remaining peptides bound to the carrier.

| SEQ ID No./Name | % Loading | Carrier, Lot# CSPEG104G | HPPEG105G | 20PLPEG1030 DTPA | 20PLPEG1030 DTPASO | 20PLPEG1030 DTPASF | 20PLPEG1030 DTPAPO |
|---|---|---|---|---|---|---|---|
| 2/NBD | 20% loading | 0% free | 0% free | 0% free | 0% free | 0% free | 0% free |
| 7/P65 | 20% loading | 48.3% free | 5.6% free | 100% free | 100% free | 100% free | 86.7% free |
| 7/P65 | 2% loading | 30.8% free | 0% free | 50% free | 50% free | 52.4% free | 14.6% free |
| 31/PR39 | 20% loading | 61% free | 0.4% free | N/A | 87.5% free | 100% free | 86.9% free |
| 31/PR39 | 2% loading | 1.1% free | 0.5% free | N/A | 35.6% free | 42.8% free | 26.4% free |

Example 45: Kd Determination of the Interaction Between SEQ ID NO:2 and Anionic Core Carrier Composition of the Present Invention SEQ ID NO: 2 is IKKγ NEMO Binding Domain (NBD) Inhibitory Peptide that is useful in various inflammatory disease since it inhibit NFkB activation. The dissociation constant (Kd) between NBD and various carriers were determined. Kds of NBD was measured with following carriers in the absence of multivalent metal ions: HPPEG105G, 20PLPEG1030-DTPASO, and 20PLPEG1030DTPAPO. HPPEG105G and 20PLPEG1030DTPAPO were loaded with 100%-300% NBD to measure Kd. 20PLPEG1030-DTPASO was loaded with 50%-150% NBD. All the unbound NBD were measured by HPLC as above. With free and bound information, Scatchard plots were constructed (y-axis is bound/free and x-axis is bound). From Scatchard plots, Kd and capacity of the carrier were calculated (Slope is −1/Kd and x-intercept is the capacity) and the results summarized in Table 6.

TABLE 6

Shows the Kds and capacities of various carriers for NBD.

| Carrier | HPPEG105G | 20PLPEG1030DTPASO | 20PLPEG1030DTPAPO |
|---|---|---|---|
| Lot # | 20090825 | 20090831b | 20090902 |
| Capacity | 32 sites | 72 sites | 112 sites |
| Kd | 925 nM | 2.4 uM | 1.5 uM |

Example 46: Binding of Heparin Binding (HB)-Epidermal Growth Factor (-EGF) to Carrier of the Present Invention HB-EGF is an epidermal growth factor EGF-related growth factor that signals through the EGF receptor, and stimulates the proliferation of smooth muscle cells (SMC), fibroblasts, epithelial cells, and keratinocytes. HB-EGF is expressed in numerous cell types and tissues, including vascular endothelial cells and SMC, macrophages, skeletal muscle, keratinocytes, and certain tumor cells. The ability of HB-EGF to specifically bind heparin and heparin sulfate proteoglycans is distinct from other EGF-like molecules, and may be related to the enhanced mitogenic activity, relative to EGF, that HB-EGF exerts on smooth muscle cells. The human HB-EGF gene encodes a 208 amino acid transmembrane protein, which can be proteolytically cleaved to produce soluble HB-EGF. Transforming growth factor-alpha (TGF-α) is an EGF-related polypeptide growth factor that signals through the EGF receptor, and stimulates the proliferation of a wide range of epidermal and epithelial cells. It is produced by monocytes, keratinocytes, and various tumor cells. TGF-α induces transformation anchorage independence in cultured cells. Human, murine and rat TGF-α are cross-species reactive. Recombinant human TGF-α is a 50 amino acid polypeptide (5.5 kDa) which shares approximately 40% sequence homology with EGF, including 6 conserved cysteine residues, which form 3 intramolecular disulfide bonds. Betacellulin and amphiregulin are both members of the EGF family. Another growth factor family whose members will be ideal load molecules for the carrier compositions of the present invention is the fibroblast growth factor (FGF) family known in the art to have more than a dozen members. These growth factors are intended to be loaded in the composition of the present invention not because they have isoelectric point above 7 but rather they have anionic binding sites in their structure capable of binding carboxylate, sulfate, sulfonate, or phosphate. Table 5 below shows EGF binding to the carriers of the present inventions. For this study 2 mg of each carrier in 250 ul solution (100 mM HEPES/100 mM NaCl) loaded with EGF (0.01 mg) and incubated two hours in RT. Analysis was done in duplicate. The solution were centrifuged all at 13000 rpm for 12 minutes to rule out possibility of precipitation pellet that can interfere with the analysis. No precipitation was observed. The supernatant was filtered using 100 kDa MWCO membrane (cellulose) at 13000 rpm for 12 minutes to remove carrier-peptide complex (bound). The filtrate (free EGF) was analyzed by Elisa Assay (R&D systems; Minneapolis, Minn.). Table 5 below shows EGF binding to the carriers of the present inventions.

TABLE 5

Shows the percent of total EGF that did not bind to the carrier (free) with the remaining EGF-bound to the carrier.

| Carrier | HPPEG52G | HPPEG104G | CSPEG104G | CSPEG52G |
|---|---|---|---|---|
| EGF at 0.5% loading | 13% free | 13.6% free | 0% free | 0% free |

Example 47: Load Molecule (Protein or Peptide) with Isoelectric Point (pI) Above 7.3 Benefits from the Carrier Protection in the Blood When load molecule is mixed with the carrier of the present invention and injected into animals, the blood circulation time of the load molecule with isoelectric point below 7.3 is not extended compared to unformulated control (Table 7). However, when a load molecule is mixed with the carrier of the present invention and injected into animals the blood circulation time for a load molecule with isoelectric point above 7.3 is extended compared to unformulated control (Table 7). In one embodiment, the load molecule must have pI above 7.3 to benefit from the carrier of the present invention.

TABLE 7

This shows extension of in vivo blood circulation time of basic (pI > 7.3) load molecule when combined with the carrier of the present invention.

| PGC | Peptide or protein load molecules | Isoelectric Point | In Vivo average blood peptide/protein level (sampling time) | | Rodent Species, #animal tested (dose given) |
|---|---|---|---|---|---|
| HPPEG105G | GLP1 | 5.4 | N.D.* (24 hr) | N.D.* (48 hr) | Balb/c mice, n = 3 (1 mg/Kg) |
| — | GLP1 | 5.4 | N.D.* (24 hr) | N.D.* (48 hr) | Balb/c mice, n = 3 (1 mg/Kg) |
| CSPEG106G | Lysostaphin | 9.56 | 1000 ng/ml (24 hr) | 420 ng/ml (48 hr) | Sprague Dawley Rats, n = 5 (10 mg/Kg) |
| — | Lysostaphin | 9.56 | N.D.* (24 hr) | N.D.* (48 hr) | Sprague Dawley Rats, n = 5 (10 mg/Kg) |
| CSPEG52G | Heparin-binding EGF | 8.56 | 3,700 pg/ml (6 hr) | 40 pg/ml (24 hr) | Balb/c mice, n = 3 (300 μg/Kg) |
| — | Heparin-binding EGF | 8.56 | N.D.* (6 hr) | N.D.* (24 hr) | Balb/c mice, n = 3 (300 μg/Kg) |
| HPPEG52G | PR39 | 9.96 | 840 ng/ml (24 h) | 310 ng/ml (48 hr) | Sprague Dawley Rats, n = 5 (10 mg/Kg) |
| — | PR39 | 9.96 | 370 ng/ml (24 h) | 30 ng/ml (48 hr) | Sprague Dawley Rats, n = 5 (10 mg/Kg) |

*N.D. Indicates the level is not detected or it is at the background level. All background signals were subtracted from the readings. The assays used for GLP1 and Heparin binding EGF are Elisa assay kits from Millipore (Bedford, MA) and R&D systems (Minneapolis, MN), respectively and used according to manufacturer's instruction. The assay used for lysostaphin is a FRET assays that increases fluorescence when degraded by lysostaphin and the assay solution was monitored using fluorescence microplate reader (Molecular Devices, CA). The assay used for PR39 is direct fluorescence reading of PR39 labeled with Fluorescein.

Mammalian blood vasculature is lined with anionic charges (proteoglycans) and the blood constituent (proteins and cells) are all anionic. Other neutral components such as triglyceride are packed in negatively charged lipoprotein. It is surprising and unexpected that the integrity of ionic interaction between the anionic carrier and the cationic load molecule (basic load molecule) is maintained in the blood. The blood has osmolality of 280 mOsmol or about 150 mM salt which can disrupt ionic interaction. In addition, blood contains anionic proteins and cells which are anionic and can compete or bind load molecules and take them away from the anionic carriers of the present invention. Anionic blood vessel walls can also remove the load molecules from the carrier. Yet the results above indicate that these physiological forces do not overcome the ionic interactions between the load molecules and the anionic carrier of the present invention.

While preferred embodiments of the present invention have been shown and described herein, it will be apparent to those skilled in the art that such embodiments are provided by way of example only. It should be understood that various alternatives to the embodiments of the invention described herein may be employed in practicing the invention. It should be noted that for the purpose of clarity of the scope of the invention, the compositions of the present invention are described in blocks such as polymeric backbone, protective chains, anionic groups, and load molecules. Each block is not intended to be an inherent component of the other. For example, in certain embodiments, the backbone contains carboxyl groups used to form amide that holds the backbone intact such carboxyl groups are not the same carboxyl groups that make up the other blocks such as the anionic groups (i.e. no circular argument should be used in the interpretation of the claims). In certain embodiments, polymers that naturally contain anionic groups (carboxyl, sulfate, sulfonate, or phosphate) will be treated for the purpose of this specification to contain both the backbone (first block) and the anionic group (second block) of the composition of the present invention. In other embodiments, compositions envisioned with anionic groups are distinct from any anionic groups that may be present in the polymer backbone. The blocks that made up a particular composition are associated with each other in a defined manner and each block should not overlap each other in the interpretation of the claims.

What is claimed is:

1. A composition comprising:

(a) a polymer consisting of (i) a polymer backbone selected from polylysine, polyornithine, polyarginine, polyglutamate, polyaspartate, polycysteine, polyserine, polythreonine, polytyrosine, chondroitin sulfate, dermatan sulfate, keratan sulfate, carageenan, pectin, fucoidan, dextran, polymethylacrylic acid, polyacrylic acid, and polyallylamine;

(ii) multiple protective chains covalently linked to the polymer backbone, wherein each protective chain is independently selected from a group consisting of a linear poly(ethyleneglycol) and a linear methoxy poly(ethyleneglycol), and each protective chain is singly terminally covalently linked to a monomeric unit on the polymer backbone via one covalent bond;

(iii) an anionic group attached to a monomeric unit on the polymer backbone by a covalent bond, wherein the anionic group is selected from the group consisting of phosphate, sulfate, sulfonate, and carboxyl, or an anionic cluster comprising two or more anionic groups attached to a monomeric unit on the polymer backbone by a single covalent bond, wherein the anionic groups are each selected from the group consisting of phosphate, sulfate, sulfonate, and carboxyl; and (b) a load molecule linked directly by electrostatic interaction to the anionic group or the anionic cluster of the polymer without an intermediary metal ion, wherein the load molecule (i) comprises a cell penetrating peptide;

(ii) comprises an anionic binding domain; or (iii) has an isoelectric point greater than 7.3;

wherein at least 85% of the load molecule remains linked to the anionic group or the anionic cluster in the presence of 100 mM aqueous NaCl solution.

2. The composition of claim 1, wherein the load molecule is selected from the group consisting of: (i) a peptide; (ii) a protein; and (iii) a small organic molecule.

3. The composition of claim 1, wherein the load molecule is a peptide or a protein comprising a cell penetrating contiguous sequence of 5-10 amino acids, and wherein the number of basic amino acid (lysine and arginine) minus the number of acidic amino acids (glutamate and aspartate) is 2 or greater.

4. The composition of claim 3, wherein the cell penetrating contiguous sequence in the peptide comprises of a sequence selected from the group consisting of: 1) Lys-Lys-Lys-Lys, 2) Lys-Lys-Lys-Arg, 3) Lys-Lys-Arg-Lys, 4) Lys-Lys-Arg-Arg, 4) Lys-Arg-Arg-Lys, 5) Lys-Arg-Arg-Arg, and 6) Arg-Arg-Arg-Arg, wherein any amino acid can be D or L isomer and the orientation of the sequence as presented can be amino to carboxyl or carboxyl to amino.

5. The composition of claim 1, wherein the load molecule comprises an agent selected from the group consisting of SEQ ID NOS: 1-59, lysostaphin, an epithelial growth factor (EGF), an interferon, a Fibroblast growth factor (FGF), a Vascular endothelial growth factor (VEGF), Hepatocyte growth factor (HGF), a Transforming growth factor (TGF), Nerve growth factor (NGF), and a Platelet derived growth factor (PDGF).

6. The composition of claim 1, wherein the load molecule comprises an agent selected from the group consisting of the last 11 amino acids of SEQ ID NO: 1, the last 8 amino acids of SEQ ID NO: 5, the last 12 amino acids of SEQ ID NO: 7, the last 10 amino acids of SEQ ID NO: 9 and the last 14 amino acids of SEQ ID NO: 10.

7. The composition of claim 1, wherein the load molecule comprises an anti-inflammatory agent selected from the group consisting of SEQ ID NOS: 1-11.

8. The composition of claim 1, wherein the load molecule comprises an anti-infective agent selected from the group consisting of lysostaphin, interferon, and SEQ ID NOS: 12-45.

9. The composition of claim 1, wherein the load molecule comprises a growth factor or an anti-apoptotic agent selected from the group consisting of SEQ ID NOS: 31-34 and 46-49 inclusive, a Fibroblast growth factor (FGF), a Vascular endothelial growth factor (VEGF), Hepatocyte growth factor (HGF), a Transforming growth factor (TGF), Nerve growth factor (NGF), and a platelet derived growth factor (PDGF).

10. The composition of claim 1, wherein the load molecule comprises a growth inhibitor selected from the group consisting of SEQ ID NOS: 50-59 and an interferon.

11. The composition of claim 1, wherein the backbone is polylysine, and the anionic group is carboxyl.

12. The composition of claim 11, wherein the load molecule is selected from the group consisting of SEQ ID NO: 26-29, 32-34, FGF, and HGF.

13. The composition of claim 1, wherein the backbone is chondroitin.

14. The composition of claim 1, wherein the load molecule is heparin binding EGF.

15. The composition of claim 1, wherein the load molecule is lysostaphin.

16. The composition of claim 1, wherein the load molecule is SEQ ID NO: 31.

* * * * *

UNITED STATES PATENT AND TRADEMARK OFFICE

CERTIFICATE OF CORRECTION

PATENT NO. : 10,010,613 B2
APPLICATION NO. : 13/395090
DATED : July 3, 2018
INVENTOR(S) : G. M. Castillo et al.

It is certified that error appears in the above-identified patent and that said Letters Patent is hereby corrected as shown below:

In the Claims

| Column | Line | Error |
|---|---|---|
| 103 (Claim 3, Line 4) | 65 | "acid" should read --acids-- |

Signed and Sealed this
Ninth Day of July, 2019

Andrei Iancu
*Director of the United States Patent and Trademark Office*